US012583405B2

(12) United States Patent
Zahid et al.

(10) Patent No.: US 12,583,405 B2
(45) Date of Patent: Mar. 24, 2026

(54) VEHICLE MODIFICATIONS TO OPTIMIZE AN OCCUPANT'S CONDITION

(71) Applicant: TOYOTA MOTOR NORTH AMERICA, INC., Plano, TX (US)

(72) Inventors: Imad Zahid, Carrollton, TX (US); Joshua C. Batie, Frisco, TX (US)

(73) Assignees: TOYOTA MOTOR NORTH AMERICA, INC., Plano, TX (US); TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 61 days.

(21) Appl. No.: 18/661,558

(22) Filed: May 10, 2024

(65) Prior Publication Data

US 2025/0346200 A1     Nov. 13, 2025

(51) Int. Cl.
B60R 16/037     (2006.01)
A61B 5/00     (2006.01)

(52) U.S. Cl.
CPC .......... B60R 16/037 (2013.01); A61B 5/4806 (2013.01)

(58) Field of Classification Search
CPC ......................... B60R 16/037; A61B 5/4806
See application file for complete search history.

(56) References Cited

U.S. PATENT DOCUMENTS

| | | | |
|---|---|---|---|
| 10,223,842 B1 | 3/2019 | Lee et al. | |
| 10,331,142 B2 | 6/2019 | Bar-Tal et al. | |

| | | | |
|---|---|---|---|
| 10,399,492 B1 | 9/2019 | Paraskevas et al. | |
| 10,745,009 B2 | 8/2020 | Jang et al. | |
| 10,819,966 B2 | 10/2020 | Alaniz et al. | |
| 11,112,795 B1 | 9/2021 | Mandi et al. | |
| 11,291,917 B2 | 4/2022 | Beltran et al. | |
| 11,318,952 B2 | 5/2022 | Hotson et al. | |
| 11,491,903 B2 | 11/2022 | Yamamoto et al. | |
| 11,861,917 B2 | 1/2024 | Chan et al. | |
| 2004/0133082 A1 | 7/2004 | Abraham-Fuchs et al. | |
| 2015/0127215 A1 | 5/2015 | Chatterjee | |
| 2015/0366350 A1 | 12/2015 | Di Censo et al. | |
| 2017/0057492 A1 | 3/2017 | Edgington et al. | |
| 2017/0329329 A1 | 11/2017 | Kamhi et al. | |

(Continued)

FOREIGN PATENT DOCUMENTS

| | | |
|---|---|---|
| CN | 113344210 A | 9/2021 |
| EP | 3809347 A1 | 4/2021 |

(Continued)

OTHER PUBLICATIONS

Bitkina et al., "Identifying Traffic Context Using Driving Stress: A Longitudinal Preliminary Case Study," Sensors MDPI, May 9, 2019.

(Continued)

*Primary Examiner* — Tan Q Nguyen

(57)     ABSTRACT

An example operation includes one or more of identifying a state of an individual associated with a vehicle based on data of the individual stored in a profile, determining a current time of day from a system of the vehicle, determining a setting to change on one or more systems within the vehicle based on execution of an artificial intelligence (AI) model on the state of the individual and the current time of day, and changing the setting on the one or more systems within the vehicle while the individual is within the vehicle.

20 Claims, 27 Drawing Sheets

100B

(56) References Cited

U.S. PATENT DOCUMENTS

| | | | | |
|---|---|---|---|---|
| 2018/0335310 | A1 | 11/2018 | Naoki | |
| 2020/0070657 | A1 | 3/2020 | Kim | |
| 2020/0152197 | A1 | 5/2020 | Penilla et al. | |
| 2020/0231178 | A1 | 7/2020 | Murayama et al. | |
| 2020/0311475 | A1 | 10/2020 | el Kaliouby et al. | |
| 2020/0369271 | A1 | 11/2020 | Jang et al. | |
| 2022/0016999 | A1 | 1/2022 | Burk et al. | |
| 2022/0089063 | A1 | 3/2022 | Fields et al. | |
| 2022/0114477 | A1 | 4/2022 | Kou et al. | |
| 2022/0126864 | A1 | 4/2022 | Moustafa et al. | |
| 2022/0176923 | A1 | 6/2022 | Henderson et al. | |
| 2022/0188697 | A1 | 6/2022 | Seth | |
| 2022/0280107 | A1* | 9/2022 | Shimuta | A61B 5/6826 |
| 2022/0309203 | A1 | 9/2022 | Yang et al. | |
| 2023/0058086 | A1 | 2/2023 | Vassilovski et al. | |
| 2023/0143946 | A1* | 5/2023 | Konrardy | B60W 30/18163 701/23 |
| 2023/0174089 | A1* | 6/2023 | Khamis | B60W 50/10 701/1 |
| 2023/0191871 | A1* | 6/2023 | Feltham | B60H 1/00499 701/36 |
| 2023/0205201 | A1* | 6/2023 | Cella | G05D 1/226 701/123 |
| 2023/0351174 | A1 | 11/2023 | Lee et al. | |
| 2023/0401952 | A1 | 12/2023 | Beaurepaire et al. | |
| 2024/0001915 | A1 | 1/2024 | Yun et al. | |
| 2024/0346863 | A1 | 10/2024 | Carlton et al. | |
| 2025/0001959 | A1 | 1/2025 | Mankame et al. | |
| 2025/0336291 | A1 | 10/2025 | Matthews et al. | |

FOREIGN PATENT DOCUMENTS

| | | | |
|---|---|---|---|
| EP | 3825979 | A1 | 5/2021 |
| EP | 3923259 | A1 | 12/2021 |
| KR | 20230152448 | A | 11/2023 |
| WO | 2021042195 | A1 | 3/2021 |

OTHER PUBLICATIONS

Unknown, "Apple Watch Ultra User Guide," https://support.apple.com/guide/watch-ultra/stay-fit-with-apple-watch-ultra-apdc01259d1d/watchos, last downloaded on Feb. 27, 2024.

Unknown, "Body Signals: How Stress Affects The Body," Green Boro Chiropractic, published Jun. 4, 2020, https://www.greensborochiropractor.net/body-signals-stress/.

Unknown, "Chromotherapy is the Key to a Better Mood," Beem Light Sauna, Feb. 2, 2023, https://beemlightsauna.com/chromotherapy-key-to-improving-mood/.

Unknown, "Distracted Driving,", United States Department of Transportation, NHTSA, https://www.nhtsa.gov/risky-driving/distracted-driving, last downloaded on Feb. 27, 2024.

Unknown, "Mental health: these songs are proven to reduce stress," Wellbeing and Mental Health, World Economic Forum, Jul. 22, 2021, https://www.weforum.org/agenda/2021/07/stress-reducing-songs-mental-health/.

Unknown, "Registered vehicles per 1,000 people, 2017," Our World In Data, downloaded on Feb. 24, 2024, https://ourworldindata.org/grapher/registered-vehicles-per-1000-people.

Unknown, "Tesla Lounge," last downloaded Feb. 27, 2024, //www.reddit.com/r/TeslaLounge/comments/qfi6ha/tesla_workaround_for_the_103_issue_was_disabling/?rdt=61929.

Unknown, "The Effects of Poor Posture on your Health," Posturepro, Nov. 25, 2021, https://www.facebook.com/Posturepro/posts/how-poor-posture-affects-your-heath/5156208934392674/.

Unknown, "What are ADAS Systems?" Fundacion MAPFRE, last downloaded Feb. 27, 2024, https://www.fundacionmapfre.org/en/education-outreach/road-safety/adas-systems/what-are-adas-systems/.

Vijayan et al., "Review of Wearable Devices and Data Collection Considerations for Connected Health," sensors MDPI, Aug. 19, 2021.

Whitney, "Stay Motivated: How to Track Workouts on Your iPhone Without an Apple Watch," updated Sep. 13, 2022, https://www.pcmag.com/how-to/track-workout-on-iphone-without-apple-watch.

* cited by examiner

100B

100C

200

VEHICLE 202

COMPUTER-READABLE MEDIUM 242C

Identifying a State of an Individual Based on Data Stored in a Profile 244C

Determining a Current Time of Day 246C

Determining a Setting Change in a Vehicle based on Execution of an AI Model on the State and the Current Time 248C Changing a Setting of One or more Systems in the Vehicle 250C

PROCESSOR 204

ELEMENTS 230

240

260

270

400A

400C

400D

400E

500A

510

512

ASSETS
RECEIVED

ASSETS
TRANSFERRED $T_1$ $T_2$ ... $T_N$    TRANSACTION
MODULE

520

VEHICLE
PROCESSOR

526

525

$T_1$ $T_2$ ... $T_N$    DATABASE

530

500B

Figure 5F:
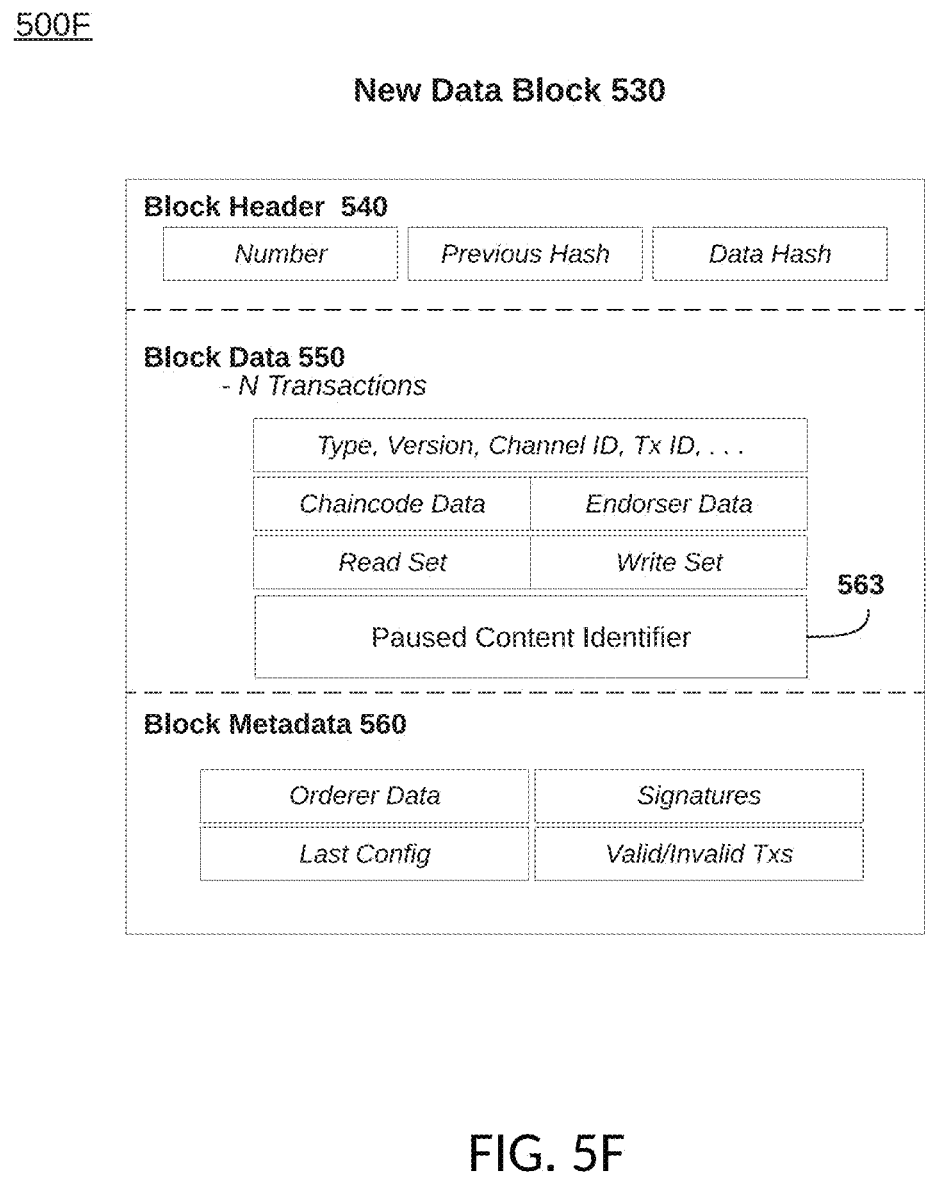

500F

New Data Block 530

Block Header  540

| Number | Previous Hash | Data Hash |

Block Data 550
　　　- *N Transactions*

| Type, Version, Channel ID, Tx ID, . . . | |
| Chaincode Data | Endorser Data |
| Read Set | Write Set |
| Paused Content Identifier | |

563

Block Metadata 560

| Orderer Data | Signatures |
| Last Config | Valid/Invalid Txs |

VEHICLE MODIFICATIONS TO OPTIMIZE AN OCCUPANT'S CONDITION

CROSS-REFERENCE TO RELATED APPLICATIONS

This application is related to four (4) co-pending U.S. non-provisional patent applications, Ser. No. 18/661,536 entitled, "ARTIFICIAL INTELLIGENCE-BASED VEHICLE SEAT CONFIGURATION," Ser. No. 18/661,541 entitled, "ARTIFICIAL INTELLIGENCE-BASED MEASUREMENT OF ROAD CONDITION," Ser. No. 18/661, 545 entitled, "VEHICLE MODIFICATIONS TO BENEFIT AN OCCUPANT'S CONDITION," and Ser. No. 18/661, 551 entitled, "VEHICLE MODIFICATIONS TO OPTIMIZE AN OCCUPANT'S CONDITION," all of which were filed on the same day and incorporated herein by reference in their entirety.

BACKGROUND

Vehicles or transports, such as cars, motorcycles, trucks, planes, trains, etc., generally provide transportation needs to occupants and/or goods in a variety of ways. Functions related to vehicles may be identified and utilized by various computing devices, such as a smartphone or a computer located on and/or off the vehicle.

SUMMARY

One example embodiment provides a method that includes one or more of identifying a state of an individual associated with a vehicle based on data of the individual stored in a profile, determining a current time of day from a system of the vehicle, determining a setting to change on one or more systems within the vehicle based on execution of an artificial intelligence (AI) model on the state of the individual and the current time of day, and changing the setting on the one or more systems within the vehicle while the individual is within the vehicle.

Another example embodiment provides an apparatus that includes a memory communicably coupled to a processor, wherein the processor is configured to perform one or more of identify a state of an individual associated with a vehicle based on data of the individual stored in a profile, determine a current time of day from a system of the vehicle, determine a setting to change on one or more systems within the vehicle based on execution of an artificial intelligence (AI) model on the state of the individual and the current time of day, and change the setting on the one or more systems within the vehicle while the individual is within the vehicle.

A further example embodiment provides a computer-readable storage medium comprising instructions, that when read by a processor, cause the processor to perform one or more of identifying a state of an individual associated with a vehicle based on data of the individual stored in a profile, determining a current time of day from a system of the vehicle, determining a setting to change on one or more systems within the vehicle based on execution of an artificial intelligence (AI) model on the state of the individual and the current time of day, and changing the setting on the one or more systems within the vehicle while the individual is within the vehicle.

BRIEF DESCRIPTION OF THE DRAWINGS

FIG. 5F illustrates an example new data block, according to example embodiments.

DETAILED DESCRIPTION

Figure 1A:
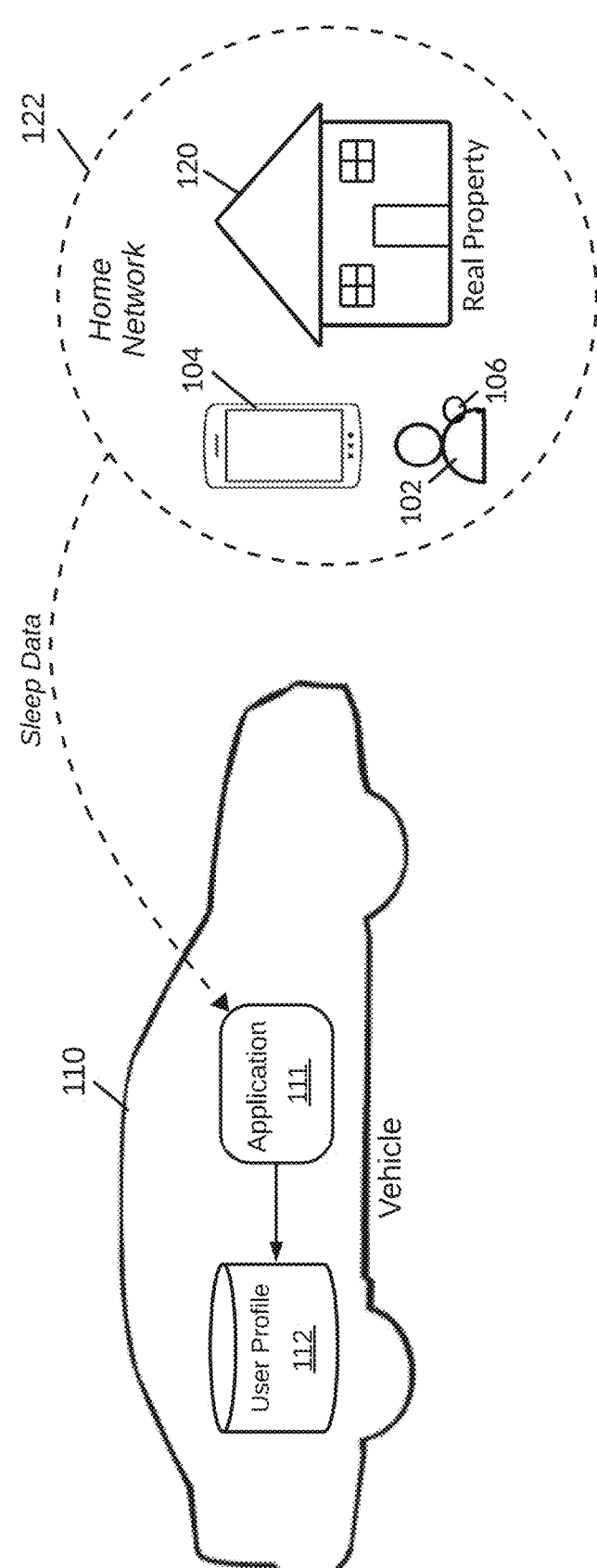
FIG. 1A is a diagram illustrating a process of receiving state data of an individual from a network outside of a vehicle according to example embodiments.

It will be readily understood that the instant components, as generally described and illustrated in the figures herein, may be arranged and designed in a wide variety of different configurations. Thus, the following detailed description of the embodiments of at least one of a method, apparatus, computer-readable storage medium and system, as represented in the attached figures, is not intended to limit the scope of the application as claimed but is merely representative of selected embodiments. Multiple embodiments depicted herein are not intended to limit the scope of the solution. The computer-readable storage medium may be a non-transitory computer-readable medium or a non-transitory computer-readable storage medium.

Communications between the vehicle(s) and certain entities, such as remote servers, other vehicles and local computing devices (e.g., smartphones, personal computers, vehicle-embedded computers, etc.) may be sent and/or received and processed by one or more 'components' which may be hardware, firmware, software, or a combination thereof. The components may be part of any of these entities or computing devices or certain other computing devices. In one example, consensus decisions related to blockchain transactions may be performed by one or more computing devices or components (which may be any element described and/or depicted herein) associated with the vehicle(s) and one or more of the components outside or at a remote location from the vehicle(s).

The instant features, structures, or characteristics described in this specification may be combined in any suitable manner in one or more embodiments. For example, the usage of the phrases "example embodiments," "some embodiments,", "a first embodiment", or other similar language throughout this specification refers to the fact that a particular feature, structure, or characteristic described in connection with the one or more embodiments may be included in one or more other embodiments described or depicted herein. Thus, the one or more embodiments, described or depicted throughout this specification can all refer to the same embodiment. Thus, these embodiments may work in conjunction with any of the other embodiments, may not be functionally separate, and the described features, structures, or characteristics may be combined in any suitable manner in one or more embodiments. Although described in a particular manner, by example only, or more feature(s), element(s), and step(s) described herein may be utilized together and in various combinations, without exclusivity, unless expressly indicated otherwise herein. In the figures, any connection between elements can permit one-way and/or two-way communication, even if the depicted connection is a one-way or two-way connection, such as an arrow.

In the instant solution, a vehicle may include one or more of cars, trucks, Internal Combustion Engine (ICE) vehicles, battery electric vehicle (BEV), fuel cell vehicles, any vehicle utilizing renewable sources, hybrid vehicles, e-Palettes, buses, motorcycles, scooters, bicycles, boats, recreational vehicles, planes, drones, Unmanned Aerial Vehicles (UAV) and any object that may be used to transport people and/or goods from one location to another.

In addition, while the term "message" may have been used in the description of embodiments, other types of network data, such as, a packet, frame, datagram, etc. may also be used. Furthermore, while certain types of messages and signaling may be depicted in exemplary embodiments they are not limited to a certain type of message and signaling.

Example embodiments provide methods, systems, components, non-transitory computer-readable mediums, devices, and/or networks, which provide at least one of a transport (also referred to as a vehicle or car herein), a data collection system, a data monitoring system, a verification system, an authorization system, and a vehicle data distribution system. The vehicle status condition data received in the form of communication messages, such as wireless data network communications and/or wired communication messages, may be processed to identify vehicle status conditions and provide feedback on the condition and/or changes of a vehicle. In one example, a user profile may be applied to a particular vehicle to authorize a current vehicle event, service stops at service stations, to authorize subsequent vehicle rental services, and enable vehicle-to-vehicle communications.

Within the communication infrastructure, a decentralized database is a distributed storage system which includes multiple nodes that communicate with each other. A blockchain is an example of a decentralized database, which includes an append-only immutable data structure (i.e., a distributed ledger) capable of maintaining records between untrusted parties. The untrusted parties are referred to herein as peers, nodes, or peer nodes. Each peer maintains a copy of the database records, and no single peer can modify the database records without a consensus being reached among the distributed peers. For example, the peers may execute a consensus protocol to validate blockchain storage entries, group the storage entries into blocks, and build a hash chain via the blocks. This process forms the ledger by ordering the storage entries, as is necessary, for consistency. In public or permissionless blockchains, anyone can participate without a specific identity. Public blockchains can involve cryptocurrencies and use consensus-based on various protocols such as proof of work (PoW). Conversely, a permissioned blockchain database can secure interactions among a group of entities, which share a common goal, but which do not or cannot fully trust one another, such as businesses that exchange funds, goods, information, and the like. The instant solution can function in a permissioned and/or a permissionless blockchain setting.

Smart contracts are trusted distributed applications which leverage tamper-proof properties of the shared or distributed ledger (which may be in the form of a blockchain) and an underlying agreement between member nodes, which is referred to as an endorsement or endorsement policy. In general, blockchain entries are "endorsed" before being committed to the blockchain while entries which are not endorsed are disregarded. A typical endorsement policy allows smart contract executable code to specify endorsers for an entry in the form of a set of peer nodes that are necessary for endorsement. When a client sends the entry to the peers specified in the endorsement policy, the entry is executed to validate the entry. After validation, the entries enter an ordering phase in which a consensus protocol produces an ordered sequence of endorsed entries grouped into blocks.

Nodes are the communication entities of the blockchain system. A "node" may perform a logical function in the sense that multiple nodes of different types can run on the same physical server. Nodes are grouped in trusted domains and are associated with logical entities that control them in various ways. Nodes may include different types, such as a client or submitting-client node, which submits an entryinvocation to an endorser (e.g., peer), and broadcasts entry proposals to an ordering service (e.g., ordering node). Another type of node is a peer node, which can receive client submitted entries, commit the entries, and maintain a state and a copy of the ledger of blockchain entries. Peers can also have the role of an endorser. An ordering-service-node or orderer is a node running the communication service for all nodes and which implements a delivery guarantee, such as a broadcast to each of the peer nodes in the system when committing entries and modifying a world state of the blockchain. The world state can constitute the initial blockchain entry, which normally includes control and setup information.

A ledger is a sequenced, tamper-resistant record of all state transitions of a blockchain. State transitions may result from smart contract executable code invocations (i.e., entries) submitted by participating parties (e.g., client nodes, ordering nodes, endorser nodes, peer nodes, etc.). An entry may result in a set of asset key-value pairs being committed to the ledger as one or more operands, such as creates, updates, deletes, and the like. The ledger includes a blockchain (also referred to as a chain), which stores an immutable, sequenced record in blocks. The ledger also includes a state database, which maintains a current state of the blockchain. There is typically one ledger per channel. Each peer node maintains a copy of the ledger for each channel of which they are a member.

A chain is an entry log structured as hash-linked blocks, and each block contains a sequence of N entries where N is equal to or greater than one. The block header includes a hash of the blocks' entries, as well as a hash of the prior block's header. In this way, all entries on the ledger may be sequenced and cryptographically linked together. Accordingly, it is not possible to tamper with the ledger data without breaking the hash links. A hash of a most recently added blockchain block represents every entry on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain entry log. Since the current state represents the latest key values known to a channel, it is sometimes referred to as a world state. Smart contract executable code invocations execute entries against the current state data of the ledger. To make these smart contract executable code interactions efficient, the latest values of the keys may be stored in a state database. The state database may be simply an indexed view into the chain's entry log and can therefore be regenerated from the chain at any time. The state database may automatically be recovered (or generated if needed) upon peer node startup and before entries are accepted.

A blockchain is different from a traditional database in that the blockchain is not a central storage but rather a decentralized, immutable, and secure storage, where nodes must share in changes to records in the storage. Some properties that are inherent in blockchain and which help implement the blockchain include, but are not limited to, an immutable ledger, smart contracts, security, privacy, decentralization, consensus, endorsement, accessibility, and the like.

Example embodiments provide a service to a particular vehicle and/or a user profile that is applied to the vehicle. For example, a user may be the owner of a vehicle or the operator of a vehicle owned by another party. The vehicle may require service at certain intervals, and the service needs may require authorization before permitting the services to be received. Also, service centers may offer services to vehicles in a nearby area based on the vehicle's current route plan and a relative level of service requirements (e.g., immediate, severe, intermediate, minor, etc.). The vehicle needs may be monitored via one or more vehicle and/or road sensors or cameras, which report sensed data to a central controller computer device in and/or apart from the vehicle. This data is forwarded to a management server for review and action. A sensor may be located on one or more of the interior of the vehicle, the exterior of the vehicle, on a fixed object apart from the vehicle, and on another vehicle proximate the vehicle. The sensor may also be associated with the vehicle's speed, the vehicle's braking, the vehicle's acceleration, fuel levels, service needs, the gear-shifting of the vehicle, the vehicle's steering, and the like. A sensor, as described herein, may also be a device, such as a wireless device in and/or proximate to the vehicle. Also, sensor information may be used to identify whether the vehicle is operating safely and whether an occupant has engaged in any unexpected vehicle conditions, such as during a vehicle access and/or utilization period. Vehicle information collected before, during and/or after a vehicle's operation may be identified and stored in a transaction on a shared/distributed ledger, which may be generated and committed to the immutable ledger as determined by a permission granting consortium, and thus in a "decentralized" manner, such as via a blockchain membership group.

Each interested party (i.e., owner, user, company, agency, etc.) may want to limit the exposure of private information, and therefore the blockchain and its immutability can be used to manage permissions for each particular user vehicle profile. A smart contract may be used to provide compensation, quantify a user profile score/rating/review, apply vehicle event permissions, determine when service is needed, identify a collision and/or degradation event, identify a safety concern event, identify parties to the event and provide distribution to registered entities seeking access to such vehicle event data. Also, the results may be identified, and the necessary information can be shared among the registered companies and/or individuals based on a consensus approach associated with the blockchain. Such an approach may not be implemented on a traditional centralized database.

Various driving systems of the instant solution can utilize software, an array of sensors as well as machine learning functionality, light detection and ranging (Lidar) projectors, radar, ultrasonic sensors, etc. to create a map of terrain and road that a vehicle can use for navigation and other purposes. In some embodiments, GPS, maps, cameras, sensors, and the like can also be used in autonomous vehicles in place of Lidar.

The instant solution includes, in certain embodiments, authorizing a vehicle for service via an automated and quick authentication scheme. For example, driving up to a charging station or fuel pump may be performed by a vehicle operator or an autonomous vehicle and the authorization to receive charge or fuel may be performed without any delays provided the authorization is received by the service and/or charging station. A vehicle may provide a communication signal that provides an identification of a vehicle that has a currently active profile linked to an account that is authorized to accept a service, which can be later rectified by compensation. Additional measures may be used to provide further authentication, such as another identifier may be sent from the user's device wirelessly to the service center to replace or supplement the first authorization effort between the vehicle and the service center with an additional authorization effort.

Data shared and received may be stored in a database, which maintains data in one single database (e.g., database server) and generally at one particular location. This location is often a central computer, for example, a desktop central processing unit (CPU), a server CPU, or a mainframe computer. Information stored on a centralized database is typically accessible from multiple different points. A centralized database is easy to manage, maintain, and control, especially for purposes of security because of its single location. Within a centralized database, data redundancy is minimized as having a single storing place of all data also implies that a given set of data only has one primary record. A blockchain may be used for storing vehicle-related data and transactions.

Any of the actions described herein may be performed by one or more processors (such as a microprocessor, a sensor, an Electronic Control Unit (ECU), a head unit, and the like), with or without memory, which may be located on-board the vehicle and/or off-board the vehicle (such as a server, computer, mobile/wireless device, etc.). The one or more processors may communicate with other memory and/or other processors on-board or off-board other vehicles to utilize data being sent by and/or to the vehicle. The one or more processors and the other processors can send data, receive data, and utilize this data to perform one or more of the actions described or depicted herein.

The morbidity and mortality due to stress-related illness is alarming. Emotional stress is a significant contributing factor to the leading causes of death in the United States including cancer, coronary heart disease, accidental injuries, respiratory disorders, cirrhosis of the liver, and suicide. The Center for Disease Control and Prevention estimates stress accounts for about 75% of all doctor's visits. This involves a vast span of physical complaints including, but not limited to, headache, back pain, heart problems, upset stomach, stomach ulcer, sleep problems, tiredness, and accidents. According to Occupational Health and Safety News and the National Council on Compensation of Insurance, up to 90% of all visits to primary care physicians are for stress-related complaints.

Meanwhile, exposure to light may improve communication between the brain regions responsible for processing emotions like anxiety and stress. Light exposure also activates brain regions that promote cognitive performance, memory formation, and mood regulation. Studies have found that different colors can positively impact our physical and emotional states by affecting our hormones, heart rate, respiration rate, blood pressure, brain waves, and other physiological functions. For instance, blue light has been shown to reduce cortisol levels (which is the hormone associated with stress), while yellow light has been linked to increased serotonin levels (which is the hormone responsible for regulating mood and happiness). In addition, research suggests that exposure to specific colors may help reduce symptoms of depression and anxiety while promoting relaxation and improved sleep quality. Furthermore, exposure to light and the absence of light affect a person's circadian rhythm, the natural process that controls our daily sleep, wakefulness schedule, and our body's internal clock. When the circadian rhythm is disrupted, the person may feel lowered energy levels and increased anxiety, stress, and irritability.

In addition, music has the ability to reduce stress and improve mental health. For example, a study by Queen Mary University of London demonstrated that playing music during and after medical operations calmed patients and reduced their pain. More recently, a 2020 study found that 57% of Americans listen to music to manage stressful situations, compared to 40% who find exercise helpful and 33% who use video games to unwind. Contemporary research suggests that music has significant power to help reduce stress and anxiety, relieve pain, and improve focus, among other benefits. A 2020 overview of research into music and stress suggests that listening to music can lower our heart rate and cortisol levels, release endorphins, improve our sense of well-being, and reduce stress-related symptoms.

The example embodiments are directed to an artificial intelligence (AI) system that is capable of modifying settings of various systems within a vehicle to reduce stress and to increase relaxation, alertness, or the like, based on a state of a driver/occupant of the vehicle. In some embodiments, an AI model may receive sensor data or input preferences provided by a user which provide information about the sleep habits (e.g., a circadian rhythm, etc.) of an occupant of the vehicle. The AI model may use the sleep habits and a current time of the day to generate an experience inside the vehicle that appeals to the circadian rhythm of the occupant(s). In some embodiments, the system may be embedded within a vehicle. As another example, the system may be integrated within a remote platform such as a remote server, cloud platform, or the like, which is connected to the vehicle through a computer network.

The system described herein can adjust the user experience within a vehicle or an analogous setting external to the vehicle, such as a home or office environment, contingent upon the time of day. This innovation leverages an AI model embedded within the vehicle's ecosystem to personalize the ambiance, thereby facilitating the user's transition into a state of increased alertness or relaxation, corresponding to a part of the day. The system may accomplish this by orchestrating a series of adjustments to the vehicle's internal environment. These adjustments encompass a spectrum of modifications, including, but not limited to, the settings of the lighting system, audio output, infotainment system, seating configurations, and the like.

In some embodiments, the system may transmit specific instructions between various vehicle components to realize the desired user experience. For instance, based upon the time of day and potentially augmented by sleep data provided by the user, the AI model may determine settings that are to be set in the vehicle, and a software application associated therewith (e.g., an AI assistant, etc.) may dispatch commands to the lighting system to modulate brightness and color, thereby emulating the natural progression of daylight and promoting physiological responses conducive to either waking or winding down. As another example, the software application may send instructions to the audio system to curate a playlist or sound environment that aligns with the user's need for stimulation or relaxation. Similarly, adjustments to the infotainment system's display settings and content offerings may be made, ensuring that visual stimuli are in harmony with the user's circadian rhythm and current state of alertness.

Furthermore, the system may enhance physical comfort and safety during travel based on the time of day. For example, in response to sensor data indicating uneven road conditions, the AI model may determine changes to the vehicle's seat adjustment mechanisms. These commands are tailored to alter the seat's orientation, support level, and stability features, mitigating the discomfort and potential for movement induced by traversing irregular terrain. This aspect of the invention elevates the user's comfort and contributes to a safer driving experience by minimizing distractions and enabling the user to maintain optimal control over the vehicle.

In some embodiments, the system's responsiveness is further refined by integrating data, such as sleep data, allowing the AI model to ascertain the user's circadian rhythm and adjust the environment within the vehicle accordingly. This means that the system's definition of "time of day" is not a fixed hour but instead varies from one user to another based on their sleep patterns and lifestyle. Thus, the vehicle can offer a truly personalized experience. For example, 9 pm may be considered an early part of the evening for a user who typically retires late, whereas, for an early riser, the same time may signify the day's end. This nuanced approach ensures that the vehicle's environment is always in sync with the user's physiological and psychological state, enhancing their overall well-being and driving experience.

One of the benefits of the example embodiments is that it facilitates a user's transition into a state of increased alertness or relaxation, aligning with the commencement or conclusion of their day. In some embodiments, the method may include determining a state/condition associated with an individual in the vehicle. This state may be based on various factors, including but not limited to the individual's current physiological state, historical sleep data, or preferences set by the user. After determining the individual's condition, an AI model is executed that considers this state/condition alongside the current time of day. The AI model analyzes the provided data to make informed decisions about the most appropriate environmental settings within the vehicle.

Based on the outcome of the AI model's execution, a software application may identify specific settings on one or more systems within the vehicle that need adjustment. These systems can include, but are not limited to, the vehicle's lighting system, audio system, infotainment system, and seating configurations. This determination of which settings to change may promote alertness or relaxation, depending on the time of day and the individual's condition. Finally, the method culminates in changing the identified settings on one or more systems while the individual is in the vehicle. This step is facilitated through the dispatch of commands from the AI assistant to the various components of the vehicle. For example, instructions may be sent to the lighting system to adjust the brightness and color temperature to mimic the natural progression of daylight, enhancing physiological responses conducive to the desired state of the individual.

In some embodiments, commands could be issued to the audio system to curate a playlist or sound environment that aligns with the individual's need for stimulation or relaxation. Adjustments to the infotainment system and seating configurations are similarly enacted through directed messages from the AI assistant, ensuring that the vehicle's internal environment is optimally adjusted to support the individual's well-being. The individual's state/condition could be the individual's sleep data. The time of day could be morning, afternoon, night, and/or anytime within 24 hours. The condition could be determined by a server, sensors at a location, sensors in a vehicle, and/or various devices associated with the individual (watches, glasses, AR/VR headset, heart rate monitor, wireless phone, etc.). The person could be inside or outside the vehicle.

FIG. 1A illustrates a process 100A of receiving state data of an individual from a network outside of a vehicle according to example embodiments. Referring to FIG. 1A, an individual 102 may be present/located at a geographic location 120 outside of a vehicle 110, such as a real property (e.g., a home, office, etc.) which is associated with the vehicle 110. Here, the individual 102 may include a mobile device 104, one or more sensors 106 which are attached to the individual 102 or within an environment of the individual, and the like. The mobile device 104 and/or the one or more sensors 106 may capture sensor data of the individual 102 while within the location such as while the individual 102 is sleeping, awake, or the like, and transmit the sensor data to an application 111 (e.g., software application, etc.) installed on the vehicle 110. The instant solution may interact with application 111, wherein application 111 may fully or partially reside in vehicle 110 and/or in a remote database/server communicatively coupled to vehicle 110.

For example, the sensor data may include heart rate data measured of the individual 102 by a heart rate monitor throughout a twenty-four hour period, movement/acceleration data measured by an accelerometer or a gyroscope throughout a 24 hour period, or the like. The sensor data may be accumulated with data from multiple days thereby enabling a fuller understanding of the individual's habits. The application 111 may identify periods of the day when the individual 102 is usually asleep and when the individual is usually awake based on the data accumulated from the sensors 106, the mobile device 104, or the like. The mobile device 104, the sensors 106, and any other equipment within the geographic location 120 may be connected to a home network 122, such as a local area network (LAN) that is locally managed by a system at the geographic location 120. The mobile device 104, the sensors 106, and the like, may connect to the vehicle 110 via the home network 122 and the Internet, etc.

As another example, the individual 102 may provide their sleep data (e.g., when they are normally sleep) and when they are normally awake via user interface on the mobile device 104, such as a user interface of the application 111. The user inputs/preferences of sleep may be submitted from the mobile device 104 to the application 111 on the vehicle 110.

The application 111 may receive the sensor data and/or input data and determine a circadian rhythm/biological clock of the individual 102 based thereon. The circadian rhythm may include a cycle of data that identifies what parts of the day the individual 102 is normally asleep, awake, at their lowest body temperature, at their highest body temperature, at their fastest reaction time, at their greatest alertness, at their highest blood pressure, at their lowest body temperature, at their best coordination, and the like. The analyzed data including the sensor data, the input data, and the circadian rhythm data may be stored within a user profile of the individual 102 within a user profile 112 of the vehicle 110. The instant solution may send data to and/or obtain data from user profile 112, wherein the user profile 112 may be located in vehicle 110 or communicatively coupled to vehicle 110, such as in a remote database/server.

Here, the user profile stored within the user profile 112 may include the sensor data (sleep data of the individual 102), the input data input by the individual 102 via the mobile device 104 which describes their sleep preferences, the identified state/condition of the individual 102 such as their circadian rhythm, biological clock, and the like.

Figure 1B:
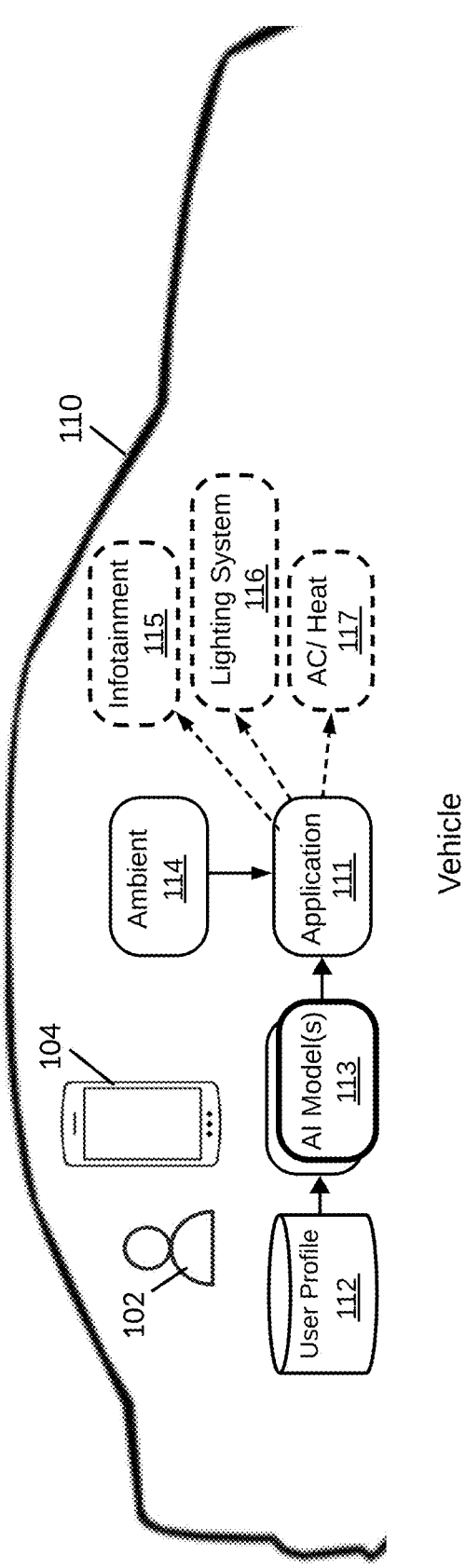
FIG. 1B is a diagram illustrating a process of dynamically adjusting one or more systems within the vehicle based on the state of the individual and a current time of day according to example embodiments.

FIG. 1B illustrates a process 100B of dynamically adjusting one or more systems within the vehicle 110 based on the state of the individual 102 and a current time of day according to example embodiments. Referring to FIG. 1B, the individual 102 has now entered the vehicle 110. The individual 102 may be determined to be located in the vehicle 110 by the application 111 based on a key used by the individual 102 to turn on the engine, a pairing of the mobile device 104 with an infotainment system 115, or the like.

In response, the application 111 may retrieve the user profile data of the individual 102 from the user profile 112. In addition, the application 111 may determine a current time of day, for example, based on a system clock within the vehicle 110 (such as within a computer of the vehicle, etc.) As another example, the application 111 may determine the current time of day based on an ambient light sensor 114 which can sense a current amount of light present in the ambient environment around the vehicle 110. Here, the application 111 may execute one or more artificial intelligence (AI) models 113 on the user profile data and the current time of day to determine one or more optimal settings of one or more systems within the vehicle. The one or more optimal settings may be optimized based on the user's circadian rhythm.

According to various embodiments, the one or more AI models 113 may determine a type of content such as audio to be output by the infotainment system 115 based on the user profile and the current time of day. The type of audio content to play may be based on a level of alertness of the individual 102 at the current time of day. If the individual 102 is normally refreshed and awake at the time, the audio may include music that keeps the user alert and happy such as music that is upbeat. As another example, if the user is about to go to sleep or is at the end of their day, the audio may include music that keeps the user relaxed.

The output of the one or more AI models 113 may be provided to the application 111. In response to receiving the output from the one or more AI models 113, the application 111 may identify a playlist or a song that corresponds to the type of audio and send a message to the infotainment system 115 with instructions to play the playlist/song.

As another example, the one or more AI models 113 may determine a light setting within the vehicle 110 such as a dimness, a color, and the like, based on the current time of day and the circadian rhythm of the individual 102. For example, if the user is just waking up or is on their way to work in the morning, the one or more AI models 113 may determine that the light should be bright colored/orange, and should be brightly displayed within the vehicle 110. As another example, if the user is close to bedtime, the one or more AI models may determine that the light should be dimly displayed, blue or purple in color, or the like.

As another example, the one or more AI models 113 may determine a temperature setting based on the current time of day and the circadian rhythm. For example, if the user is at their warmest point of the day, the one or more AI models 113 may determine to turn on the air conditioning to a particular temperature or roll down the windows. As another example, if the user is at their coldest point in the day, the one or more AI models 113 may determine to add heat into the interior of the vehicle 110.

The output by the one or more AI models 113 may be sent to the application 111. In response, the application 111 may send messages to one or more of the infotainment system 115, a lighting system 116, an air conditioning/heating system 117, a seat (not shown), or the like, with instructions to modify the settings to a particular value.

For example, the output of the one or more AI models 113 may cause the application 111 to identify specific settings on one or more systems within the vehicle that need adjustment. These systems can include, but are not limited to, the vehicle's lighting system, audio system/infotainment system, temperature controls, seating configurations, and the like. This determination of which settings to change may promote alertness or relaxation, depending on the time of day and the individual's state. The application 111 changes the identified settings on one or more systems while the individual 102 is in the vehicle. This step is facilitated through the dispatch of commands from the application 111 to the various components of the vehicle 110.

For example, instructions may be sent to the lighting system 116 to adjust the brightness and color temperature to mimic the natural progression of daylight, enhancing physiological responses conducive to the desired state of the individual. As another example, commands could be issued to the infotainment system 115 to curate a playlist or sound environment that aligns with the individual's need for stimulation or relaxation. As another example, temperature settings may be sent to the air conditioning/heating system 117, and the like. As another example, seating configurations may be modified. The adjustments to the interior atmosphere of the vehicle 110 may ensure that the vehicle's internal environment is optimally adjusted to support the individual's well-being.

In the example embodiments, the application 111 may set an initial setting of a system within the vehicle 110 when the vehicle is started/turned on. Here, the application 111 may issue an instruction to set a value of one or more of the infotainment system 115, the lighting system 116, the air conditioning/heating system 117, a seat, and the like, within a predetermined amount of time of the vehicle 110 being turned on, for example, within 5 seconds, 10 seconds, 30 seconds, or the like, of the ignition of the vehicle 110 being turned on. Also, the application 111 may display a notification on a display system within the vehicle, such as a display system of the infotainment system 115 which notifies the individual 102 (and any other occupants, etc.) that the vehicle 110 is being automatically tuned.

For example, based on the instructions from the one or more AI models 113, the application 111 may set the infotainment system 115 to a particular song/audio content, may set the lighting system 116 to a particular color value, a particular brightness value, or the like, may set the air conditioning/heating system 117 to a particular temperature value, and the like. As another example, the application 111 may set one or more of a seat position, an arm rest position, a mirror position, or the like, to a particular position.

Figure 1C:
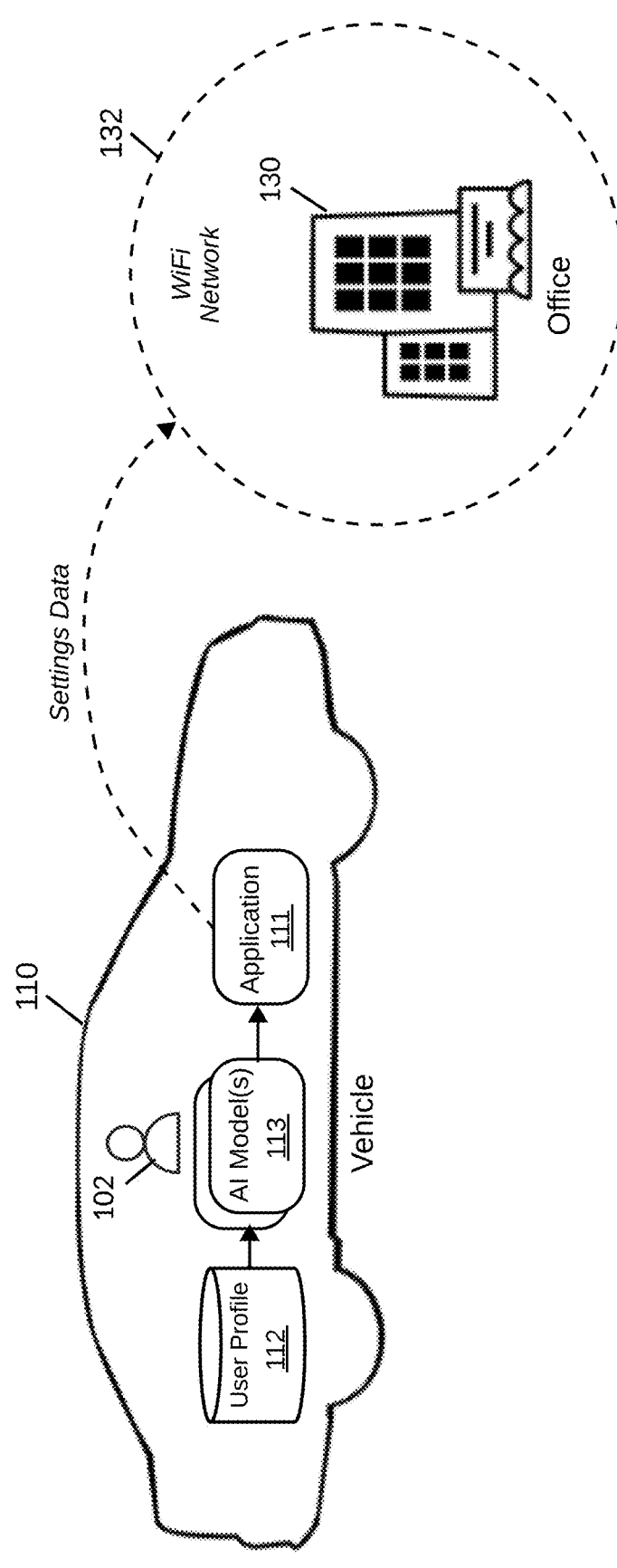
FIG. 1C is a diagram illustrating a process of providing state data of the individual and settings of the vehicle to a next location of the individual according to example embodiments.

FIG. 1C illustrates a process 100C of providing state data of the individual 102 and settings of the vehicle 110 to a next location of the individual according to example embodiments. Referring to FIG. 1C, the individual 102 may provide a destination of the vehicle 110 when the individual 102 is preparing for a ride or has already entered the vehicle 110 and has turned on the ignition. For example, the individual 102 may input a destination of the vehicle 110 into a mobile application on the mobile device 104 (FIG. 1A). As another example, the individual 102 may input the destination into a navigation system, the infotainment system 115, or the like. As another example, the vehicle 110 may include determine the destination based on execution of the one or more AI models 113 and historical driving data/behavior of the vehicle 110.

In this example, the destination is a geographic location 130 that corresponds to a work environment of the individual 102. Here, the application 111 may forward the vehicle settings tuned by the application 111 to a computing node at the geographic location 130, such as a server, a computer, or the like, which is connected to the application via a network 132, the Internet, a combination of networks, and the like. By forwarding the vehicle settings data to the geographic location 130, a system there may automatically tune settings within an environment of the geographic location 130 to relax the individual 102 when the individual 102 enters the geographic location 130.

Figure 1D:
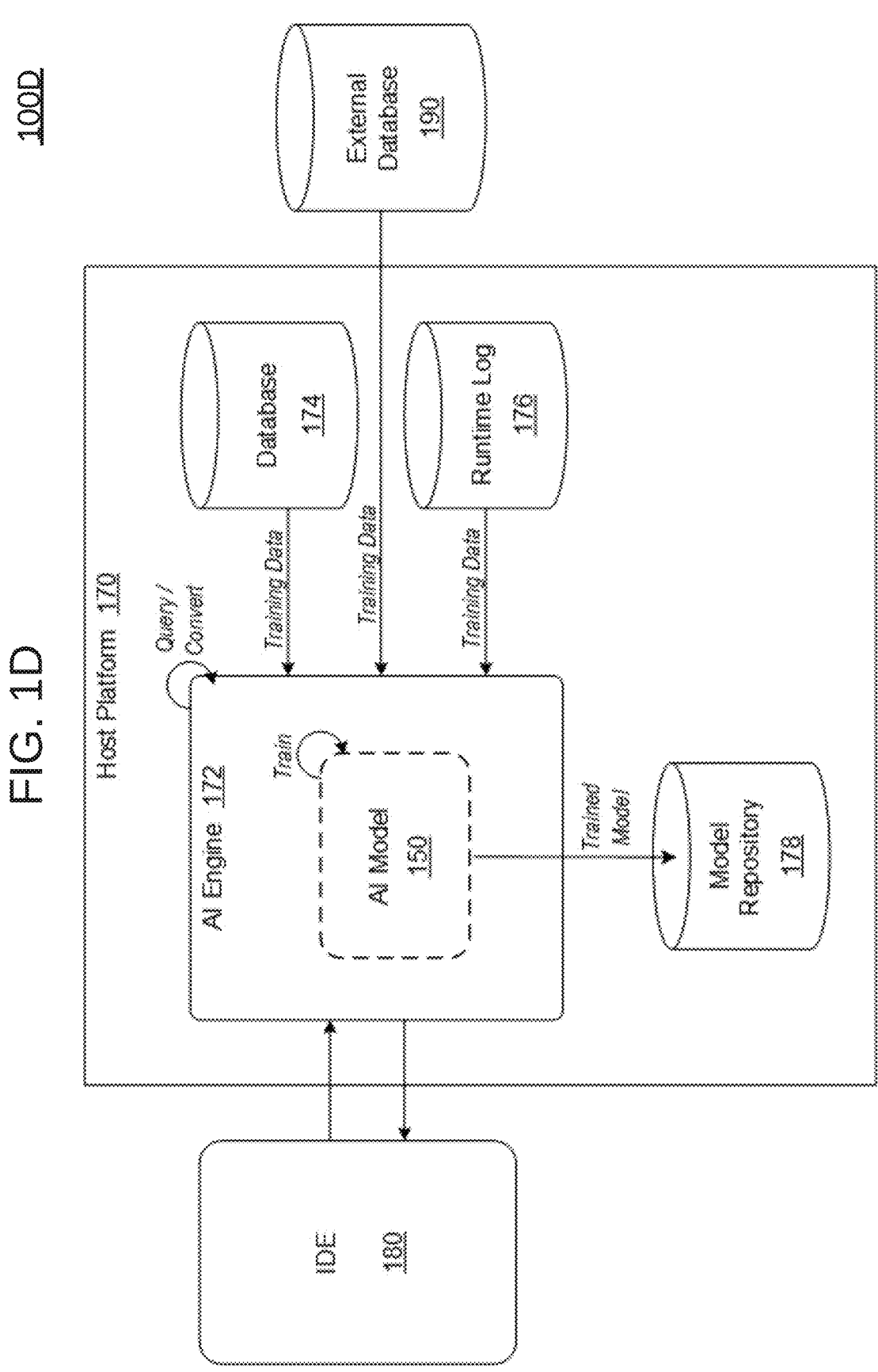
FIG. 1D is a diagram illustrating a process of training an AI model according to example embodiments.

FIG. 1D illustrates a process 100D of training the AI model 150 according to example embodiments. As an example, the AI model 150 may correspond to the AI model shown and described with respect to FIGS. 1A-1C. However, it should be appreciated that the process 100D shown in FIG. 1D is also applicable to other types of models such as machine learning models, statistical models, and the like. Referring to FIG. 1D, a host platform 170 may host an IDE 180 (integrated development environment) where models may be developed, trained, retrained, and the like. In this example, the IDE 180 may include a software application with a user interface accessible by a user device (not shown) over a network or through a local connection. For example, the IDE 180 may be embodied as a web application that can be accessed at a network address, URL, etc by a device. As another example, the IDE 180 may be locally or remotely installed on a computing device where it is accessed and used locally.

The IDE 180 may be used to design the AI model 150 (via a user interface of the IDE 180) that can receive sleep data, time of day data, circadian rhythm data, ambient light data, vehicle settings data, and the like, and generate a trained AI model. The model can be executed/trained based on the training data established via the user interface. For example, the user interface may be used to build a new model. The training data for training such a new model may be provided from training data stored in a database 174 which includes training samples (e.g., recommended vehicle settings for a particular time of day and a particular sleep pattern/circadian rhythm.) As another example, the training data may include training data may be pulled from one or more external data stores or external databases 190 such as publicly available sites, etc.

During training, the AI model 150 may be executed on the training data via an AI engine 172 of the host platform 170. Through the executing, the AI model 150 may learn how to recommend vehicle settings for a particular type of circadian rhythm and a current time of the day or an amount of daylight available. When the model is fully trained, it may be stored within the model repository 178 via the IDE 180, or the like.

As another example, the IDE 180 may be used to retrain the AI model 150 after the model has already been deployed. The retraining process may use executional results that have already been generated/output by the AI model 150 in a live environment (including any user feedback, etc.) to retrain the AI model 150. For example, a user may provide feedback on recommended vehicular settings proposed by the AI model for a particular time of day including, but not limited to, infotainment system settings, lighting settings, audio content settings, seat position settings, and the like. This data may be captured and stored within a runtime log 176 or other data store within the live environment.

Flow diagrams depicted herein, such as FIG. 2C, FIG. 2D, FIG. 2E, and FIG. 2F, are separate examples but may be the same or different embodiments. Any of the operations in one flow diagram may be adopted and shared with another flow diagram. No example operation is intended to limit the subject matter of any embodiment or corresponding claim.

It is important to note that all the flow diagrams and corresponding processes derived from FIG. 2C, FIG. 2D, FIG. 2E, and FIG. 2F may be part of a same process or may share sub-processes with one another thus making the diagrams combinable into a single preferred embodiment that does not require any one specific operation but which performs certain operations from one example process and from one or more additional processes. All the example processes are related to the same physical system and can be used separately or interchangeably.

The instant solution can be used in conjunction with one or more types of vehicles: battery electric vehicles, hybrid vehicles, fuel cell vehicles, internal combustion engine vehicles and/or vehicles utilizing renewable sources.

Figure 2A:
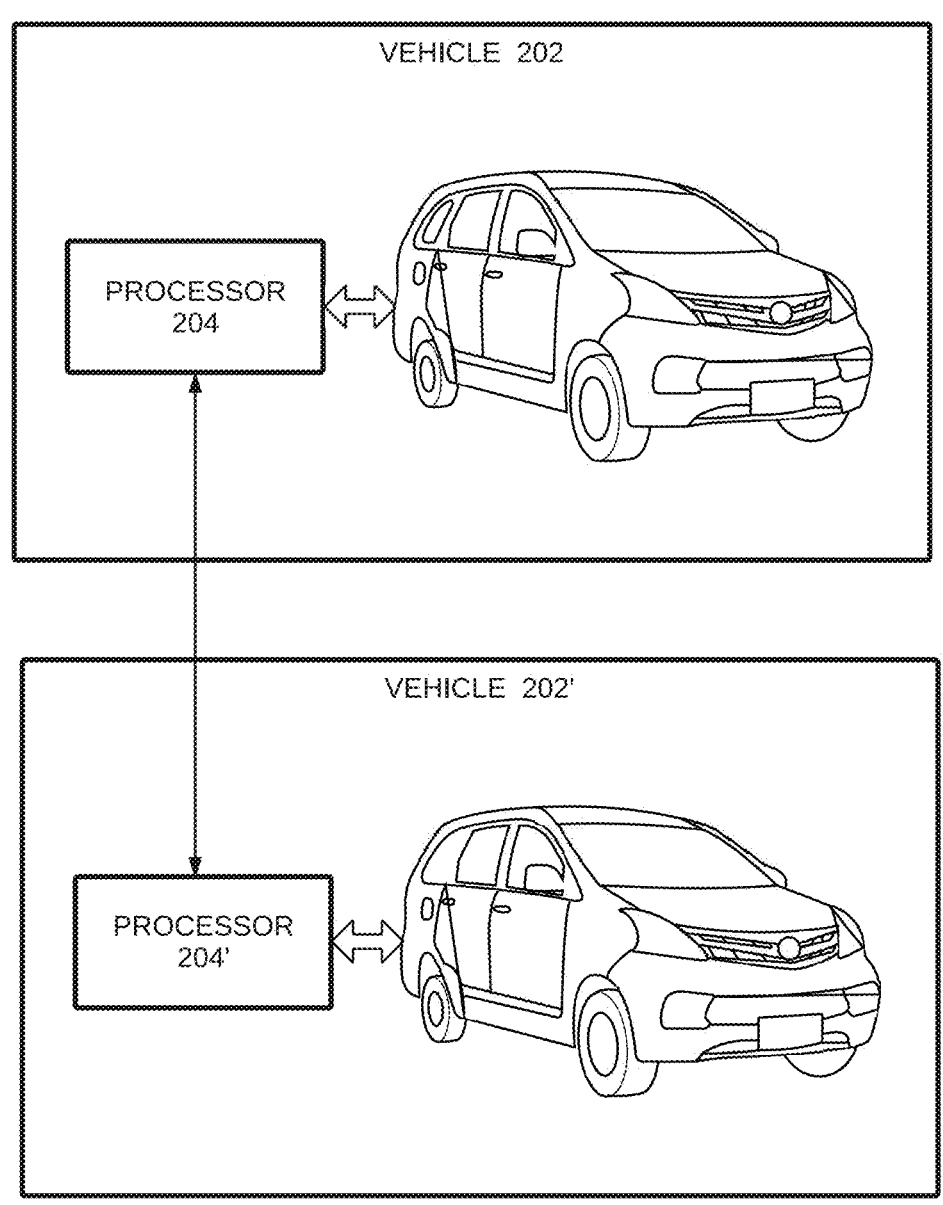
FIG. 2A illustrates a vehicle network diagram, according to example embodiments.

FIG. 2A illustrates a vehicle network diagram 200, according to example embodiments. The network comprises elements including a vehicle 202 including a processor 204, as well as a vehicle 202' including a processor 204'. The vehicles 202, 202' communicate with one another via the processors 204, 204', as well as other elements (not shown) including transceivers, transmitters, receivers, storage, sensors, and other elements capable of providing communication. The communication between the vehicles 202, and 202' can occur directly, via a private and/or a public network (not shown), or via other vehicles and elements comprising one or more of a processor, memory, and software. Although depicted as single vehicles and processors, a plurality of vehicles and processors may be present. One or more of the applications, features, steps, solutions, etc., described and/or depicted herein may be utilized and/or provided by the instant elements.

Figure 2B:
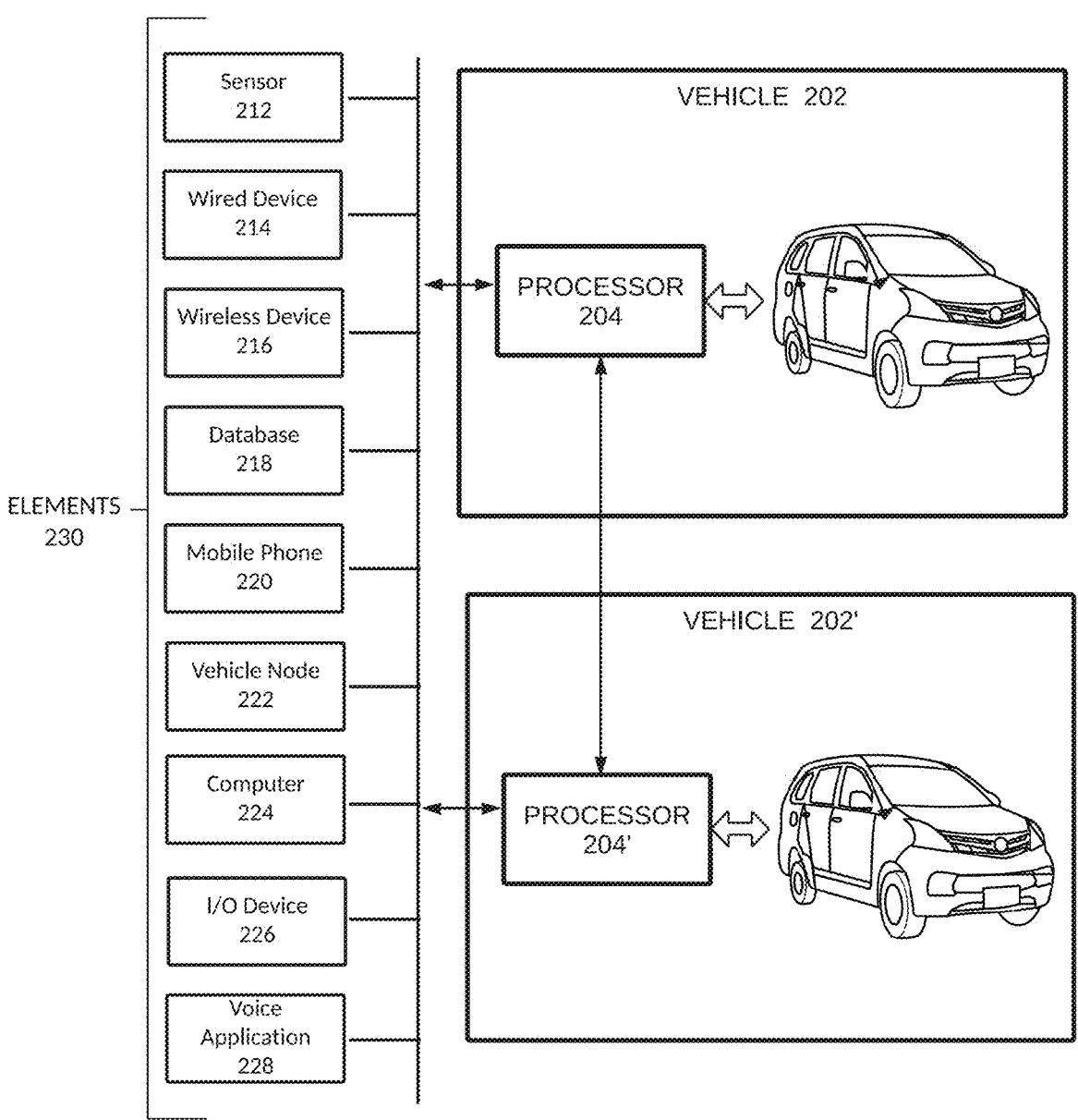
FIG. 2B illustrates another vehicle network diagram, according to example embodiments.

FIG. 2B illustrates another vehicle network diagram 210, according to example embodiments. The network comprises elements including a vehicle 202 including a processor 204, as well as a vehicle 202' including a processor 204'. The vehicles 202, 202' communicate with one another via the processors 204, 204', as well as other elements (not shown), including transceivers, transmitters, receivers, storage, sensors, and other elements capable of providing communication. The communication between the vehicles 202, and 202' can occur directly, via a private and/or a public network (not shown), or via other vehicles and elements comprising one or more of a processor, memory, and software. The processors 204, 204' can further communicate with one or more elements 230 including sensor 212, wired device 214, wireless device 216, database 218, mobile phone 220, vehicle node 222, computer 224, input/output (I/O) device 226, and voice application 228. The processors 204, 204' can further communicate with elements comprising one or more of a processor, memory, and software.

Although depicted as single vehicles, processors and elements, a plurality of vehicles, processors and elements may be present. Information or communication can occur to and/or from any of the processors 204, 204' and elements 230. For example, the mobile phone 220 may provide information to the processor 204, which may initiate the vehicle 202 to take an action, may further provide the information or additional information to the processor 204', which may initiate the vehicle 202' to take an action, may further provide the information or additional information to the mobile phone 220, the vehicle node 222, and/or the computer 224. One or more of the applications, features, steps, solutions, etc., described and/or depicted herein may be utilized and/or provided by the instant elements.

Figure 2C:
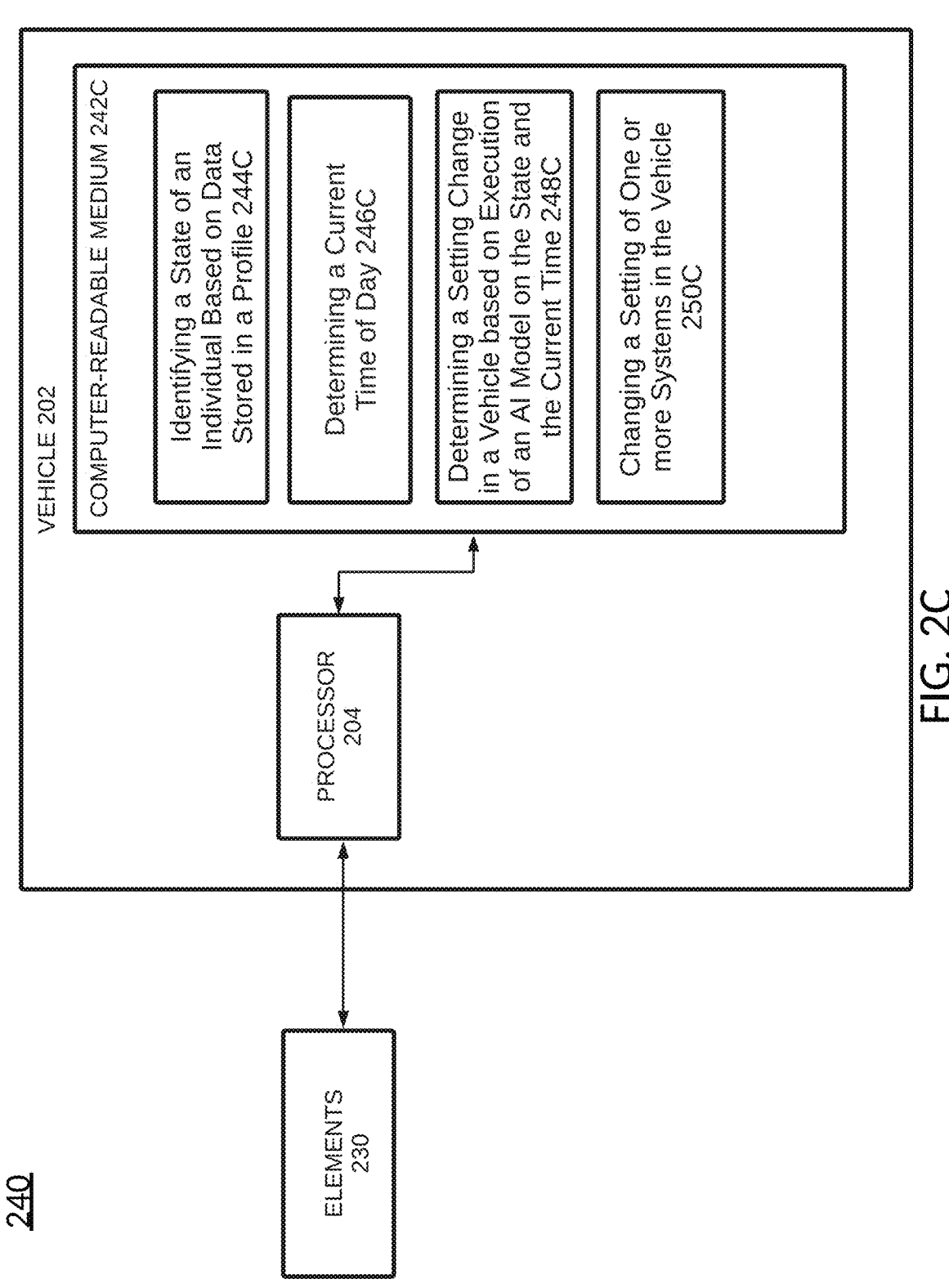
FIG. 2C illustrates yet another vehicle network diagram, according to example embodiments.

FIG. 2C illustrates yet another vehicle network diagram 240, according to example embodiments. The network comprises elements including a vehicle 202, a processor 204, and a non-transitory computer-readable medium 242C. The processor 204 is communicably coupled to the computer-readable medium 242C and elements 230 (which were depicted in FIG. 2B). The vehicle 202 may be a vehicle, server, or any device with a processor and memory.

The processor 204 performs one or more of identifying a state of an individual associated with a vehicle based on data of the individual stored in a profile in 244C, determining a current time of day from a system of the vehicle in 246C, determining a setting to change on one or more systems within the vehicle based on execution of an artificial intelligence (AI) model on the state of the individual and the current time of day in 248C, and changing the setting on the one or more systems within the vehicle while the individual is within the vehicle in 250C.

Figure 2D:
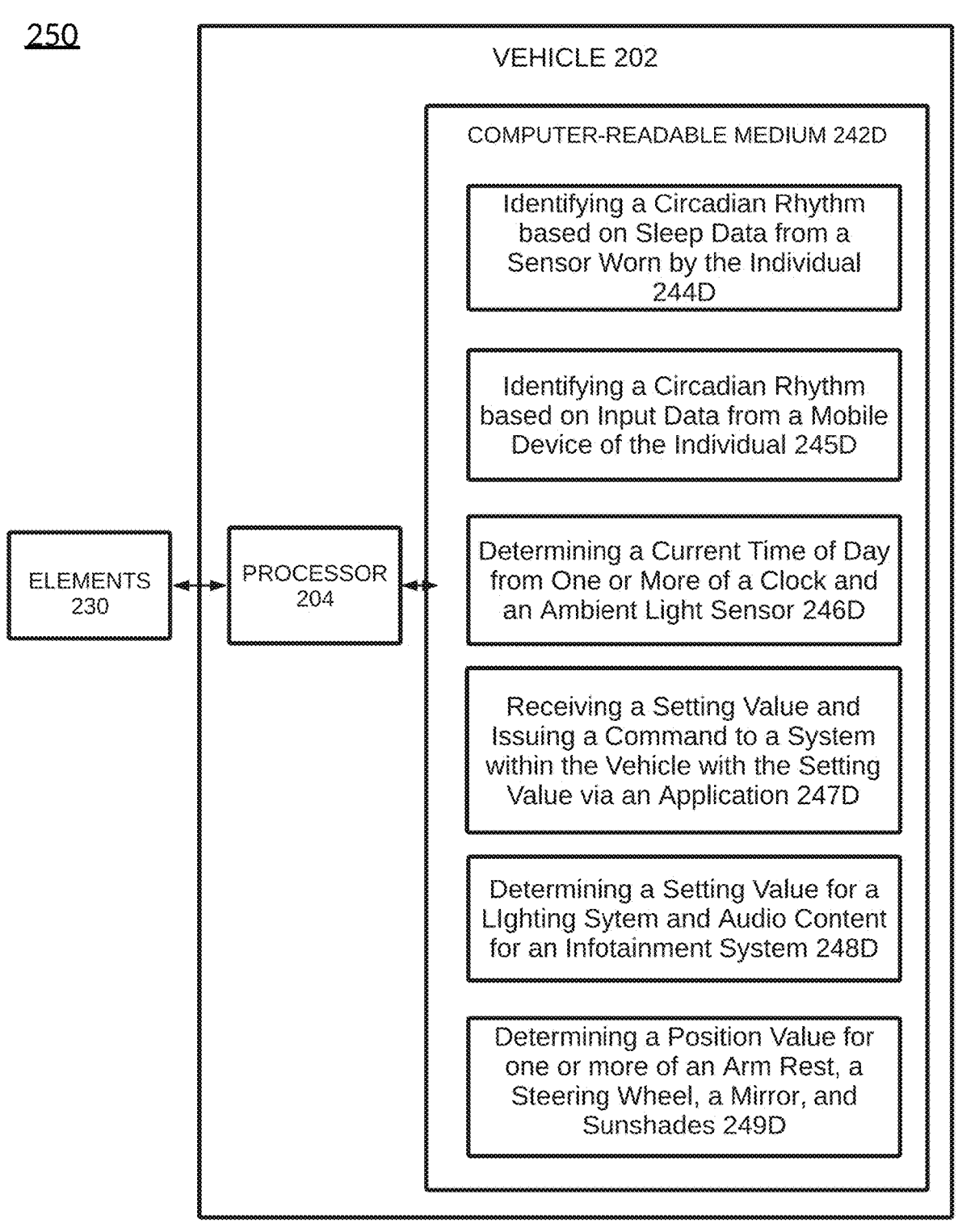
FIG. 2D illustrates a further vehicle network diagram, according to example embodiments.

FIG. 2D illustrates a further vehicle network diagram 250, according to example embodiments. The network comprises elements including a vehicle 202, a processor 204, and a non-transitory computer-readable medium 242D. The processor 204 is communicably coupled to the computer-readable medium 242D and elements 230 (which were depicted in FIG. 2B). The vehicle 202 may be a vehicle, server or any device with a processor and memory.

The processor 204 performs one or more of receiving sleep data of the individual from one or more sensors worn by the individual while the individual is outside of the vehicle, storing the sleep data in the profile, and identifying a circadian rhythm of the individual based on the sleep data in 244D, receiving input data from a mobile device of the individual which includes sleep preferences of the individual and storing the sleep preferences in the profile, and identifying a circadian rhythm of the individual based on the sleep preferences of the individual in 245D, determining the current time of day comprises determining the current time of day based on one or more of a system clock of the vehicle and an ambient light sensor of the vehicle in 246D, receiving a setting value for a system from among the one or more systems within the vehicle from the AI model via a software application installed within the vehicle, and issuing commands to the system within the vehicle to apply the setting value to the system in 247D, determining a setting value for a lighting system within an interior of the vehicle and audio content to be output by an infotainment system within the vehicle based on execution of the AI model on the state of the individual and the current time of day in 248D, and determining a position value for one or more of a steering wheel position, an arm rest position, mirror position, and sunshades, based on execution of the AI model the state of the individual and the current time of day in 249D.

While this example describes in detail only one vehicle 202, multiple such nodes may be connected to the blockchain. It should be understood that the vehicle 202 may include additional components and that some of the components described herein may be removed and/or modified without departing from a scope of the instant application. The vehicle 202 may have a computing device or a server computer, or the like, and may include a processor 204, which may be a semiconductor-based microprocessor, a central processing unit (CPU), an application-specific integrated circuit (ASIC), a field-programmable gate array (FPGA), and/or another hardware device. Although a single processor 204 is depicted, it should be understood that the vehicle 202 may include multiple processors, multiple cores, or the like without departing from the scope of the instant application. The vehicle 202 may be a vehicle, server or any device with a processor and memory.

The processor 204 performs one or more of receiving a confirmation of an event from one or more elements described or depicted herein, wherein the confirmation comprises a blockchain consensus between peers represented by any of the elements and executing a smart contract to record the confirmation on the blockchain consensus. Consensus is formed between one or more of any element 230 and/or any element described or depicted herein, including a vehicle, a server, a wireless device, etc. In another example, the vehicle 202 can be one or more of any element 230 and/or any element described or depicted herein, including a server, a wireless device, etc.

The processors and/or computer-readable medium may fully or partially reside in the interior or exterior of the vehicles. The steps or features stored in the computer-readable medium may be fully or partially performed by any of the processors and/or elements in any order. Additionally, one or more steps or features may be added, omitted, combined, performed at a later time, etc.

Figure 2E:
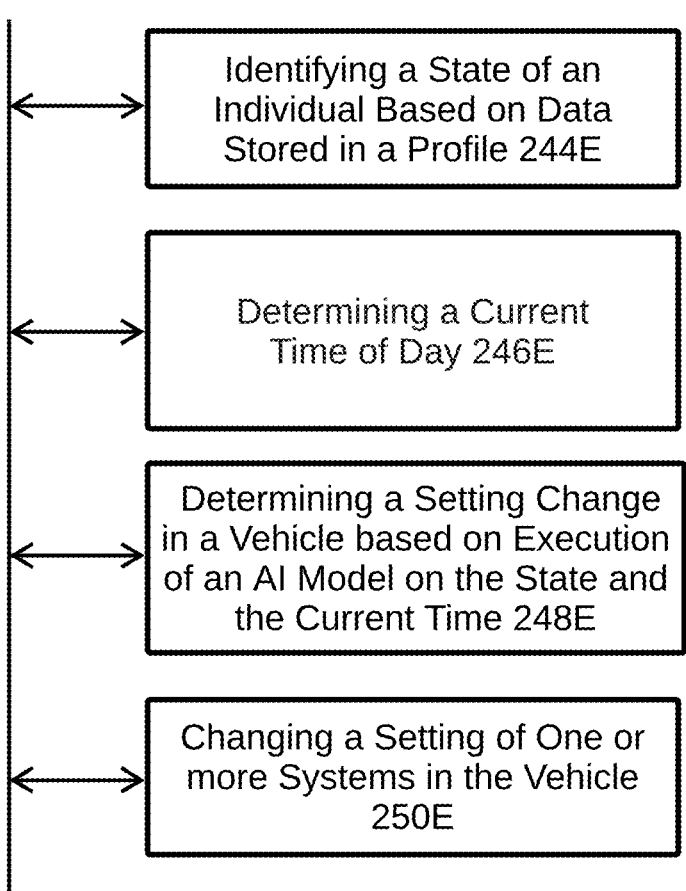
FIG. 2E illustrates a flow diagram, according to example embodiments.

FIG. 2E illustrates a flow diagram 260, according to example embodiments. Referring to FIG. 2E, the instant solution includes one or more of identifying a state of an individual associated with a vehicle based on data of the individual stored in a profile in 244E, determining a current time of day from a system of the vehicle in 246E, determining a setting to change on one or more systems within the vehicle based on execution of an artificial intelligence (AI) model on the state of the individual and the current time of day in 248E, and changing the setting on the one or more systems within the vehicle while the individual is within the vehicle in 250E.

Figure 2F:
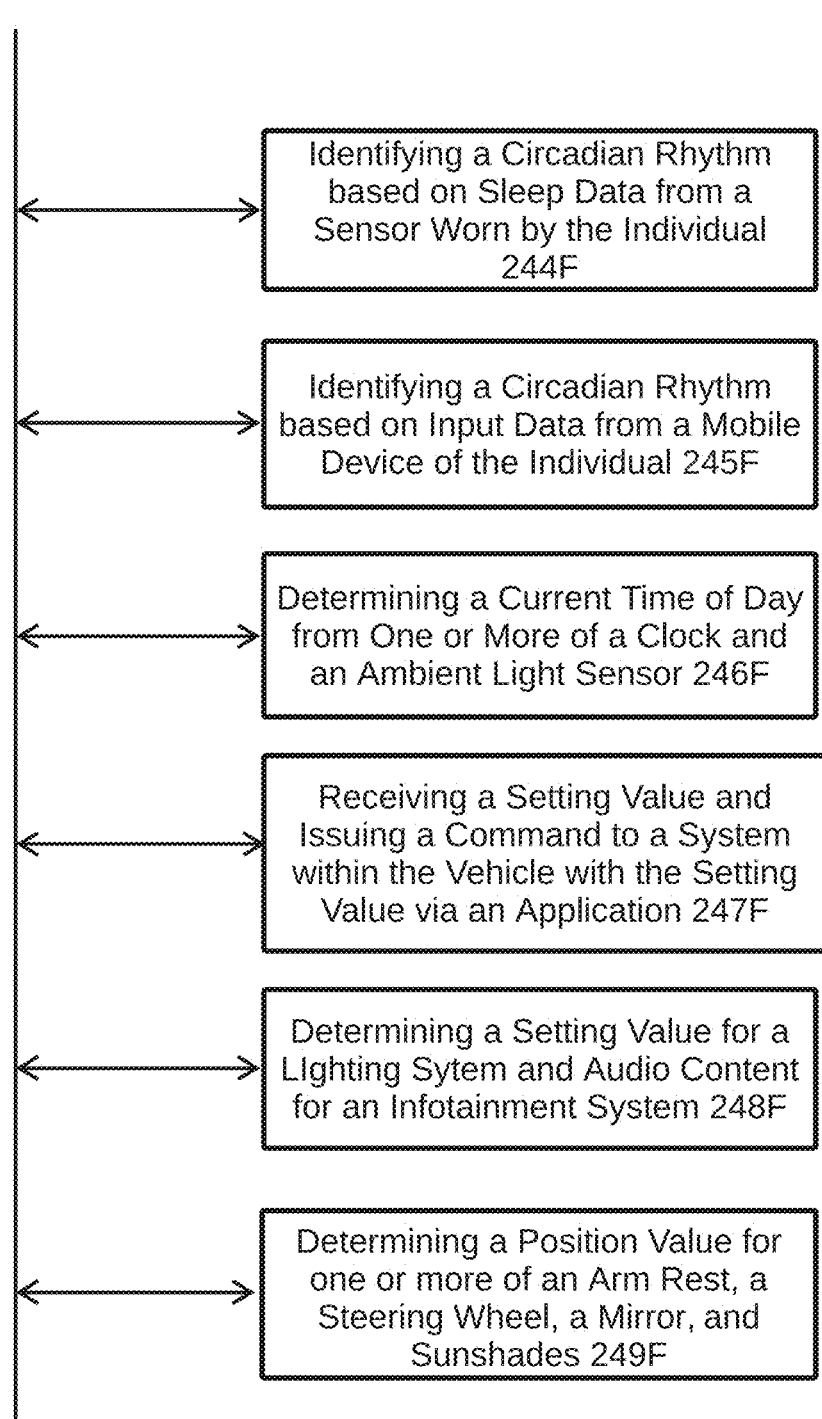
FIG. 2F illustrates another flow diagram, according to example embodiments.

FIG. 2F illustrates another flow diagram 270, according to example embodiments. Referring to FIG. 2F, the instant solution includes one or more of receiving sleep data of the individual from one or more sensors worn by the individual while the individual is outside of the vehicle, storing the sleep data in the profile, and identifying a circadian rhythm of the individual based on the sleep data in 244F, receiving input data from a mobile device of the individual which includes sleep preferences of the individual and storing the sleep preferences in the profile, and identifying a circadian rhythm of the individual based on the sleep preferences of the individual in 245F, determining the current time of day comprises determining the current time of day based on one or more of a system clock of the vehicle and an ambient light sensor of the vehicle in 246F, receiving a setting value for a system from among the one or more systems within the vehicle from the AI model via a software application installed within the vehicle, and issuing commands to the system within the vehicle to apply the setting value to the system in 247F, determining a setting value for a lighting system within an interior of the vehicle and audio content to be output by an infotainment system within the vehicle based on execution of the AI model on the state of the individual and the current time of day in 248F, and determining a position value for one or more of a steering wheel position, an arm rest position, mirror position, and sunshades, based on execution of the AI model the state of the individual and the current time of day in 249F.

Technological advancements typically build upon the fundamentals of predecessor technologies; such is the case with Artificial Intelligence (AI) models. An AI classification system describes the stages of AI progression. The first classification is known as "Reactive Machines," followed by present-day AI classification "Limited Memory Machines" (also known as "Artificial Narrow Intelligence"), then progressing to "Theory of Mind" (also known as "Artificial General Intelligence"), and reaching the AI classification "Self-Aware" (also known as "Artificial Superintelligence"). Present-day Limited Memory Machines are a growing group of AI models built upon the foundation of its predecessor, Reactive Machines. Reactive Machines emulate human responses to stimuli; however, they are limited in their capabilities as they cannot typically learn from prior experience. Once the AI model's learning abilities emerged, its classification was promoted to Limited Memory Machines. In this present-day classification, AI models learn from large volumes of data, detect patterns, solve problems, generate and predict data, and the like, while inheriting all of the capabilities of Reactive Machines. Examples of AI models classified as Limited Memory Machines include, but are not limited to, Chatbots, Virtual Assistants, Machine Learning (ML), Deep Learning (DL), Natural Language Processing (NLP), Generative AI (GenAI) models, and any future AI models that are yet to be developed possessing characteristics of Limited Memory Machines. Generative AI models combine Limited Memory Machine technologies, incorporating ML and DL, forming the foundational building blocks of future AI models. For example, Theory of Mind is the next progression of AI that may be able to perceive, connect, and react by generating appropriate reactions in response to an entity with which the AI model is interacting; all of these capabilities rely on the fundamentals of Generative AI. Furthermore, in an evolution into the Self-Aware classification, AI models will be able to understand and evoke emotions in the entities they interact with, as well as possessing their own emotions, beliefs, and needs, all of which rely on the Generative AI fundamentals of learning from experiences to generate and draw conclusions about itself and its surroundings. Generative AI models are integral and core to future artificial intelligence models. As described herein, Generative AI refers to present-day Generative AI models and future AI models.

Figure 3A:
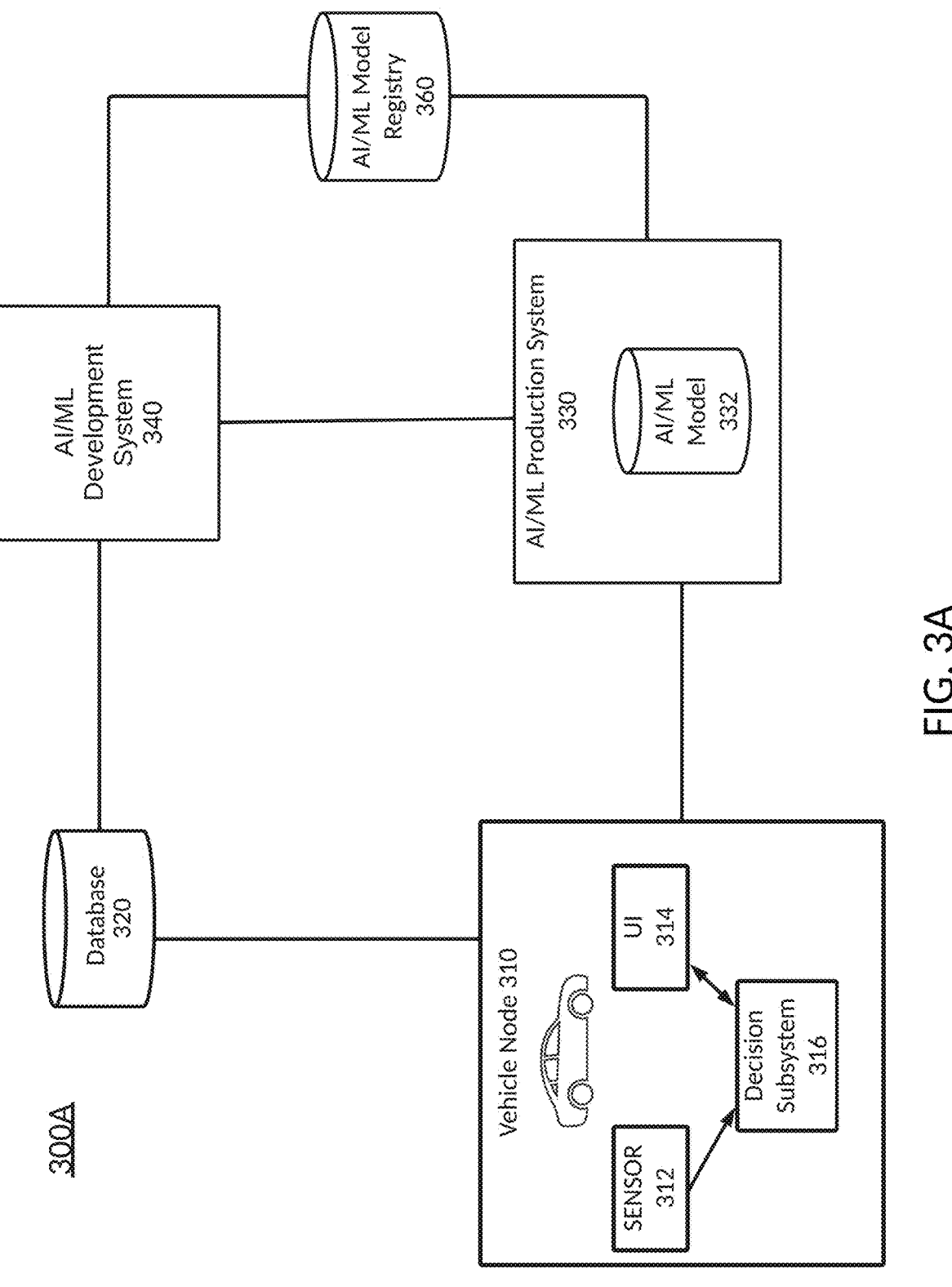
FIG. 3A illustrates an Artificial Intelligence (AI)/Machine Learning (ML) network diagram for integrating an artificial intelligence (AI) model into any decision point in the example embodiments.

FIG. 3A illustrates an AI/ML network diagram 300A that supports AI-assisted vehicle or occupant decision points. Other branches of AI, such as, but not limited to, computer vision, fuzzy logic, expert systems, neural networks/deep learning, generative AI, and natural language processing, may all be employed in developing the AI model shown in these embodiments. Further, the AI model included in these embodiments is not limited to a particular AI algorithm. Any algorithm or combination of algorithms related to supervised, unsupervised, and reinforcement learning algorithms may be employed.

In one embodiment, Generative AI (GenAI) may be used by the instant solution in the transformation of data. Vehicles are equipped with diverse sensors, cameras, radars, and LIDARs, which collect a vast array of data, such as images, speed readings, GPS data, and acceleration metrics. However, raw data, once acquired, undergoes preprocessing that may involve normalization, anonymization, missing value imputation, or noise reduction to allow the data to be further used effectively.

The GenAI executes data augmentation following the preprocessing of the data. Due to the limitation of datasets in capturing the vast complexity of real-world vehicle scenarios, augmentation tools are employed to expand the dataset. This might involve image-specific transformations like rotations, translations, or brightness adjustments. For non-image data, techniques like jittering can be used to introduce synthetic noise, simulating a broader set of conditions.

In the instant solution, data generation is then performed on the data. Tools like Generative Adversarial Networks (GANs) and Variational Autoencoders (VAEs) are trained on existing datasets to generate new, plausible data samples. For example, GANs might be tasked with crafting images showcasing vehicles in uncharted conditions or from unique perspectives. As another example, the synthesis of sensor data may be performed to model and create synthetic readings for such scenarios, enabling thorough system testing without actual physical encounters. A critical step in the use of GenAI, given the safety-critical nature of vehicles, is validation. This validation might include the output data being compared with real-world datasets or using specialized tools like a GAN discriminator to gauge the realism of the crafted samples.

Vehicle node 310 may include a plurality of sensors 312 that may include but are not limited to, light sensors, weight sensors, cameras, lidar, and radar. In some embodiments, these sensors 312 send data to a database 320 that stores data about the vehicle and occupants of the vehicle. In some embodiments, these sensors 312 send data to one or more decision subsystems 316 in vehicle node 310 to assist in decision-making.

Vehicle node 310 may include one or more user interfaces (UIs) 314, such as a steering wheel, navigation controls, audio/video controls, temperature controls, etc. In some embodiments, these UIs 314 send data to a database 320 that stores event data about the UIs 314 that includes but is not limited to selection, state, and display data. In some embodiments, these UIs 314 send data to one or more decision subsystems 316 in vehicle node 310 to assist decision-making.

Vehicle node 310 may include one or more decision subsystems 316 that drive a decision-making process around, but are not limited to, vehicle control, temperature control, charging control, etc. In some embodiments, the decision subsystems 316 gather data from one or more sensors 312 to aid in the decision-making process. In some embodiments, a decision subsystem 316 may gather data from one or more UIs 314 to aid in the decision-making process. In some embodiments, a decision subsystem 316 may provide feedback to a UI 314.

An AI/ML production system 330 may be used by a decision subsystem 316 in a vehicle node 310 to assist in its decision-making process. The AI/ML production system 330 includes one or more AI/ML models 332 that are executed to retrieve the needed data, such as, but not limited to, a prediction, a categorization, a UI prompt, etc. In some embodiments, an AI/ML production system 330 is hosted on a server. In some embodiments, the AI/ML production system 330 is cloud-hosted. In some embodiments, the AI/ML production system 330 is deployed in a distributed multi-node architecture. In some embodiments, the AI production system resides in vehicle node 310.

An AI/ML development system 340 creates one or more AI/ML models 332. In some embodiments, the AI/ML development system 340 utilizes data in the database 320 to develop and train one or more AI models 332. In some embodiments, the AI/ML development system 340 utilizes feedback data from one or more AI/ML production systems 330 for new model development and/or existing model re-training. In an embodiment, the AI/ML development system 340 resides and executes on a server. In another embodiment the AI/ML development system 340 is cloud-hosted. In a further embodiment, the AI/ML development system 340 utilizes a distributed data pipeline/analytics engine.

Once an AI/ML model 332 has been trained and validated in the AI/ML development system 340, it may be stored in an AI/ML model registry 360 for retrieval by either the AI/ML development system 340 or by one or more AI/ML production systems 330. The AI/ML model registry 360 resides in a dedicated server in one embodiment. In some embodiments, the AI/ML model registry 360 is cloud-hosted. The AI/ML model registry 360 is a distributed database in other embodiments. In further embodiments, the AI/ML model registry 360 resides in the AI/ML production system 330.

Figure 3B:
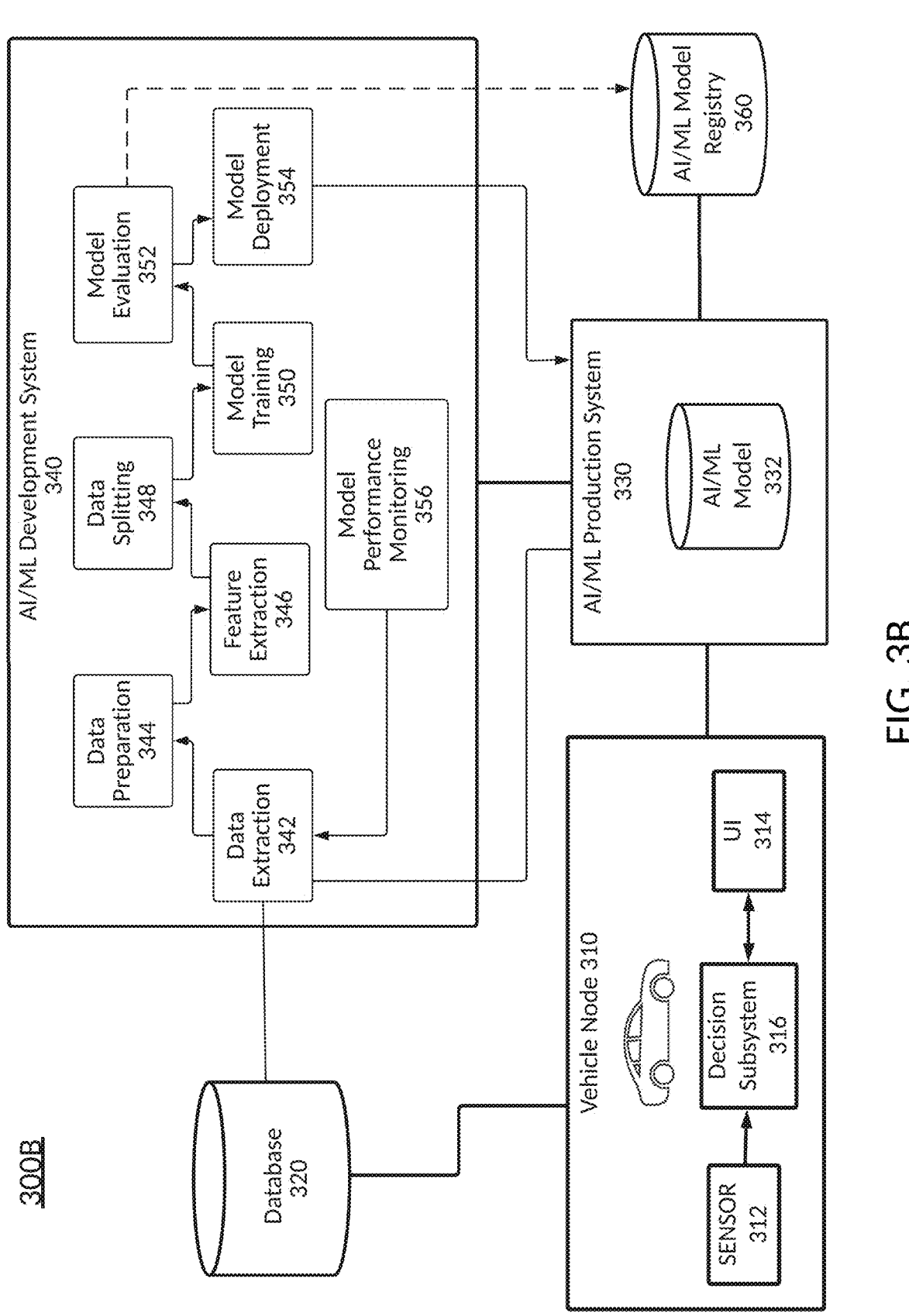
FIG. 3B illustrates a process for developing an Artificial Intelligence (AI)/Machine Learning (ML) model that supports AI-assisted vehicle or occupant decision points.

FIG. 3B illustrates a process 300B for developing one or more AI/ML models that support AI-assisted vehicle or occupant decision points. An AI/ML development system 340 executes steps to develop an AI/ML model 332 that begins with data extraction 342, in which data is loaded and ingested from one or more data sources. In some embodiments, vehicle and user data is extracted from a database 320. In some embodiments, model feedback data is extracted from one or more AI/ML production systems 330.

Once the required data has been extracted 342, it must be prepared 344 for model training. In some embodiments, this step involves statistical testing of the data to see how well it reflects real-world events, its distribution, the variety of data in the dataset, etc. In some embodiments, the results of this statistical testing may lead to one or more data transformations being employed to normalize one or more values in the dataset. In some embodiments, this step includes cleaning data deemed to be noisy. A noisy dataset includes values that do not contribute to the training, such as but not limited to, null and long string values. Data preparation 344 may be a manual process or an automated process using one or more of the elements, functions described or depicted herein.

Features of the data are identified and extracted 346. In some embodiments, a feature of the data is internal to the prepared data from step 344. In other embodiments, a feature of the data requires a piece of prepared data from step 344 to be enriched by data from another data source to be used in developing an AI/ML model 332. In some embodiments, identifying features is a manual process or an automated process using one or more of the elements, functions described or depicted herein. Once the features have been identified, the values of the features are collected into a dataset that will be used to develop the AI/ML model 332.

The dataset output from feature extraction step 346 is split 348 into a training and validation data set. The training data set is used to train the AI/ML model 332, and the validation data set is used to evaluate the performance of the AI/ML model 332 on unseen data.

The AI/ML model 332 is trained and tuned 350 using the training data set from the data splitting step 348. In this step, the training data set is fed into an AI/ML algorithm with an initial set of algorithm parameters. The performance of the AI/ML model 332 is then tested within the AI/ML development system 340 utilizing the validation data set from step 348. These steps may be repeated with adjustments to one or more algorithm parameters until the model's performance is acceptable based on various goals and/or results.

The AI/ML model 332 is evaluated 352 in a staging environment (not shown) that resembles the ultimate AI/ML production system 330. This evaluation uses a validation dataset to ensure the performance in an AI/ML production system 330 matches or exceeds expectations. In some embodiments, the validation dataset from step 348 is used. In other embodiments, one or more unseen validation datasets are used. In some embodiments, the staging environment is part of the AI/ML development system 340. In other embodiments, the staging environment is managed separately from the AI/ML development system 340. Once the AI/ML model 332 has been validated, it is stored in an AI/ML model registry 360, which can be retrieved for deployment and future updates. As before, in some embodiments, the model evaluation step 352 is a manual process or an automated process using one or more of the elements, functions described or depicted herein.

Once an AI/ML model 332 has been validated and published to an AI/ML model registry 360, it may be deployed 354 to one or more AI/ML production systems 330. In some embodiments, the performance of deployed AI/ML models 332 is monitored 356 by the AI/ML development system 340. In some embodiments, AI/ML model 332 feedback data is provided by the AI/ML production system 330 to enable model performance monitoring 356. In some embodiments, the AI/ML development system 340 periodically requests feedback data for model performance monitoring 356. In some embodiments, model performance monitoring includes one or more triggers that result in the AI/ML model 332 being updated by repeating steps 342-354 with updated data from one or more data sources.

Figure 3C:
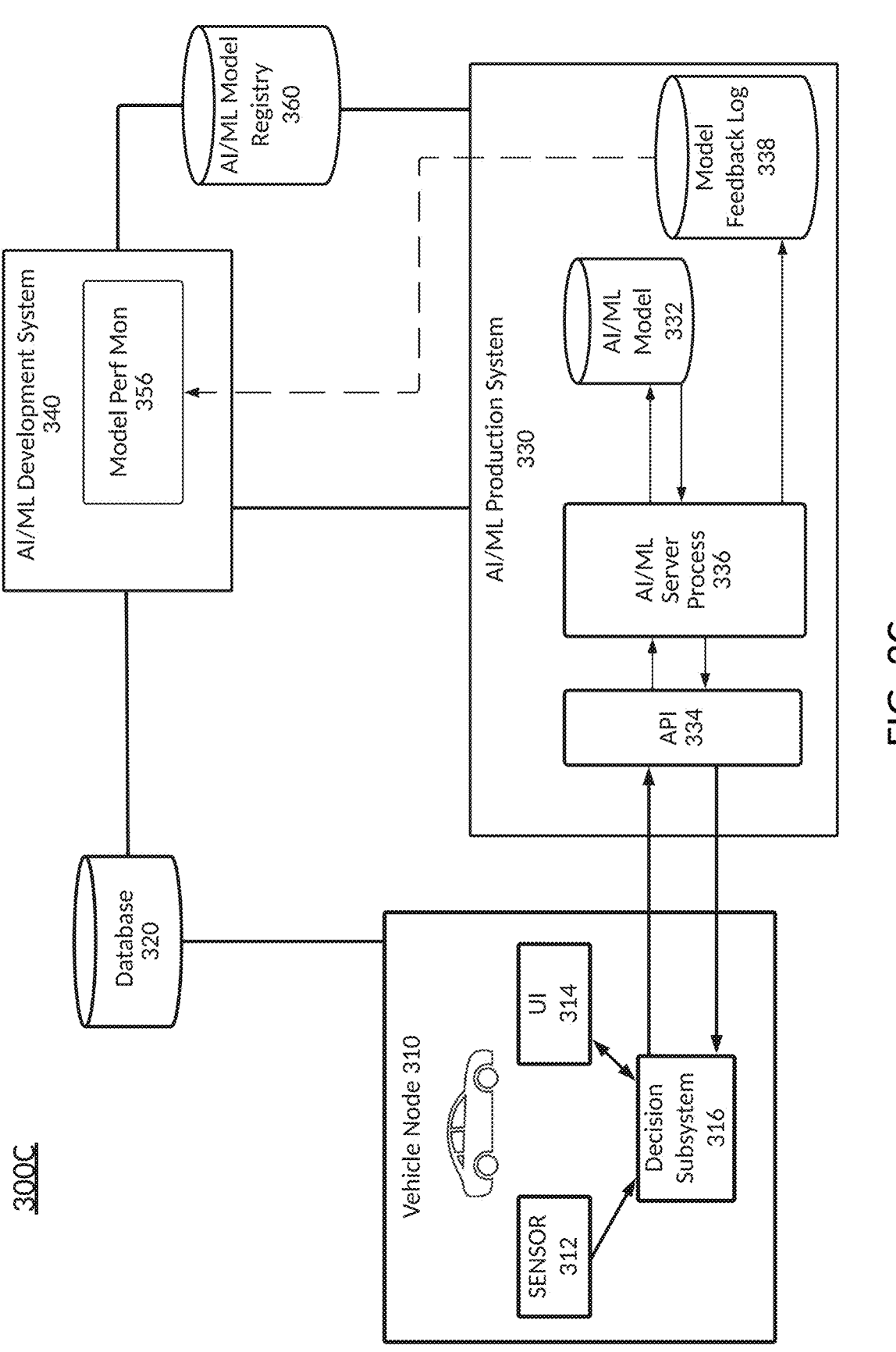
FIG. 3C illustrates a process for utilizing an Artificial Intelligence (AI)/Machine Learning (ML) model that supports AI-assisted vehicle or occupant decision points.

FIG. 3C illustrates a process 300C for utilizing an AI/ML model that supports AI-assisted vehicle or occupant decision points. As stated previously, the AI model utilization process depicted herein reflects ML, which is a particular branch of AI, but the instant solution is not limited to ML and is not limited to any AI algorithm or combination of algorithms.

Referring to FIG. 3C, an AI/ML production system 330 may be used by a decision subsystem 316 in vehicle node 310 to assist in its decision-making process. The AI/ML production system 330 provides an application programming interface (API) 334, executed by an AI/ML server process 336 through which requests can be made. In some embodiments, a request may include an AI/ML model 332 identifier to be executed. In some embodiments, the AI/ML model 332 to be executed is implicit based on the type of request. In some embodiments, a data payload (e.g., to be input to the model during execution) is included in the request. In some embodiments, the data payload includes sensor 312 data received from vehicle node 310. In some embodiments, the data payload includes UI 314 data from vehicle node 310. In some embodiments, the data payload includes data from other vehicle node 310 subsystems (not shown), including but not limited to, occupant data subsystems. In an embodiment, one or more elements or nodes 320, 330, 340, or 360 may be located in the vehicle 310.

Upon receiving the API 334 request, the AI/ML server process 336 may need to transform the data payload or portions of the data payload to be valid feature values into an AI/ML model 332. Data transformation may include but is not limited to combining data values, normalizing data values, and enriching the incoming data with data from other data sources. Once any required data transformation occurs, the AI/ML server process 336 executes the appropriate AI/ML model 332 using the transformed input data. Upon receiving the execution result, the AI/ML server process 336 responds to the API caller, which is a decision subsystem 316 of vehicle node 310. In some embodiments, the response may result in an update to a UI 314 in vehicle node 310. In some embodiments, the response includes a request identifier that can be used later by the decision subsystem 316 to provide feedback on the AI/ML model 332 performance. Further, in some embodiments, immediate performance feedback may be recorded into a model feedback log 338 by the AI/ML server process 336. In some embodiments, execution model failure is a reason for immediate feedback.

In some embodiments, the API 334 includes an interface to provide AI/ML model 332 feedback after an AI/ML model 332 execution response has been processed. This mechanism may be used to evaluate the performance of the AI/ML model 332 by enabling the API caller to provide feedback on the accuracy of the model results. For example, if the AI/ML model 332 provided an estimated time of arrival of 20 minutes, but the actual travel time was 24 minutes, that may be indicated. In some embodiments, the feedback interface includes the identifier of the initial request so that it can be used to associate the feedback with the request. Upon receiving a call into the feedback interface of API 334, the AI/ML server process 336 records the feedback in the model feedback log 338. In some embodiments, the data in this model feedback log 338 is provided to model performance monitoring 356 in the AI/ML development system 340. This log data is streamed to the AI/ML development system 340 in one embodiment. In some embodiments, the log data is provided upon request.

A number of the steps/features that may utilize the AI/ML process described herein include one or more of: identifying a state of an individual associated with a vehicle based on data of the individual stored in a profile, determining a current time of day from a system of the vehicle, determining a setting to change on one or more systems within the vehicle based on execution of an artificial intelligence (AI) model on the state of the individual and the current time of day, changing the setting on the one or more systems within the vehicle while the individual is within the vehicle, receiving sleep data of the individual from one or more sensors worn by the individual while the individual is outside of the vehicle, storing the sleep data in the profile, and identifying a circadian rhythm of the individual based on the sleep data, receiving input data from a mobile device of the individual which includes sleep preferences of the individual and storing the sleep preferences in the profile, and identifying a circadian rhythm of the individual based on the sleep preferences of the individual, determining the current time of day comprises determining the current time of day based on one or more of a system clock of the vehicle and an ambient light sensor of the vehicle, receiving a setting value for a system from among the one or more systems within the vehicle from the AI model via a software application installed within the vehicle, and issuing commands to the system within the vehicle to apply the setting value to the system, determining a setting value for a lighting system within an interior of the vehicle and audio content to be output by an infotainment system within the vehicle based on execution of the AI model on the state of the individual and the current time of day, and determining a position value for one or more of a steering wheel position, an arm rest position, mirror position, and sunshades, based on execution of the AI model the state of the individual and the current time of day.

Data associated with any of these steps/features, as well as any other features or functionality described or depicted herein, the AI/ML production system 330, as well as one or more of the other elements depicted in FIG. 3C may be used to process this data in a pre-transformation and/or post-transformation process. Data related to this process can be used by the vehicle node 310. In one embodiment, data related to this process may be used with a charging station/charging point, a server, a wireless device, and/or any of the processors described or depicted herein.

Figure 3D:
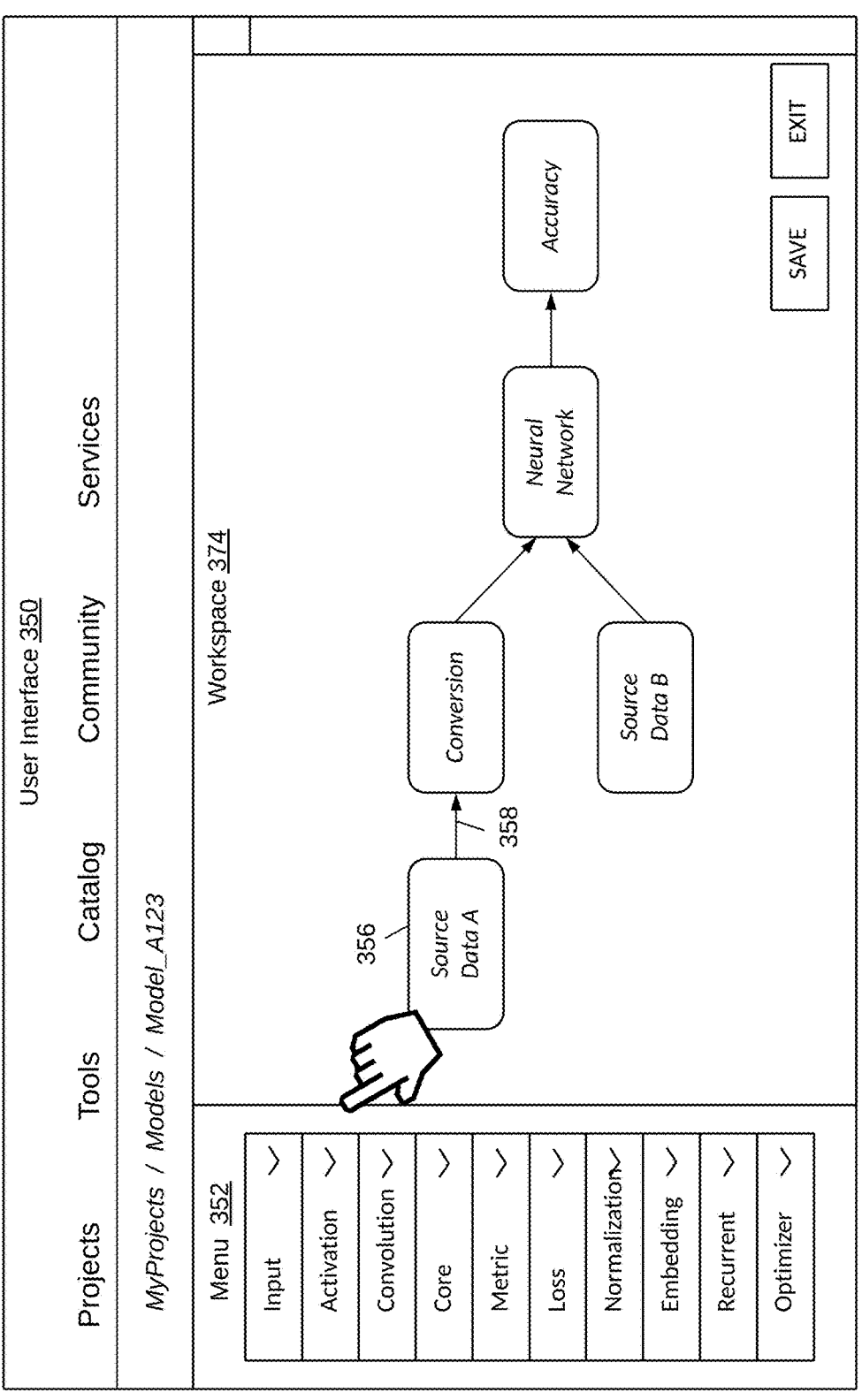
FIG. 3D illustrates a machine learning network diagram, according to example embodiments.

FIG. 3D illustrates a process 300D of designing a new machine learning model via a user interface 370 of the system according to example embodiments. As an example, a model may be output as part of the AI/ML development system 340. Referring to FIG. 3D, a user can use an input mechanism from a menu 372 of a user interface 370 to add pieces/components to a model being developed within a workspace 374 of the user interface 370.

The menu 372 includes a plurality of graphical user interface (GUI) menu options which can be selected to reveal additional components that can be added to the model design shown in the workspace 374. The GUI menu includes options for adding elements to the workspace, such as features which may include neural networks, machine learning models, AI models, data sources, conversion processes (e.g., vectorization, encoding, etc.), analytics, etc. The user can continue to add features to the model and connect them using edges or other means to create a flow within the workspace 374. For example, the user may add a node 376 to a flow of a new model within the workspace 374. For example, the user may connect the node 376 to another node in the diagram via an edge 378, creating a dependency within the diagram. When the user is done, the user can save the model for subsequent training/testing.

In another example, the name of the object can be identified from a web page or a user interface 370 where the object is visible within a browser or the workspace 374 on the user device. A pop-up within the browser or the workspace 374 can be overlayed where the object is visible. The pop-up includes an option to navigate to the identified web page corresponding to the alternative object via a rule set.

Figure 3E:
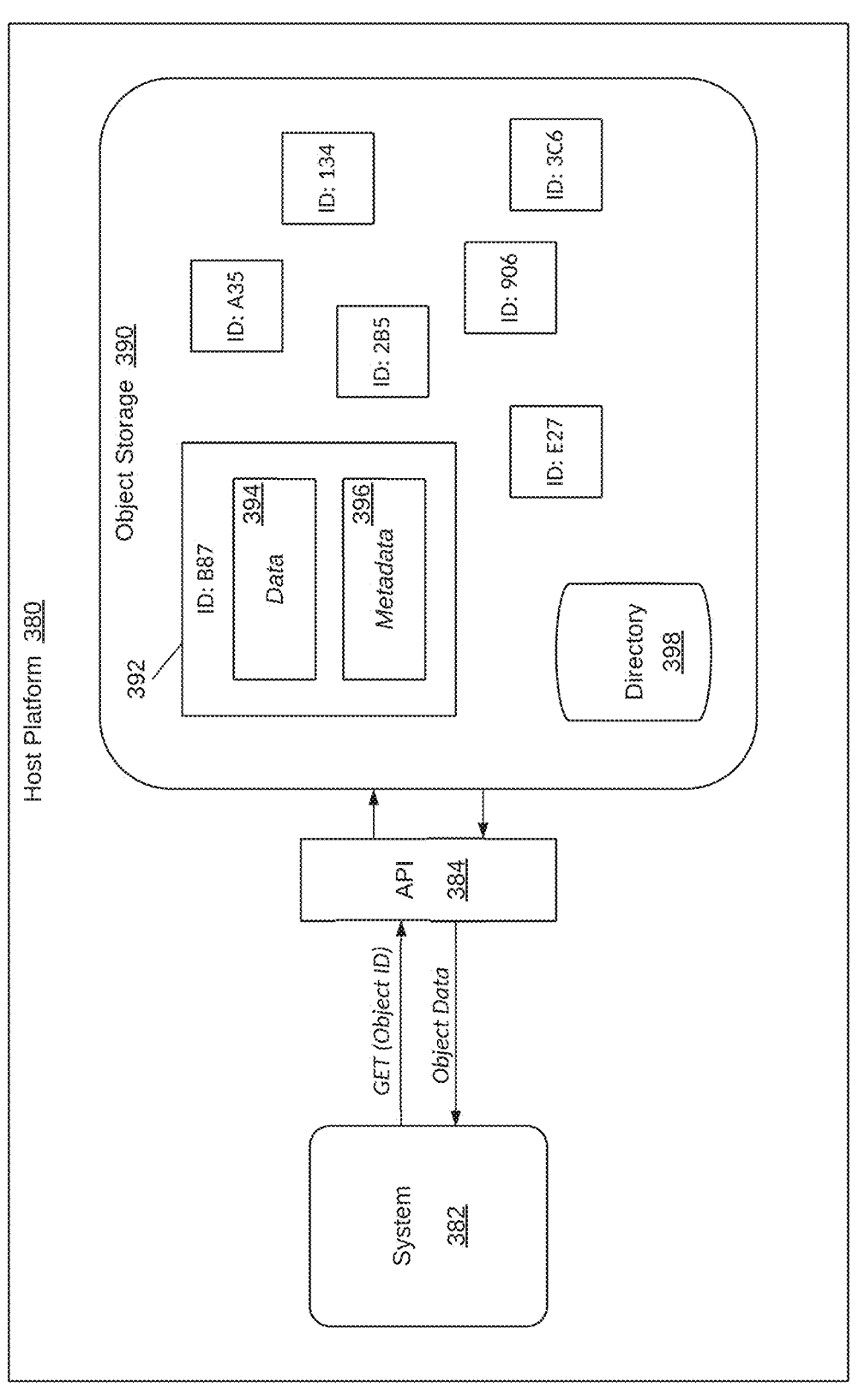
FIG. 3E illustrates a machine learning network diagram, according to example embodiments.

FIG. 3E illustrates a process 300E of accessing an object 392 from an object storage 390 of the host platform 380 according to example embodiments. For example, the object storage 390 may store data that is used by the AI models and machine learning (ML) models, including but not limited to, training data, expected outputs for testing, training results, and the like. The object storage 390 may also store any other kind of data. Each object may include a unique identifier, a data section 394, and a metadata section 396, which provide a descriptive context associated with the data, including data that can later be extracted for purposes of machine learning. The unique identifier may uniquely identify an object with respect to all other objects in the object storage 390. The data section 394 may include unstructured data such as web pages, digital content, images, audio, text, and the like.

Instead of breaking files into blocks stored on disks in a file system, the object storage 390 handles objects as discrete units of data stored in a structurally flat data environment. Here, the object storage may not use folders, directories, or complex hierarchies. Instead, each object may be a simple, self-contained repository that includes the data, the metadata, and the unique identifier that a client application can use to locate and access it. In this case, the metadata is more descriptive than a file-based approach. The metadata can be customized with additional context that can later be extracted and leveraged for other purposes, such as data analytics.

The objects that are stored in the object storage 390 may be accessed via an API 384. The API 384 may be a Hypertext Transfer Protocol (HTTP)-based RESTful API (also known as a RESTful Web service). The API 384 can be used by the client application to query an object's metadata to locate the desired object (data) via the Internet from anywhere on any device. The API 384 may use HTTP commands such as "PUT" or "POST" to upload an object, "GET" to retrieve an object, "DELETE" to remove an object, and the like.

The object storage 390 may provide a directory 398 that uses the metadata of the objects to locate appropriate data files. The directory 398 may contain descriptive information about each object stored in the object storage 390, such as a name, a unique identifier, a creation timestamp, a collection name, etc. To query the object within the object storage 390, the client application may submit a command, such as an HTTP command, with an identifier of the object 392, a payload, etc. The object storage 390 can store the actions and results described herein, including associating two or more lists of ranked assets with one another based on variables used by the two or more lists of ranked assets that have a correlation above a predetermined threshold.

Figure 4A:
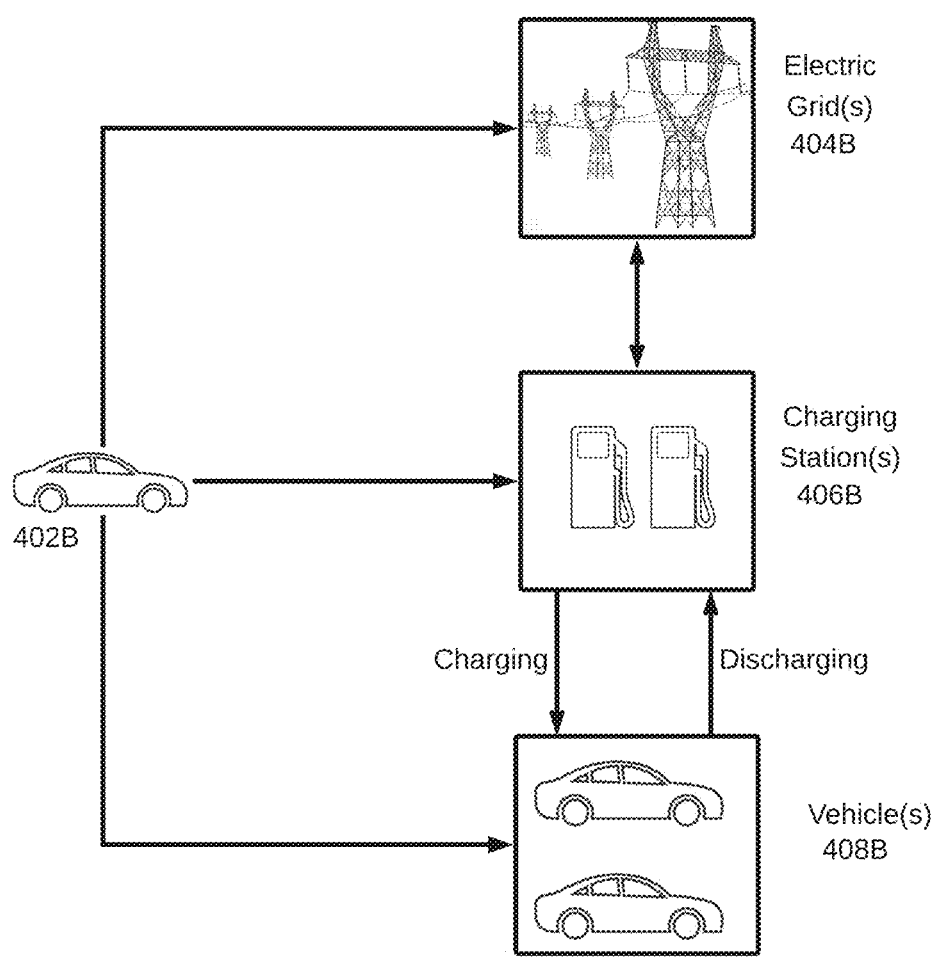
FIG. 4A illustrates a diagram depicting electrification of one or more elements, according to example embodiments.

FIG. 4A illustrates a diagram 400A depicting the electrification of one or more elements. In one example, a vehicle 402B may provide power stored in its batteries to one or more elements, including other vehicle(s) 408B, charging station(s) 406B, and electric grid(s) 404B. The electric grid(s) 404B is/are coupled to one or more of the charging station(s) 406B, which may be coupled to one or more of the vehicle(s) 408B. This configuration allows the distribution of electricity/power received from the vehicle 402B. The vehicle 402B may also interact with the other vehicle(s) 408B, such as via V2V technology, communication over cellular networks, Wi-Fi®, and the like. The vehicle 402B may also interact wirelessly and/or wired with other vehicles 408B, the charging station(s) 406B and/or with the electric grid(s) 404B. In one example, the vehicle 402B is routed (or routes itself) in a safe and efficient manner to the electric grid(s) 404B, the charging station(s) 406B, or the other vehicle(s) 408B. Using one or more embodiments of the instant solution, the vehicle 402B can provide energy to one or more of the elements depicted herein in various advantageous ways as described and/or depicted herein. Further, the safety and efficiency of the vehicle may be increased, and the environment may be positively affected as described and/or depicted herein.

The term 'energy', 'electricity', 'power', and the like may be used to denote any form of energy received, stored, used, shared, and/or lost by the vehicle(s). The energy may be referred to in conjunction with a voltage source and/or a current supply of charge provided from an entity to the vehicle(s) during a charge/use operation. Energy may also be in the form of fossil fuels (for example, for use with a hybrid vehicle) or via alternative power sources, including but not limited to lithium-based, nickel-based, hydrogen fuel cells, atomic/nuclear energy, fusion-based energy sources, and energy generated during an energy sharing and/or usage operation for increasing or decreasing one or more vehicles energy levels at a given time.

In one example, the charging station 406B manages the amount of energy transferred from the vehicle 402B such that there is sufficient charge remaining in the vehicle 402B to arrive at a destination. In one example, a wireless connection is used to wirelessly direct an amount of energy transfer between vehicles 408B, wherein the vehicles may both be in motion. In one embodiment, wireless charging may occur via a fixed charger and batteries of the vehicle in alignment with one another (such as a charging mat in a garage or parking space). In one example, an idle vehicle, such as a vehicle 402B (which may be autonomous) is directed to provide an amount of energy to a charging station 406B and return to the original location (for example, its original location or a different destination). In one example, a mobile energy storage unit (not shown) is used to collect surplus energy from at least one other vehicle 408B and transfer the stored surplus energy at a charging station 406B. In one example, factors determine an amount of energy to transfer to a charging station 406B, such as distance, time, traffic conditions, road conditions, environmental/weather conditions, the vehicle's condition (weight, etc.), an occupant(s) schedule while utilizing the vehicle, a prospective occupant(s) schedule waiting for the vehicle, etc. In one example, the vehicle(s) 408B, the charging station(s) 406B and/or the electric grid(s) 404B can provide energy to the vehicle 402B.

In one embodiment, a location such as a building, a residence, or the like (not depicted), is communicably coupled to one or more of the electric grid(s) 404B, the vehicle 402B, and/or the charging station(s) 406B. The rate of electric flow to one or more of the location, the vehicle 402B, the other vehicle(s) 408B is modified, depending on external conditions, such as weather. For example, when the external temperature is extremely hot or extremely cold, raising the chance for an outage of electricity, the flow of electricity to a connected vehicle 402B/408B is slowed to help minimize the chance of an outage.

In one embodiment, vehicles 402B and 408B may be utilized as bidirectional vehicles. Bidirectional vehicles are those that may serve as mobile microgrids that can assist in the supplying of electrical power to the grid 404B and/or reduce the power consumption when the grid is stressed. Bidirectional vehicles incorporate bidirectional charging, which in addition to receiving a charge to the vehicle, the vehicle can transfer energy from the vehicle to the grid 404B, otherwise referred to as "V2G". In bidirectional charging, the electricity flows both ways; to the vehicle and from the vehicle. When a vehicle is charged, alternating current (AC) electricity from the grid 404B is converted to direct current (DC). This may be performed by one or more of the vehicle's own converter(s) or a converter on the charging station 406B. The energy stored in the vehicle's batteries may be sent in an opposite direction back to the grid. The energy is converted from DC to AC through a converter usually located in the charging station 406B, otherwise referred to as a bidirectional charger. Further, the instant solution as described and depicted with respect to FIG. 4B can be utilized in this and other networks and/or systems.

Figure 4B:
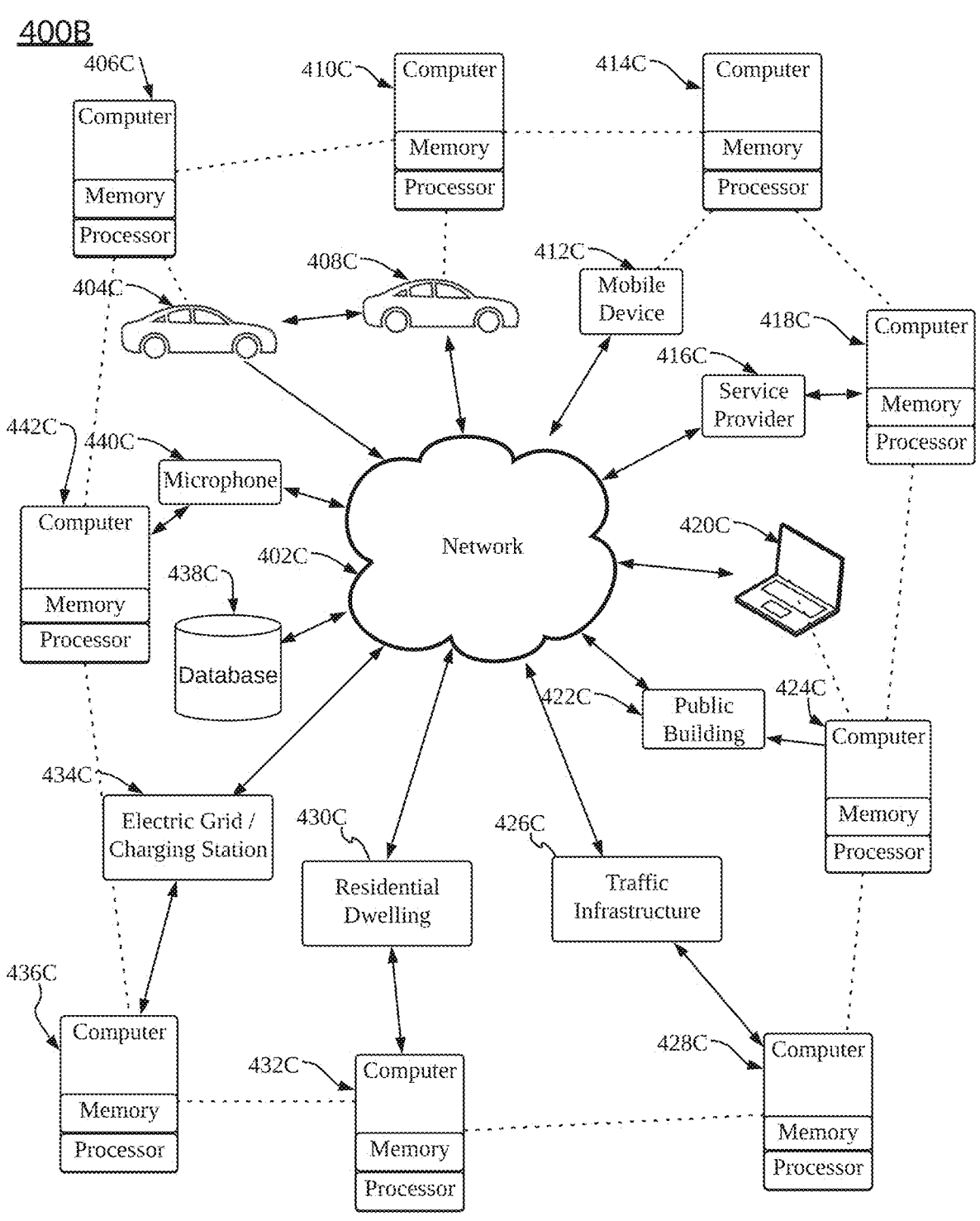
FIG. 4B illustrates a diagram depicting interconnections between different elements, according to example embodiments.

FIG. 4B is a diagram showing interconnections between different elements 400B. The instant solution may be stored and/or executed entirely or partially on and/or by one or more computing devices 414C, 418C, 424C, 428C, 432C, 436C, 406C, 442C and 410C associated with various entities, all communicably coupled and in communication with a network 402C. A database 438C is communicably coupled to the network and allows for the storage and retrieval of data. In one example, the database is an immutable ledger. One or more of the various entities may be a vehicle 404C, service provider 416C, public buildings 422C, traffic infrastructure 426C, residential dwellings 430C, an electric grid/charging station 434C, a microphone 440C, and/or another vehicle 408C. Other entities and/or devices, such as one or more private users using a smartphone 412C, a laptop 420C, an augmented reality (AR) device, a virtual reality (VR) device, and/or any wearable device may also interwork with the instant solution. The smartphone 412C, laptop 420C, the microphone 440C, and other devices may be connected to one or more of the connected computing devices 414C, 418C, 424C, 428C, 432C, 436C, 406C, 442C, and 410C. The one or more public buildings 422C may include various agencies. The one or more public buildings 422C may utilize a computing device 424C. The one or more service provider(s) 416C may include a dealership, a tow truck service, a collision center, or other repair shop. The one or more service provider(s) 416C may utilize a computing apparatus 418C. These various computer devices may be directly and/or communicably coupled to one another, such as via wired networks, wireless networks, blockchain networks, and the like. The microphone 440C may be utilized as a virtual assistant, in one example. In one example, the one or more traffic infrastructure 426C may include one or more traffic signals, one or more sensors including one or more cameras, vehicle speed sensors or traffic sensors, and/or other traffic infrastructure. The one or more traffic infrastructure 426C may utilize a computing device 428C.

In one embodiment, anytime an electrical charge is given or received to/from a charging station and/or an electrical grid, the entities that allow that to occur are one or more of a vehicle, a charging station, a server, and a network communicably coupled to the vehicle, the charging station, and the electrical grid.

In one example, a vehicle 408C/404C can transport a person, an object, a permanently or temporarily affixed apparatus, and the like. In one example, the vehicle 408C may communicate with vehicle 404C via V2V communication through the computers associated with each vehicle 406C and 410C and may be referred to as a car, vehicle, automobile, and the like. The vehicle 404C/408C may be a self-propelled wheeled conveyance, such as a car, a sports utility vehicle, a truck, a bus, a van, or other motor or battery-driven or fuel cell-driven vehicle. For example, vehicle 404C/408C may be an electric vehicle, a hybrid vehicle, a hydrogen fuel cell vehicle, a plug-in hybrid vehicle, or any other type of vehicle with a fuel cell stack, a motor, and/or a generator. Other examples of vehicles include bicycles, scooters, trains, planes, boats, and any other form of conveyance that is capable of transportation. The vehicle 404C/408C may be semi-autonomous or autonomous. For example, vehicle 404C/408C may be self-maneuvering and navigate without human input. An autonomous vehicle may have and use one or more sensors and/or a navigation unit to drive autonomously. All of the data described or depicted herein can be stored, analyzed, processed and/or forwarded by one or more of the elements in FIG. 4B.

Figure 4C:
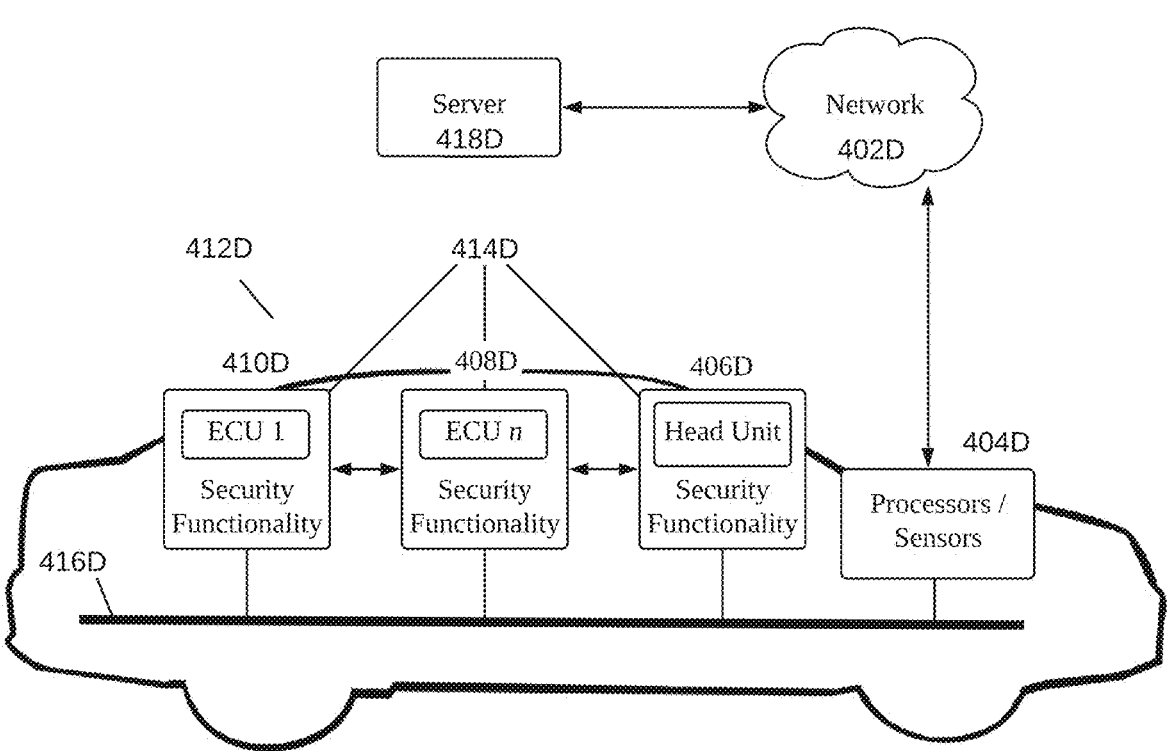
FIG. 4C illustrates a further diagram depicting interconnections between different elements, according to example embodiments.

FIG. 4C is another block diagram showing interconnections between different elements in one example 400C. A vehicle 412D is presented and includes ECUs 410D, 408D, and a head unit (otherwise known as an infotainment system) 406D. An ECU is an embedded system in automotive electronics controlling one or more of the electrical systems or subsystems in a vehicle. ECUs may include but are not limited to the management of a vehicle's engine, brake system, gearbox system, door locks, dashboard, airbag system, infotainment system, electronic differential, and active suspension. ECUs are connected to the vehicle's Controller Area Network (CAN) bus 416D. The ECUs may also communicate with a vehicle computer 404D via the CAN bus 416D. The vehicle's processors/sensors (such as the vehicle computer) 404D can communicate with external elements, such as a server 418D via a network 402D (such as the Internet). Each ECU 410D, 408D, and head unit 406D may contain its own security policy. The security policy defines permissible processes that can be executed in the proper context. In one example, the security policy may be partially or entirely provided in the vehicle computer 404D.

ECUs 410D, 408D, and head unit 406D may each include a custom security functionality element 414D defining authorized processes and contexts within which those processes are permitted to run. Context-based authorization to determine validity if a process can be executed allows ECUs to maintain secure operation and prevent unauthorized access from elements such as the vehicle's CAN Bus. When an ECU encounters a process that is unauthorized, that ECU can block the process from operating. Automotive ECUs can use different contexts to determine whether a process is operating within its permitted bounds, such as proximity contexts, nearby objects, distance to approaching objects, speed, and trajectory relative to other moving objects, and operational contexts such as an indication of whether the vehicle is moving or parked, the vehicle's current speed, the transmission state, user-related contexts such as devices connected to the transport via wireless protocols, use of the infotainment, cruise control, parking assist, driving assist, location-based contexts, and/or other contexts.

Figure 4D:
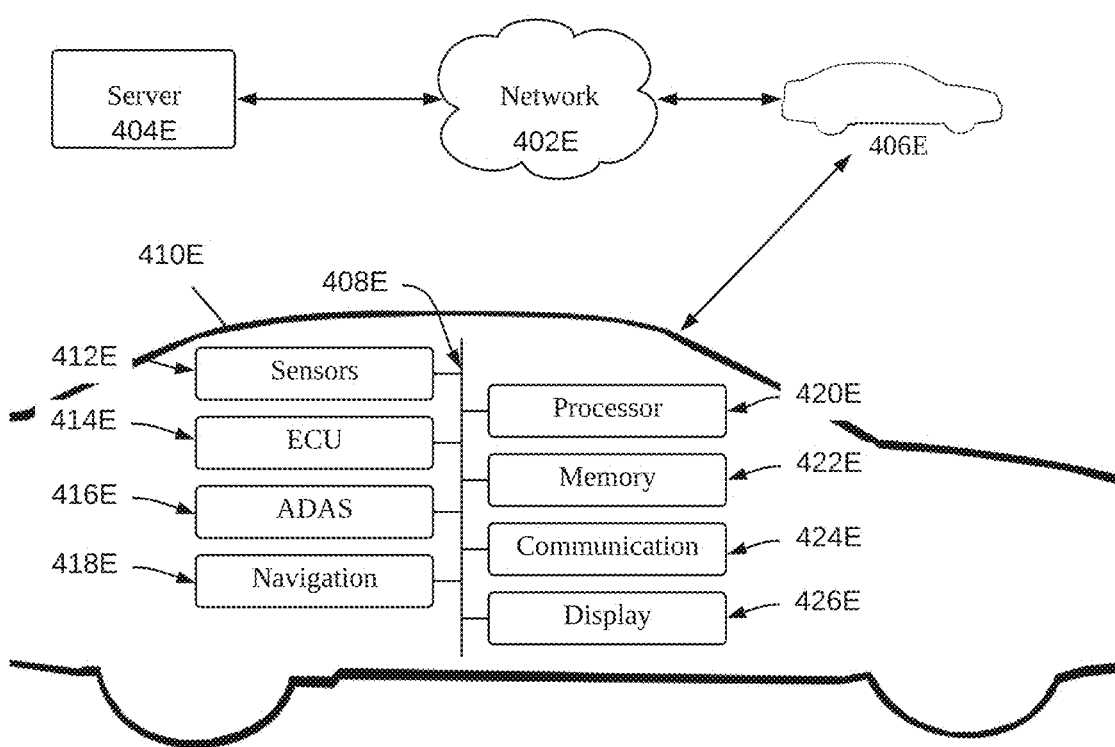
FIG. 4D illustrates yet a further diagram depicting interconnections between elements, according to example embodiments.

Referring to FIG. 4D, an operating environment 400D for a connected vehicle, is illustrated according to some embodiments. As depicted, the vehicle 410E includes a CAN bus 408E connecting elements 412E-426E of the vehicle. Other elements may be connected to the CAN bus and are not depicted herein. The depicted elements connected to the CAN bus include a sensor set 412E, Electronic Control Units 414E, autonomous features or Advanced Driver Assistance Systems (ADAS) 416E, and the navigation system 418E. In some embodiments, the vehicle 410E includes a processor 420E, a memory 422E, a communication unit 424E, and an electronic display 426E.

The processor 420E includes an arithmetic logic unit, a microprocessor, a general-purpose controller, and/or a similar processor array to perform computations and provide electronic display signals to a display unit 426E. The processor 420E processes data signals and may include various computing architectures, including a complex instruction set computer (CISC) architecture, a reduced instruction set computer (RISC) architecture, or an architecture implementing a combination of instruction sets. The vehicle 410E may include one or more processors 420E. Other processors, operating systems, sensors, displays, and physical configurations that are communicably coupled to one another (not depicted) may be used with the instant solution.

Memory 422E is a non-transitory memory storing instructions or data that may be accessed and executed by the processor 420E. The instructions and/or data may include code to perform the techniques described herein. The memory 422E may be a dynamic random-access memory (DRAM) device, a static random-access memory (SRAM) device, flash memory, or another memory device. In some embodiments, the memory 422E also may include non-volatile memory or a similar permanent storage device and media, which may include a hard disk drive, a floppy disk drive, a compact disc read only memory (CD-ROM) device, a digital versatile disk read only memory (DVD-ROM) device, a digital versatile disk random access memory (DVD-RAM) device, a digital versatile disk rewritable (DVD-RW) device, a flash memory device, or some other mass storage device for storing information on a permanent basis. A portion of the memory 422E may be reserved for use as a buffer or virtual random-access memory (virtual RAM). The vehicle 410E may include one or more memories 422E without deviating from the current solution.

The memory 422E of the vehicle 410E may store one or more of the following types of data: navigation route data 418E, and autonomous features data 416E. In some embodiments, the memory 422E stores data that may be necessary for the navigation application 418E to provide the functions.

The navigation system 418E may describe at least one navigation route including a start point and an endpoint. In some embodiments, the navigation system 418E of the vehicle 410E receives a request from a user for navigation routes wherein the request includes a starting point and an ending point. The navigation system 418E may query a real-time data server 404E (via a network 402E), such as a server that provides driving directions, for navigation route data corresponding to navigation routes, including the start point and the endpoint. The real-time data server 404E transmits the navigation route data to the vehicle 410E via a wireless network 402E, and the communication system 424E stores the navigation data 418E in the memory 422E of the vehicle 410E.

The ECU 414E controls the operation of many of the systems of the vehicle 410E, including the ADAS systems 416E. The ECU 414E may, responsive to instructions received from the navigation system 418E, deactivate any unsafe and/or unselected autonomous features for the duration of a journey controlled by the ADAS systems 416E. In this way, the navigation system 418E may control whether ADAS systems 416E are activated or enabled so that they may be activated for a given navigation route.

The sensor set 412E may include any sensors in the vehicle 410E generating sensor data. For example, the sensor set 412E may include short-range sensors and long-range sensors. In some embodiments, the sensor set 412E of the vehicle 410E may include one or more of the following vehicle sensors: a camera, a Light Detection and Ranging (Lidar) sensor, an ultrasonic sensor, an automobile engine sensor, a radar sensor, a laser altimeter, a manifold absolute pressure sensor, an infrared detector, a motion detector, a thermostat, a sound detector, a carbon monoxide sensor, a carbon dioxide sensor, an oxygen sensor, a mass airflow sensor, an engine coolant temperature sensor, a throttle position sensor, a crankshaft position sensor, a valve timer, an air-fuel ratio meter, a blind spot meter, a curb feeler, a defect detector, a Hall effect sensor, a parking sensor, a radar gun, a speedometer, a speed sensor, a tire-pressure monitoring sensor, a torque sensor, a transmission fluid temperature sensor, a turbine speed sensor (TSS), a variable reluctance sensor, a vehicle speed sensor (VSS), a water sensor, a wheel speed sensor, a global positioning system (GPS) sensor, a mapping functionality, and any other type of automotive sensor. The navigation system 418E may store the sensor data in the memory 422E.

The communication unit 424E transmits and receives data to and from the network 402E or to another communication channel. In some embodiments, the communication unit 424E may include a dedicated short-range communication (DSRC) transceiver, a DSRC receiver, and other hardware or software necessary to make the vehicle 410E a DSRC-equipped device.

The vehicle 410E may interact with other vehicles 406E via V2V technology. V2V communication includes sensing radar information corresponding to relative distances to external objects, receiving GPS information of the vehicles, setting areas where the other vehicles 406E are located based on the sensed radar information, calculating probabilities that the GPS information of the object vehicles will be located at the set areas, and identifying vehicles and/or objects corresponding to the radar information and the GPS information of the object vehicles based on the calculated probabilities, in one example.

For a vehicle to be adequately secured, the vehicle must be protected from unauthorized physical access as well as unauthorized remote access (e.g., cyber-threats). To prevent unauthorized physical access, a vehicle is equipped with a secure access system such as a keyless entry in one example. Meanwhile, security protocols are added to a vehicle's computers and computer networks to facilitate secure remote communications to and from the vehicle in one example.

ECUs are nodes within a vehicle that control tasks such as activating the windshield wipers to tasks such as an anti-lock brake system. ECUs are often connected to one another through the vehicle's central network, which may be referred to as a controller area network (CAN). State-of-the-art features such as autonomous driving are strongly reliant on implementing new, complex ECUs such as ADAS, sensors, and the like. While these new technologies have helped improve the safety and driving experience of a vehicle, they have also increased the number of externally-communicating units inside of the vehicle, making them more vulnerable to attack. Below are some examples of protecting the vehicle from physical intrusion and remote intrusion.

In one embodiment, a CAN includes a CAN bus with a high and low terminal and a plurality of ECUs, which are connected to the CAN bus via wired connections. The CAN bus is designed to allow microcontrollers and devices to communicate with each other in an application without a host computer. The CAN bus implements a message-based protocol (i.e., ISO 11898 standards) that allows ECUs to send commands to one another at a root level. Meanwhile, the ECUs represent controllers for controlling electrical systems or subsystems within the vehicle. Examples of the electrical systems include power steering, anti-lock brakes, air-conditioning, tire pressure monitoring, cruise control, and many other features.

In this example, the ECU includes a transceiver and a microcontroller. The transceiver may be used to transmit and receive messages to and from the CAN bus. For example, the transceiver may convert the data from the microcontroller into a format of the CAN bus and also convert data from the CAN bus into a format for the microcontroller. Meanwhile, the microcontroller interprets the messages and also decides what messages to send using ECU software installed therein in one example.

To protect the CAN from cyber threats, various security protocols may be implemented. For example, sub-networks (e.g., sub-networks A and B, etc.) may be used to divide the CAN into smaller sub-CANs and limit an attacker's capabilities to access the vehicle remotely. In one embodiment, a firewall (or gateway, etc.) may be added to block messages from crossing the CAN bus across sub-networks. If an attacker gains access to one sub-network, the attacker will not have access to the entire network. To make sub-networks even more secure, the most critical ECUs are not placed on the same sub-network, in one example.

In addition to protecting a vehicle's internal network, vehicles may also be protected when communicating with external networks such as the Internet. One of the benefits of having a vehicle connection to a data source such as the Internet is that information from the vehicle can be sent through a network to remote locations for analysis. Examples of vehicle information include GPS, onboard diagnostics, tire pressure, and the like. These communication systems are often referred to as telematics because they involve the combination of telecommunications and informatics. Further, the instant solution as described and depicted can be utilized in this and other networks and/or systems, including those that are described and depicted herein.

Figure 4E:
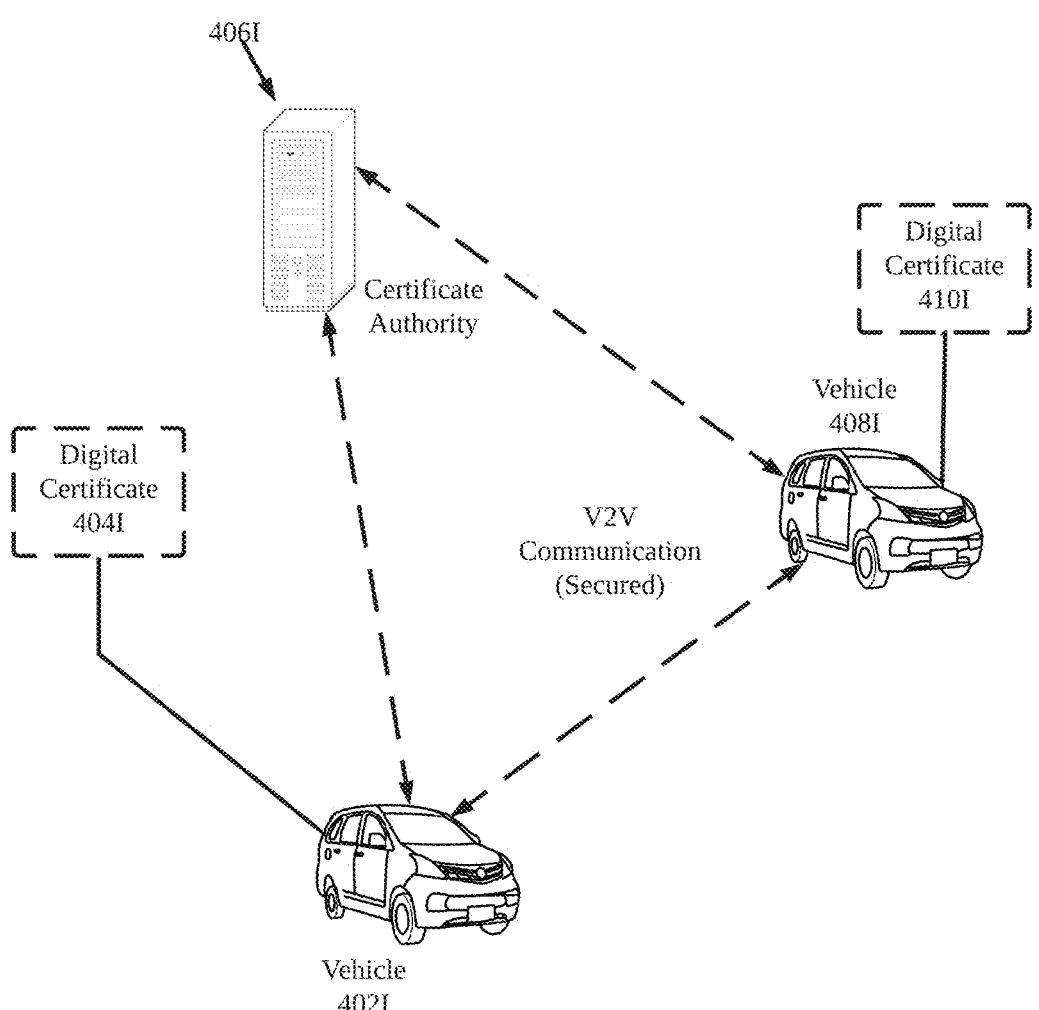
FIG. 4E illustrates yet a further diagram depicting an example of vehicles performing secured Vehicle-to-Vehicle (V2V) communications using security certificates, according to example embodiments.

FIG. 4E illustrates an example 400E of vehicles 402I and 408I performing secured V2V communications using security certificates, according to example embodiments. Referring to FIG. 4E, the vehicles 402I and 408I may communicate via V2V communications over a short-range network, a cellular network, or the like. Before sending messages, the vehicles 402I and 408I may sign the messages using a respective public key certificate. For example, the vehicle 402I may sign a V2V message using a public key certificate 404I. Likewise, the vehicle 408I may sign a V2V message using a public key certificate 410I. The public key certificates 404I and 410I are associated with the vehicles 402I and 408I, respectively, in one example.

Upon receiving the communications from each other, the vehicles may verify the signatures with a certificate authority 406I or the like. For example, the vehicle 408I may verify with the certificate authority 406I that the public key certificate 404I used by vehicle 402I to sign a V2V communication is authentic. If the vehicle 408I successfully verifies the public key certificate 404I, the vehicle knows that the data is from a legitimate source. Likewise, the vehicle 402I may verify with the certificate authority 406I that the public key certificate 410I used by the vehicle 408I to sign a V2V communication is authentic. Further, the instant solution as described and depicted with respect to FIG. 4E can be utilized in this and other networks and/or systems including those that are described and depicted herein.

In some embodiments, a computer may include a security processor. In particular, the security processor may perform authorization, authentication, cryptography (e.g., encryption), and the like, for data transmissions that are sent between ECUs and other devices on a CAN bus of a vehicle, and also data messages that are transmitted between different vehicles. The security processor may include an authorization module, an authentication module, and a cryptography module. The security processor may be implemented within the vehicle's computer and may communicate with other vehicle elements, for example, the ECUs/CAN network, wired and wireless devices such as wireless network interfaces, input ports, and the like. The security processor may ensure that data frames (e.g., CAN frames, etc.) that are transmitted internally within a vehicle (e.g., via the ECUs/CAN network) are secure. Likewise, the security processor can ensure that messages transmitted between different vehicles and devices attached or connected via a wire to the vehicle's computer are also secured.

For example, the authorization module may store passwords, usernames, PIN codes, biometric scans, and the like for different vehicle users. The authorization module may determine whether a user (or technician) has permission to access certain settings such as a vehicle's computer. In some embodiments, the authorization module may communicate with a network interface to download any necessary authorization information from an external server. When a user desires to make changes to the vehicle settings or modify technical details of the vehicle via a console or GUI within the vehicle or via an attached/connected device, the authorization module may require the user to verify themselves in some way before such settings are changed. For example, the authorization module may require a username, a password, a PIN code, a biometric scan, a predefined line drawing or gesture, and the like. In response, the authorization module may determine whether the user has the necessary permissions (access, etc.) being requested.

The authentication module may be used to authenticate internal communications between ECUs on the CAN network of the vehicle. As an example, the authentication module may provide information for authenticating communications between the ECUs. As an example, the authentication module may transmit a bit signature algorithm to the ECUs of the CAN network. The ECUs may use the bit signature algorithm to insert authentication bits into the CAN fields of the CAN frame. All ECUs on the CAN network typically receive each CAN frame. The bit signature algorithm may dynamically change the position, amount, etc., of authentication bits each time a new CAN frame is generated by one of the ECUs. The authentication module may also provide a list of ECUs that are exempt (safe list) and that do not need to use the authentication bits. The authentication module may communicate with a remote server to retrieve updates to the bit signature algorithm and the like.

The encryption module may store asymmetric key pairs to be used by the vehicle to communicate with other external user devices and vehicles. For example, the encryption module may provide a private key to be used by the vehicle to encrypt/decrypt communications, while the corresponding public key may be provided to other user devices and vehicles to enable the other devices to decrypt/encrypt the communications. The encryption module may communicate with a remote server to receive new keys, updates to keys, keys of new vehicles, users, etc., and the like. The encryption module may also transmit any updates to a local private/public key pair to the remote server.

Figure 5A:
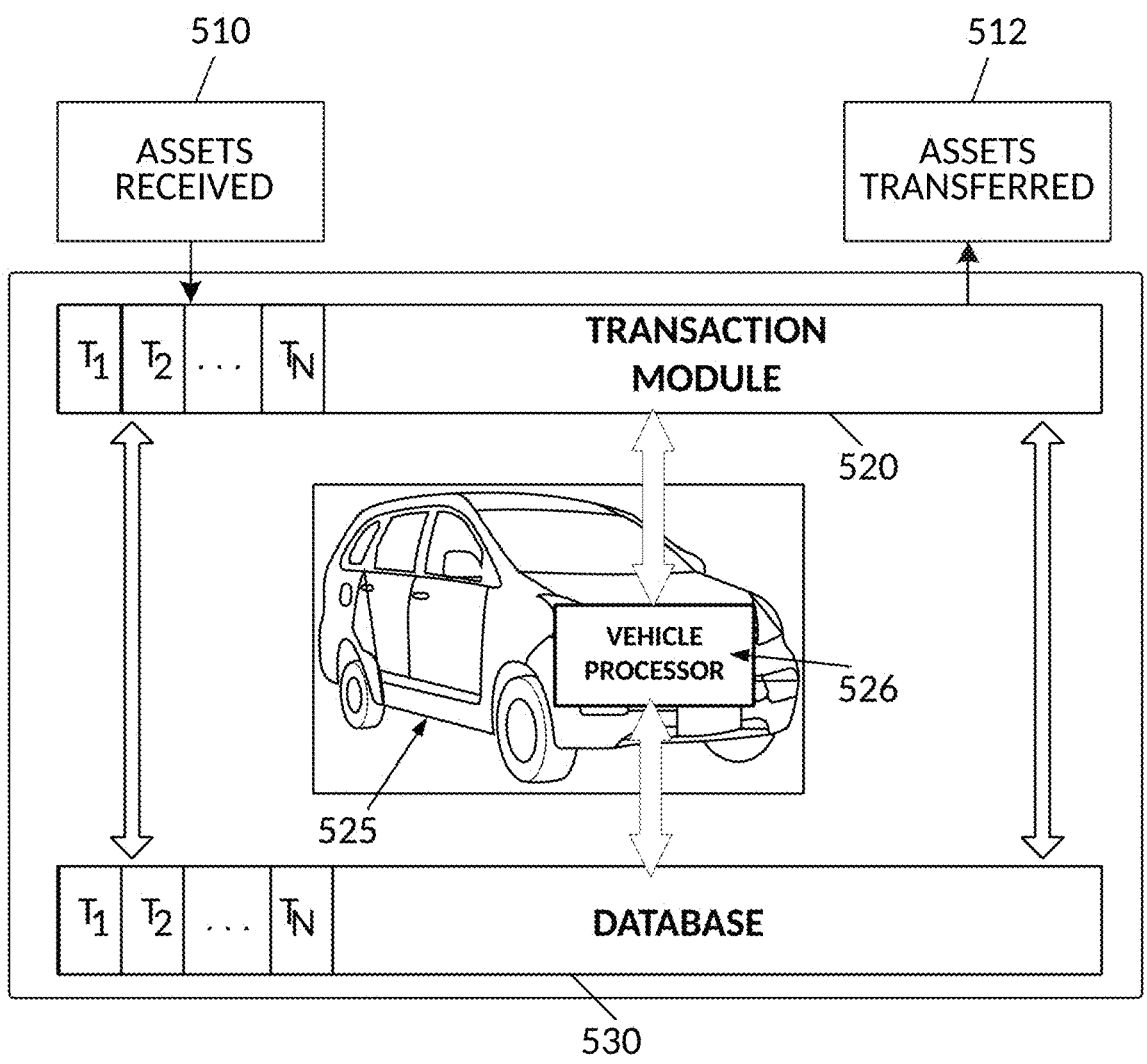
FIG. 5A illustrates an example vehicle configuration for managing database transactions associated with a vehicle, according to example embodiments.

FIG. 5A illustrates an example vehicle configuration 500A for managing database transactions associated with a vehicle, according to example embodiments. Referring to FIG. 5A, as a particular vehicle 525 is engaged in transactions (e.g., vehicle service, dealer transactions, delivery/pickup, transportation services, etc.), the vehicle may receive assets 510 and/or expel/transfer assets 512 according to a transaction(s). A vehicle processor 526 resides in the vehicle 525 and communication exists between the vehicle processor 526, a database 530, and the transaction module 520. The transaction module 520 may record information, such as assets, parties, credits, service descriptions, date, time, location, results, notifications, unexpected events, etc. Those transactions in the transaction module 520 may be replicated into a database 530. The database 530 can be one of a SQL database, a relational database management system (RDBMS), a relational database, a non-relational database, a blockchain, a distributed ledger, and may be on board the vehicle, may be off-board the vehicle, may be accessed directly and/or through a network, or be accessible to the vehicle.

In one embodiment, a vehicle may engage with another vehicle to perform various actions such as to share, transfer, acquire service calls, etc. when the vehicle has reached a status where the services need to be shared with another vehicle. For example, the vehicle may be due for a battery charge and/or may have an issue with a tire and may be en route to pick up a package for delivery. A vehicle processor resides in the vehicle and communication exists between the vehicle processor, a first database, and a transaction module. The vehicle may notify another vehicle, which is in its network and which operates on its blockchain member service. A vehicle processor resides in another vehicle and communication exists between the vehicle processor, a second database, the vehicle processor, and a transaction module. The another vehicle may then receive the information via a wireless communication request to perform the package pickup from the vehicle and/or from a server (not shown). The transactions are logged in the transaction modules and of both vehicles. The credits are transferred from the vehicle to the other vehicle and the record of the transferred service is logged in the first database, assuming that the blockchains are different from one another, or are logged in the same blockchain used by all members. The first database can be one of a SQL database, an RDBMS, a relational database, a non-relational database, a blockchain, a distributed ledger, and may be on board the vehicle, may be off-board the vehicle, may be accessible directly and/or through a network.

Figure 5B:
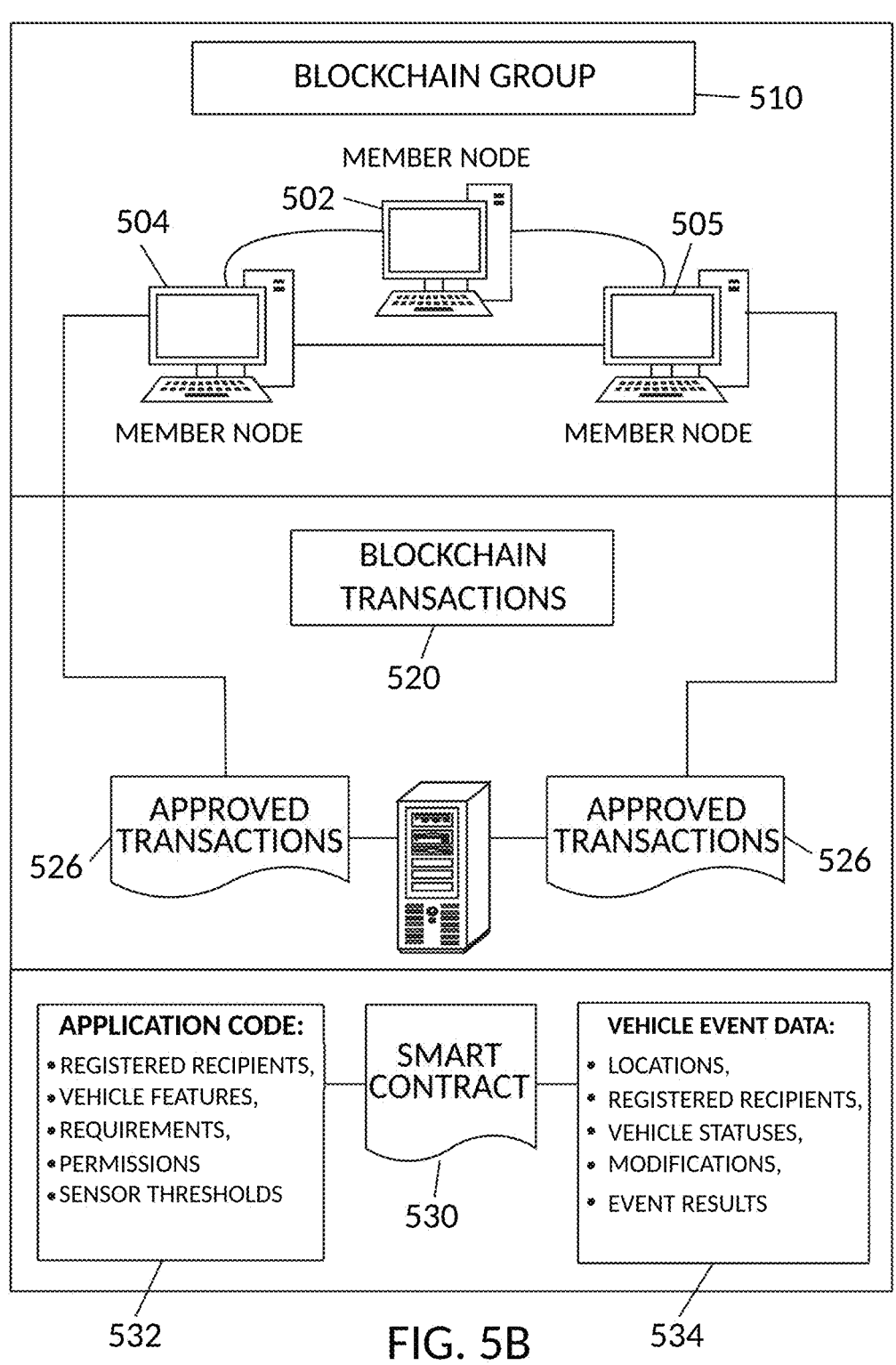
FIG. 5B illustrates an example blockchain group, according to example embodiments.

FIG. 5B illustrates a blockchain architecture configuration 500B, according to example embodiments. Referring to FIG. 5B, the blockchain architecture 500B may include certain blockchain elements, for example, a group of blockchain member nodes 502-505 as part of a blockchain group 510. In one example embodiment, a permissioned blockchain is not accessible to all parties but only to those members with permissioned access to the blockchain data. The blockchain nodes participate in a number of activities, such as blockchain entry addition and validation process (consensus). One or more of the blockchain nodes may endorse entries based on an endorsement policy and may provide an ordering service for all blockchain nodes. A blockchain node may initiate a blockchain action (such as an authentication) and seek to write to a blockchain immutable ledger stored in the blockchain, a copy of which may also be stored on the underpinning physical infrastructure.

The blockchain transactions 520 are stored in memory of computers as the transactions are received and approved by the consensus model dictated by the members' nodes. Approved transactions 526 are stored in current blocks of the blockchain and committed to the blockchain via a committal procedure, which includes performing a hash of the data contents of the transactions in a current block and referencing a previous hash of a previous block. Within the blockchain, one or more smart contracts 530 may exist that define the terms of transaction agreements and actions included in smart contract executable application code 532, such as registered recipients, vehicle features, requirements, permissions, sensor thresholds, etc. The code may be configured to identify whether requesting entities are registered to receive vehicle services, what service features they are entitled/required to receive given their profile statuses and whether to monitor their actions in subsequent events. For example, when a service event occurs and a user is riding in the vehicle, the sensor data monitoring may be triggered, and a certain parameter, such as a vehicle charge level, may be identified as being above/below a particular threshold for a particular period of time, then the result may be a change to a current status, which requires an alert to be sent to the managing party (i.e., vehicle owner, vehicle operator, server, etc.) so the service can be identified and stored for reference. The vehicle sensor data collected may be based on types of sensor data used to collect information about vehicle's status. The sensor data may also be the basis for the vehicle event data 534, such as a location(s) to be traveled, an average speed, a top speed, acceleration rates, whether there were any collisions, was the expected route taken, what is the next destination, whether safety measures are in place, whether the vehicle has enough charge/fuel, etc. All such information may be the basis of smart contract terms 530, which are then stored in a blockchain. For example, sensor thresholds stored in the smart contract can be used as the basis for whether a detected service is necessary and when and where the service should be performed.

In one embodiment, a blockchain logic example includes a blockchain application interface as an API or plug-in application that links to the computing device and execution platform for a particular transaction. The blockchain configuration may include one or more applications, which are linked to application programming interfaces (APIs) to access and execute stored program/application code (e.g., smart contract executable code, smart contracts, etc.), which can be created according to a customized configuration sought by participants and can maintain their own state, control their own assets, and receive external information. This can be deployed as an entry and installed, via appending to the distributed ledger, on all blockchain nodes.

The smart contract application code provides a basis for the blockchain transactions by establishing application code, which when executed causes the transaction terms and conditions to become active. The smart contract, when executed, causes certain approved transactions to be generated, which are then forwarded to the blockchain platform. The platform includes a security/authorization, computing devices, which execute the transaction management and a storage portion as a memory that stores transactions and smart contracts in the blockchain.

The blockchain platform may include various layers of blockchain data, services (e.g., cryptographic trust services, virtual execution environment, etc.), and underpinning physical computer infrastructure that may be used to receive and store new entries and provide access to auditors, which are seeking to access data entries. The blockchain may expose an interface that provides access to the virtual execution environment necessary to process the program code and engage the physical infrastructure. Cryptographic trust services may be used to verify entries such as asset exchange entries and keep information private.

The blockchain architecture configuration of FIGS. 5A and 5B may process and execute program/application code via one or more interfaces exposed, and services provided, by the blockchain platform. As a non-limiting example, smart contracts may be created to execute reminders, updates, and/or other notifications subject to the changes, updates, etc. The smart contracts can themselves be used to identify rules associated with authorization and access requirements and usage of the ledger. For example, the information may include a new entry, which may be processed by one or more processing entities (e.g., processors, virtual machines, etc.) included in the blockchain layer. The result may include a decision to reject or approve the new entry based on the criteria defined in the smart contract and/or a consensus of the peers. The physical infrastructure may be utilized to retrieve any of the data or information described herein.

Within smart contract executable code, a smart contract may be created via a high-level application and programming language, and then written to a block in the blockchain. The smart contract may include executable code that is registered, stored, and/or replicated with a blockchain (e.g., distributed network of blockchain peers). An entry is an execution of the smart contract code, which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A smart contract executable code may include the code interpretation of a smart contract, with additional features. As described herein, the smart contract executable code may be program code deployed on a computing network, where it is executed and validated by chain validators together during a consensus process. The smart contract executable code receives a hash and retrieves from the blockchain a hash associated with the data template created by use of a previously stored feature extractor. If the hashes of the hash identifier and the hash created from the stored identifier template data match, then the smart contract executable code sends an authorization key to the requested service. The smart contract executable code may write to the blockchain data associated with the cryptographic details.

Figure 5C:
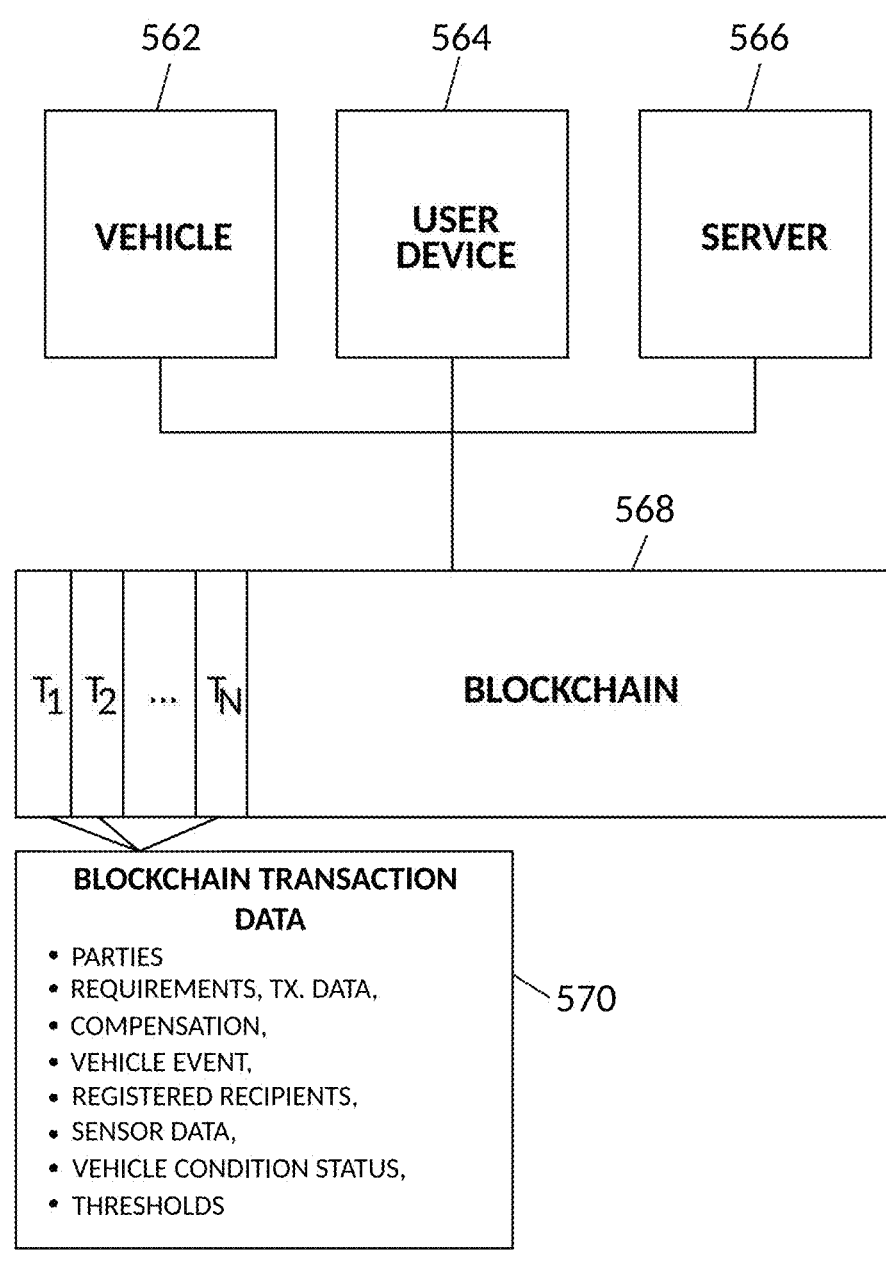
FIG. 5C illustrates an example interaction between elements and a blockchain, according to example embodiments.

FIG. 5C illustrates a blockchain configuration for storing blockchain transaction data, according to example embodiments. Referring to FIG. 5C, the example configuration 500C provides for the vehicle 562, the user device 564 and a server 566 sharing information with a distributed ledger (i.e., blockchain) 568. The server may represent a service provider entity inquiring with a vehicle service provider to share user profile rating information in the event that a known and established user profile is attempting to rent a vehicle with an established rated profile. The server 566 may be receiving and processing data related to a vehicle's service requirements. As the service events occur, such as the vehicle sensor data indicates a need for fuel/charge, a maintenance service, etc., a smart contract may be used to invoke rules, thresholds, sensor information gathering, etc., which may be used to invoke the vehicle service event. The blockchain transaction data 570 is saved for each transaction, such as the access event, the subsequent updates to a vehicle's service status, event updates, etc. The transactions may include the parties, the requirements (e.g., 18 years of age, service eligible candidate, valid driver's license, etc.), compensation levels, the distance traveled during the event, the registered recipients permitted to access the event and host a vehicle service, rights/permissions, sensor data retrieved during the vehicle event operation to log details of the next service event and identify a vehicle's condition status, and thresholds used to make determinations about whether the service event was completed and whether the vehicle's condition status has changed.

Figure 5D:
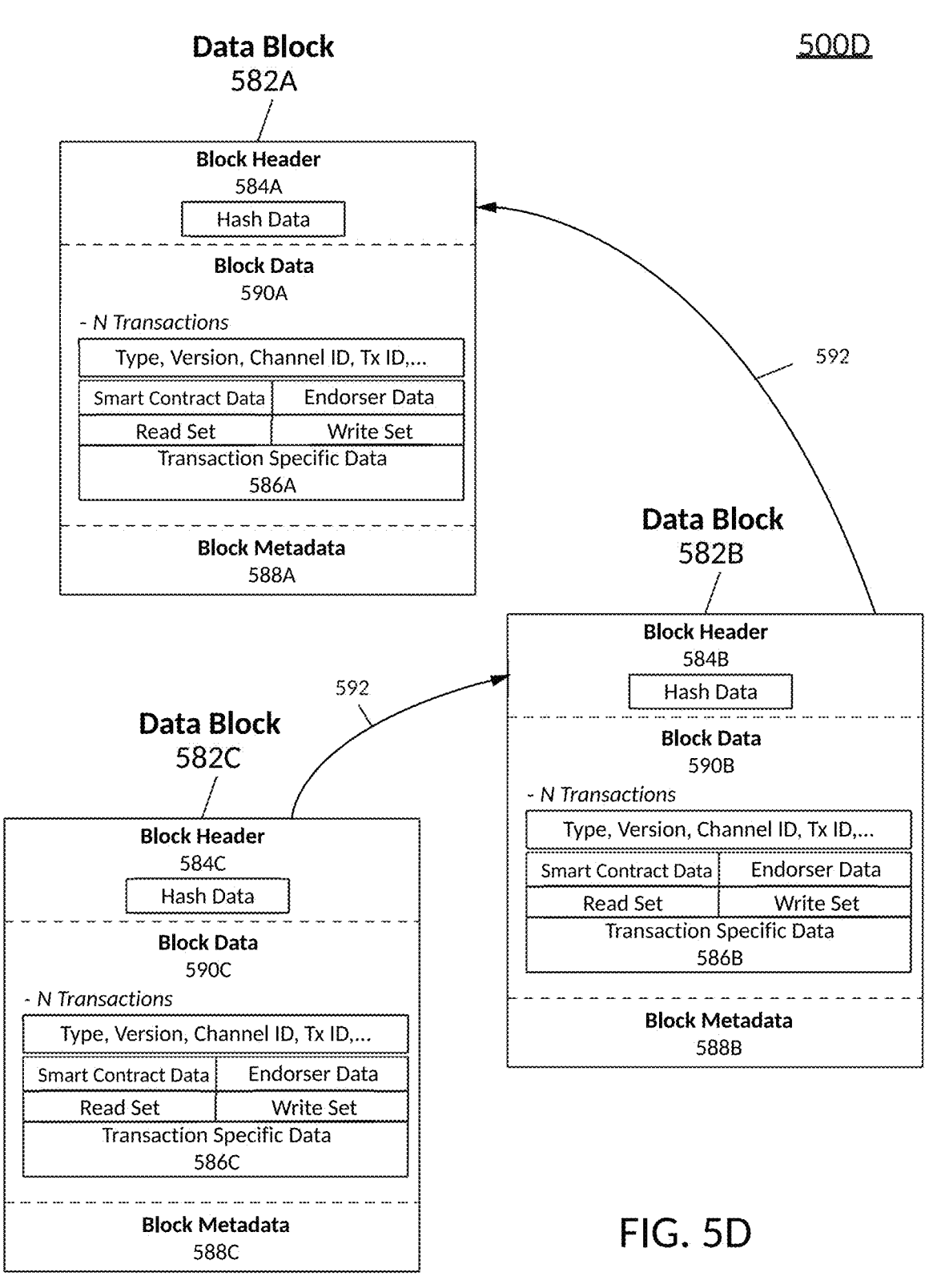
FIG. 5D illustrates an example data block interaction, according to example embodiments.

FIG. 5D illustrates blockchain blocks that can be added to a distributed ledger, according to example embodiments, and contents of block structures 582A to 582n. Referring to FIG. 5D, clients (not shown) may submit entries to blockchain nodes to enact activity on the blockchain. As an example, clients may be applications that act on behalf of a requester, such as a device, person, or entity to propose entries for the blockchain. The plurality of blockchain peers (e.g., blockchain nodes) may maintain a state of the blockchain network and a copy of the distributed ledger. Different types of blockchain nodes/peers may be present in the blockchain network including endorsing peers, which simulate and endorse entries proposed by clients and committing peers which verify endorsements, validate entries, and commit entries to the distributed ledger. In this example, the blockchain nodes may perform the role of endorser node, committer node, or both.

The instant system includes a blockchain that stores immutable, sequenced records in blocks, and a state database (current world state) maintaining a current state of the blockchain. One distributed ledger may exist per channel and each peer maintains its own copy of the distributed ledger for each channel of which they are a member. The instant blockchain is an entry log, structured as hash-linked blocks where each block contains a sequence of N entries. Blocks may include various components such as those shown in FIG. 5D. The linking of the blocks may be generated by adding a hash of a prior block's header within a block header of a current block. In this way, all entries on the blockchain are sequenced and cryptographically linked together preventing tampering with blockchain data without breaking the hash links. Furthermore, because of the links, the latest block in the blockchain represents every entry that has come before it. The instant blockchain may be stored on a peer file system (local or attached storage), which supports an append-only blockchain workload.

The current state of the blockchain and the distributed ledger may be stored in the state database. Here, the current state data represents the latest values for all keys ever included in the chain entry log of the blockchain. Smart contract executable code invocations execute entries against the current state in the state database. To make these smart contract executable code interactions extremely efficient, the latest values of all keys are stored in the state database. The state database may include an indexed view into the entry log of the blockchain, it can therefore be regenerated from the chain at any time. The state database may automatically get recovered (or generated if needed) upon peer startup, before entries are accepted.

Endorsing nodes receive entries from clients and endorse the entry based on simulated results. Endorsing nodes hold smart contracts, which simulate the entry proposals. When an endorsing node endorses an entry, the endorsing node creates an entry endorsement, which is a signed response from the endorsing node to the client application indicating the endorsement of the simulated entry. The method of endorsing an entry depends on an endorsement policy that may be specified within smart contract executable code. An example of an endorsement policy is "the majority of endorsing peers must endorse the entry." Different channels may have different endorsement policies. Endorsed entries are forwarded by the client application to an ordering service.

The ordering service accepts endorsed entries, orders them into a block, and delivers the blocks to the committing peers. For example, the ordering service may initiate a new block when a threshold of entries has been reached, a timer times out, or another condition is met. In this example, the blockchain node is a committing peer that has received a data block 582A for storage on the blockchain. The ordering service may be made up of a cluster of orderers. The ordering service does not process entries, smart contracts, or maintain the shared ledger. Rather, the ordering service may accept the endorsed entries and specify the order in which those entries are committed to the distributed ledger. The architecture of the blockchain network may be designed such that the specific implementation of 'ordering' becomes a pluggable component.

Entries are written to the distributed ledger in a consistent order. The order of entries is established to ensure that the updates to the state database are valid when they are committed to the network. Unlike a cryptocurrency blockchain system where ordering occurs through the solving of a cryptographic puzzle, or mining, in this example the parties of the distributed ledger may choose the ordering mechanism that best suits that network.

Referring to FIG. 5D, a block 582A (also referred to as a data block) that is stored on the blockchain and/or the distributed ledger may include multiple data segments such as a block header 584A to 584*n*, transaction-specific data 586A to 586*n*, and block metadata 588A to 588*n*. It should be appreciated that the various depicted blocks and their contents, such as block 582A and its contents are merely for purposes of an example and are not meant to limit the scope of the example embodiments. In some cases, both the block header 584A and the block metadata 588A may be smaller than the transaction-specific data 586A, which stores entry data; however, this is not a requirement. The block 582A may store transactional information of N entries (e.g., 100, 500, 1000, 2000, 3000, etc.) within the block data 590A to 590*n*. The block 582A may also include a link to a previous block (e.g., on the blockchain) within the block header 584A. In particular, the block header 584A may include a hash of a previous block's header. The block header 584A may also include a unique block number, a hash of the block data 590A of the current block 582A, and the like. The block number of the block 582A may be unique and assigned in an incremental/sequential order starting from zero. The first block in the blockchain may be referred to as a genesis block, which includes information about the blockchain, its members, the data stored therein, etc.

The block data 590A may store entry information of each entry that is recorded within the block. For example, the entry data may include one or more of a type of the entry, a version, a timestamp, a channel ID of the distributed ledger, an entry ID, an epoch, a payload visibility, a smart contract executable code path (deploy tx), a smart contract executable code name, a smart contract executable code version, an input (smart contract executable code and functions), a client (creator) identifier such as a public key and certificate, a signature of the client, identities of endorsers, endorser signatures, a proposal hash, smart contract executable code events, response status, namespace, a read set (list of key and version read by the entry, etc.), a write set (list of key and value, etc.), a start key, an end key, a list of keys, a Merkel tree query summary, and the like. The entry data may be stored for each of the N entries.

In some embodiments, the block data 590A may also store transaction-specific data 586A, which adds additional information to the hash-linked chain of blocks in the blockchain. Accordingly, the data 586A can be stored in an immutable log of blocks on the distributed ledger. Some of the benefits of storing such data 586A are reflected in the various embodiments disclosed and depicted herein. The block metadata 588A may store multiple fields of metadata (e.g., as a byte array, etc.). Metadata fields may include signature on block creation, a reference to a last configuration block, an entry filter identifying valid and invalid entries within the block, last offset persisted of an ordering service that ordered the block, and the like. The signature, the last configuration block, and the orderer metadata may be added by the ordering service. Meanwhile, a committer of the block (such as a blockchain node) may add validity/invalidity information based on an endorsement policy, verification of read/write sets, and the like. The entry filter may include a byte array of a size equal to the number of entries in the block data and a validation code identifying whether an entry was valid/invalid.

The other blocks 582B to 582*n* in the blockchain also have headers, files, and values. However, unlike the first block 582A, each of the headers 584A to 584*n* in the other blocks includes the hash value of an immediately preceding block. The hash value of the immediately preceding block may be just the hash of the header of the previous block or may be the hash value of the entire previous block. By including the hash value of a preceding block in each of the remaining blocks, a trace can be performed from the Nth block back to the genesis block (and the associated original file) on a block-by-block basis, as indicated by arrows 592, to establish an auditable and immutable chain-of-custody.

Figure 5E:
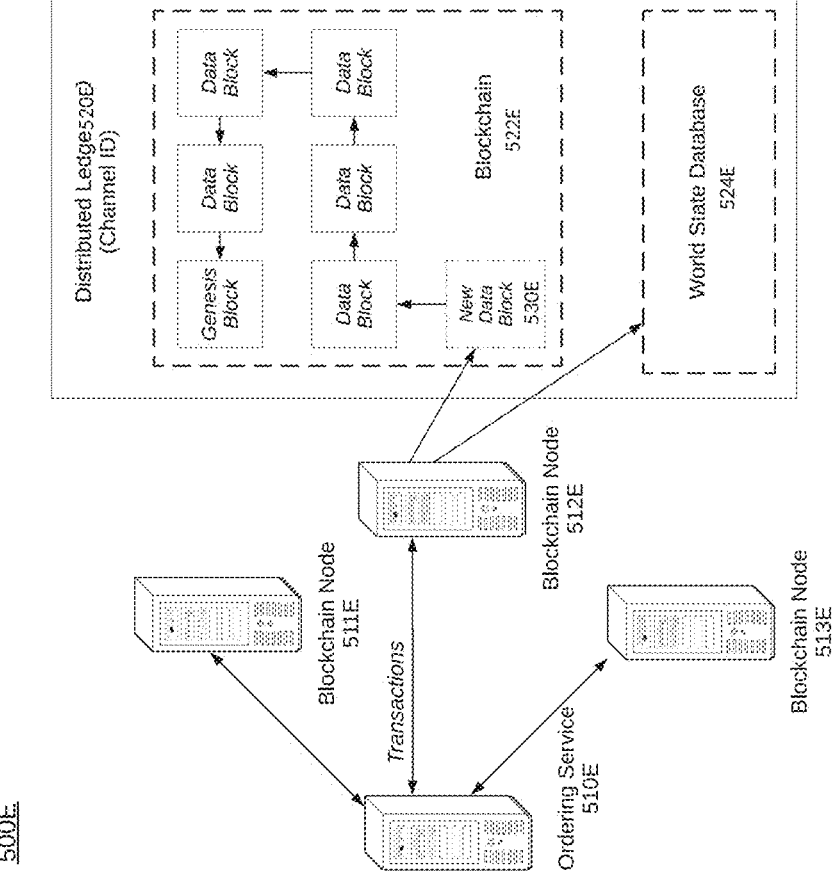
FIG. 5E illustrates a blockchain network diagram, according to example embodiments.

FIG. 5E illustrates a process 500E of a new block being added to a distributed ledger 520E, according to example embodiments, and FIG. 5D illustrates the contents of FIG. 5E's new data block structure 530E for blockchain, according to example embodiments. Referring to FIG. 5E, clients (not shown) may submit transactions to blockchain nodes 511E, 512E, and/or 513E. Clients may be instructions received from any source to enact activity on the blockchain 522E. As an example, clients may be applications that act on behalf of a requester, such as a device, person, or entity to propose transactions for the blockchain. The plurality of blockchain peers (e.g., blockchain nodes 511E, 512E, and 513E) may maintain a state of the blockchain network and a copy of the distributed ledger 520E. Different types of blockchain nodes/peers may be present in the blockchain network including endorsing peers which simulate and endorse transactions proposed by clients and committing peers which verify endorsements, validate transactions, and commit transactions to the distributed ledger 520E. In this example, the blockchain nodes 511E, 512E, and 513E may perform the role of endorser node, committer node, or both.

The distributed ledger 520E includes a blockchain which stores immutable, sequenced records in blocks, and a state database 524E (current world state) maintaining a current state of the blockchain 522E. One distributed ledger 520E may exist per channel and each peer maintains its own copy of the distributed ledger 520E for each channel of which they are a member. The blockchain 522E is a transaction log, structured as hash-linked blocks where each block contains a sequence of N transactions. The linking of the blocks (shown by arrows in FIG. 5E) may be generated by adding a hash of a prior block's header within a block header of a current block. In this way, all transactions on the blockchain 522E are sequenced and cryptographically linked together preventing tampering with blockchain data without breaking the hash links. Furthermore, because of the links, the latest block in the blockchain 522E represents every transaction that has come before it. The blockchain 522E may be stored on a peer file system (local or attached storage), which supports an append-only blockchain workload.

The current state of the blockchain 522E and the distributed ledger 520E may be stored in the state database 524E. Here, the current state data represents the latest values for all keys ever included in the chain transaction log of the blockchain 522E. Chaincode invocations execute transactions against the current state in the state database 524E. To make these chaincode interactions extremely efficient, the latest values of all keys are stored in the state database 524E. The state database 524E may include an indexed view into the transaction log of the blockchain 522E, and it can therefore be regenerated from the chain at any time. The state database 524E may automatically get recovered (or generated if needed) upon peer startup, before transactions are accepted.

Endorsing nodes receive transactions from clients and endorse the transaction based on simulated results. Endorsing nodes hold smart contracts which simulate the transaction proposals. When an endorsing node endorses a transaction, the endorsing node creates a transaction endorsement which is a signed response from the endorsing node to the client application indicating the endorsement of the simulated transaction. The method of endorsing a transaction depends on an endorsement policy which may be specified within chaincode. An example of an endorsement policy is "the majority of endorsing peers must endorse the transaction." Different channels may have different endorsement policies. Endorsed transactions are forwarded by the client application to the ordering service 510E.

The ordering service 510E accepts endorsed transactions, orders them into a block, and delivers the blocks to the committing peers. For example, the ordering service 510E may initiate a new block when a threshold of transactions has been reached, a timer times out, or another condition. In the example of FIG. 5E, blockchain node 512E is a committing peer that has received a new data block 530E for storage on blockchain 522E. The first block in the blockchain may be referred to as a genesis block which includes information about the blockchain, its members, the data stored therein, etc.

The ordering service 510E may be made up of a cluster of orderers. The ordering service 510E does not process transactions, smart contracts, or maintain the shared ledger. Rather, the ordering service 510E may accept the endorsed transactions and specifies the order in which those transactions are committed to the distributed ledger 522E. The architecture of the blockchain network may be designed such that the specific implementation of 'ordering' becomes a pluggable component.

Transactions are written to the distributed ledger 520E in a consistent order. The order of transactions is established to ensure that the updates to the state database 524E are valid when they are committed to the network. Unlike a cryptocurrency blockchain system where ordering occurs through the solving of a cryptographic puzzle, or mining, in this example the parties of the distributed ledger 520E may choose the ordering mechanism that best suits the network.

When the ordering service 510E initializes a new data block 530E, the new data block 530E may be broadcast to committing peers (e.g., blockchain nodes 511E, 512E, and 513E). In response, each committing peer validates the transaction within the new data block 530E by checking to make sure that the read set and the write set still match the current world state in the state database 524E. Specifically, the committing peer can determine whether the read data that existed when the endorsers simulated the transaction is identical to the current world state in the state database 524E. When the committing peer validates the transaction, the transaction is written to the blockchain 522E on the distributed ledger 520E, and the state database 524E is updated with the write data from the read-write set. If a transaction fails, that is, if the committing peer finds that the read-write set does not match the current world state in the state database 524E, the transaction ordered into a block will still be included in that block, but it will be marked as invalid, and the state database 524E will not be updated.

Referring to FIG. 5F 500F, a new data block 530 (also referred to as a data block) that is stored on the blockchain 522E of the distributed ledger 520E may include multiple data segments such as a block header 540, block data 550, and block metadata 560. It should be appreciated that the various depicted blocks and their contents, such as new data block 530 and its contents shown in FIG. 5F, are merely examples and are not meant to limit the scope of the example embodiments. The new data block 530 may store transactional information of N transaction(s) (e.g., 1, 10, 100, 500, 1000, 2000, 3000, etc.) within the block data 550. The new data block 530 may also include a link to a previous block (e.g., on the blockchain 522E in FIG. 5E) within the block header 540. In particular, the block header 540 may include a hash of a previous block's header. The block header 540 may also include a unique block number, a hash of the block data 550 of the new data block 530, and the like. The block number of the new data block 530 may be unique and assigned in various orders, such as an incremental/sequential order starting from zero.

The block data 550 may store transactional information of each transaction that is recorded within the new data block 530. For example, the transaction data may include one or more of a type of the transaction, a version, a timestamp, a channel ID of the distributed ledger 520E (shown in FIG. 5E), a transaction ID, an epoch, a payload visibility, a chaincode path (deploy tx), a chaincode name, a chaincode version, input (chaincode and functions), a client (creator) identify such as a public key and certificate, a signature of the client, identities of endorsers, endorser signatures, a proposal hash, chaincode events, response status, namespace, a read set (list of key and version read by the transaction, etc.), a write set (list of key and value, etc.), a start key, an end key, a list of keys, a Merkel tree query summary, and the like. The transaction data may be stored for each of the N transactions.

In one embodiment of the instant solution, the block data 564 may include data comprising one or more of receiving a request from a display device associated with a vehicle, wherein the request comprises a request to view content on the display device, determining content consuming attributes of a user of the display device based on content that has been consumed by the display device, determining that a different user of a different vehicle has similar content consuming attributes as the user based on content that has been consumed by a display device associated with the different vehicle, and outputting a content-sharing session to the display device associated with the vehicle and the display device associate with the different vehicle.

Although in FIG. 5F the blockchain data 563 is depicted in the block data 550 but may also be located in the block header 540 or the block metadata 560. In some embodiments, the sleep data of the individual, the changes to the settings on the vehicle generated by the AI model based on the sleep state, and the like, may be written to the blockchain data 563 and committed to a blockchain ledger.

The block metadata 560 may store multiple fields of metadata (e.g., as a byte array, etc.). Metadata fields may include signature on block creation, a reference to a last configuration block, a transaction filter identifying valid and invalid transactions within the block, last offset persisted of an ordering service that ordered the block, and the like. The signature, the last configuration block, and the orderer metadata may be added by the ordering service 510E in FIG. 5E. Meanwhile, a committer of the block (such as blockchain node 512E in FIG. 5E) may add validity/invalidity information based on an endorsement policy, verification of read/write sets, and the like. The transaction filter may include a byte array of a size equal to the number of transactions in the block data and a validation code identifying whether a transaction was valid/invalid.

The above embodiments may be implemented in hardware, in a computer program executed by a processor, in firmware, or in a combination of the above. A computer program may be embodied on a computer-readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application-specific integrated circuit ("ASIC"). In the alternative, the processor and the storage medium may reside as discrete components. For example, FIG. 6 illustrates an example computer system architecture 600, which may represent or be integrated in any of the above-described components, etc.

Figure 6:
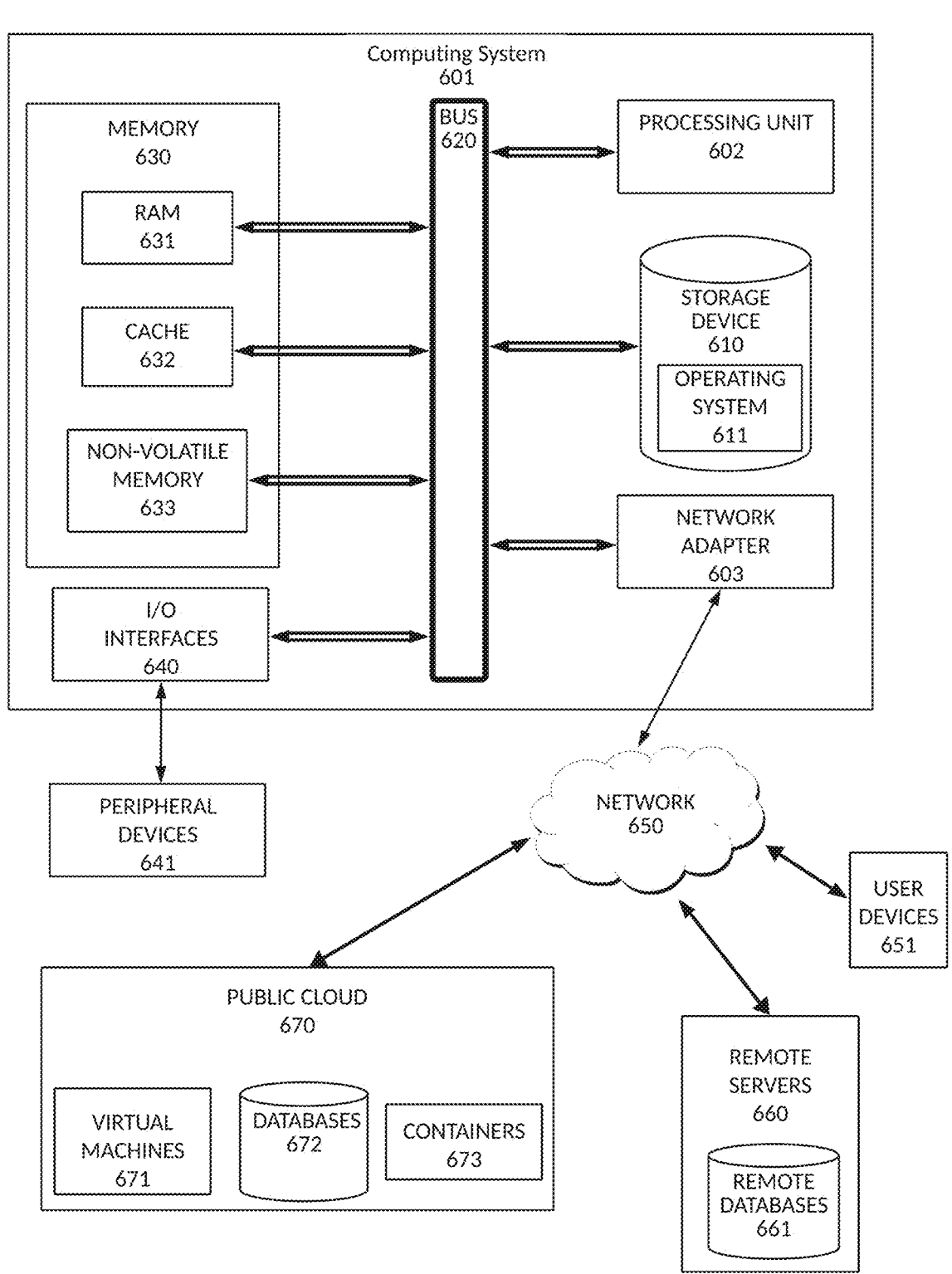
FIG. 6 illustrates an example system that supports one or more of the example embodiments.

FIG. 6 illustrates a computing environment according to example embodiments. FIG. 6 is not intended to suggest any limitation as to the scope of use or functionality of embodiments of the application described herein. Regardless, the computing environment 600 can be implemented to perform any of the functionalities described herein. In computer environment 600, computer system 601 is operational within numerous other general-purpose or special-purpose computing system environments or configurations.

Computer system 601 may take the form of a desktop computer, laptop computer, tablet computer, smartphone, smartwatch or other wearable computer, server computer system, thin client, thick client, network PC, minicomputer system, mainframe computer, quantum computer, and distributed cloud computing environment that includes any of the described systems or devices, and the like or any other form of computer or mobile device now known or to be developed in the future that is capable of running a program, accessing a network 650 or querying a database. Depending upon the technology, the performance of a computer-implemented method may be distributed among multiple computers and between multiple locations. However, in this presentation of the computing environment 600, a detailed discussion is focused on a single computer, specifically computer system 601, to keep the presentation as simple as possible.

Computer system 601 may be located in a cloud, even though it is not shown in a cloud in FIG. 6. On the other hand, computer system 601 is not required to be in a cloud except to any extent as may be affirmatively indicated. Computer system 601 may be described in the general context of computer system-executable instructions, such as program modules, executed by a computer system 601. Generally, program modules may include routines, programs, objects, components, logic, data structures, and so on that perform tasks or implement certain abstract data types. As shown in FIG. 6, computer system 601 in computing environment 600 is shown in the form of a general-purpose computing device. The components of computer system 601 may include but are not limited to, one or more processors or processing units 602, a system memory 630, and a bus 620 that couples various system components, including system memory 630 to processor 602.

Processing unit 602 includes one or more computer processors of any type now known or to be developed. The processing unit 602 may contain circuitry distributed over multiple integrated circuit chips. The processing unit 602 may also implement multiple processor threads and multiple processor cores. Cache 632 is a memory that may be in the processor chip package(s) or located "off-chip," as depicted in FIG. 6. Cache 632 is typically used for data or code that the threads or cores running on the processing unit 602 should be available for rapid access. In some computing environments, processing unit 602 may be designed to work with qubits and perform quantum computing.

Network adapter 603 enables the computer system 601 to connect and communicate with one or more networks 650, such as a local area network (LAN), a wide area network (WAN), and/or a public network (e.g., the Internet). It bridges the computer's internal bus 620 and the external network, exchanging data efficiently and reliably. The network adapter 603 may include hardware, such as modems or Wi-Fi® signal transceivers, and software for packetizing and/or de-packetizing data for communication network transmission. Network adapter 603 supports various communication protocols to ensure compatibility with network standards. For Ethernet connections, it adheres to protocols such as IEEE 802.3, while for wireless communications, it might support IEEE 802.11 standards, Bluetooth®, near-field communication (NFC), or other network wireless radio standards.

Computer system 601 may include a removable/non-removable, volatile/non-volatile computer storage device 610. By way of example only, storage device 610 can be a non-removable, non-volatile magnetic media (not shown and typically called a "hard drive"). One or more data interfaces can connect it to the bus 620. In embodiments where computer system 601 is required to have a large amount of storage (for example, where computer system 601 locally stores and manages a large database), then this storage may be provided by peripheral storage devices 610 designed for storing very large amounts of data, such as a storage area network (SAN) that is shared by multiple, geographically distributed computers.

The operating system 611 is software that manages computer system 601 hardware resources and provides common services for computer programs. Operating system 611 may take several forms, such as various known proprietary operating systems or open-source Portable Operating System Interface type operating systems that employ a kernel.

The Bus 620 represents one or more of several types of bus structures, including a memory bus or memory controller, a peripheral bus, an accelerated graphics port, and a processor or local bus using various bus architectures. By way of example, and not limitation, such architectures include Industry Standard Architecture (ISA) buses, Micro Channel Architecture (MCA) buses, Enhanced ISA (EISA) buses, Video Electronics Standards Association (VESA) local buses, and Peripheral Component Interconnects (PCI) bus. The bus 620 is the signal conduction path that allows the various components of computer system 601 to communicate with each other.

Memory 630 is any volatile memory now known or to be developed in the future. Examples include dynamic random-access memory (RAM 631) or static type RAM 631. Typically, the volatile memory is characterized by random access, but this is not required unless affirmatively indicated. In computer system 601, memory 630 is in a single package and is internal to computer system 601, but alternatively or additionally, the volatile memory may be distributed over multiple packages and/or located externally with respect to computer system 601. By way of example only, memory 630 can be provided for reading from and writing to a non-removable, non-volatile magnetic media (shown as storage device 610, and typically called a "hard drive"). Memory 630 may include at least one program product having a set (e.g., at least one) of program modules configured to carry out various functions. A typical computer system 601 may include cache 632, a specialized volatile memory generally faster than RAM 631 and generally located closer to the processing unit 602. Cache 632 stores frequently accessed data and instructions accessed by the processing unit 602 to speed up processing time. The computer system 601 may include non-volatile memory 633 in ROM, PROM, EEPROM, and flash memory. Non-volatile memory 633 often contains programming instructions for starting the computer, including the BIOS and information required to start the operating system 611.

Computer system 601 may also communicate with one or more peripheral devices 641 via an I/O interface 640. Such devices may include a keyboard, a pointing device, a display, etc.; one or more devices that enable a user to interact with computer system 601; and/or any devices (e.g., network card, modem, etc.) that enable computer system 601 to communicate with one or more other computing devices. Such communication can occur via input/output (I/O) interfaces 640. As depicted, IO interface 640 communicates with the other components of computer system 601 via bus 620.

Network 650 is any computer network that can receive and/or transmit data. Network 650 can include a WAN, LAN, private cloud, or public Internet, capable of communicating computer data over non-local distances by any technology that is now known or to be developed in the future. Any connection depicted can be wired and/or wireless and may traverse other components that are not shown. In some embodiments, a network 650 may be replaced and/or supplemented by LANs designed to communicate data between devices located in a local area, such as a Wi-Fi® network. The network 650 typically includes computer hardware such as copper transmission cables, optical transmission fibers, wireless transmission, routers, firewalls, switches, gateway computers, and edge servers. Computer system 601 connects to network 650 via network adapter 603 and bus 620.

User devices 651 are any computer systems used and controlled by an end user in connection with computer system 601. For example, in a hypothetical case where computer system 601 is designed to provide a recommendation to an end user, this recommendation may typically be communicated from network adapter 603 of computer system 601 through network 650 to a user device 651, allowing user device 651 to display, or otherwise present, the recommendation to an end user. User devices can be a wide array of devices, including PCs, laptops, tablets, hand-held, mobile phones, etc.

Remote servers 660 are any computers that serve at least some data and/or functionality over a network 650, for example, WAN, a virtual private network (VPN), a private cloud, or via the Internet to computer system 601. These networks 650 may communicate with a LAN to reach users. The user interface may include a web browser or an application that facilitates communication between the user and remote data. Such applications have been called "thin" desktops or "thin clients." Thin clients typically incorporate software programs to emulate desktop sessions. Mobile applications can also be used. Remote servers 660 can also host remote databases 661, with the database located on one remote server 660 or distributed across multiple remote servers 660. Remote databases 661 are accessible from database client applications installed locally on the remote server 660, other remote servers 660, user devices 651, or computer system 601 across a network 650.

A public cloud 670 is an on-demand availability of computer system resources, including data storage and computing power, without direct active management by the user. Public clouds 670 are often distributed, with data centers in multiple locations for availability and performance. Computing resources on public clouds 670 are shared across multiple tenants through virtual computing environments comprising virtual machines 671, databases 672, containers 673, and other resources. A container 673 is an isolated, lightweight software for running an application on the host operating system 611. Containers 673 are built on top of the host operating system's kernel and contain only apps and some lightweight operating system APIs and services. In contrast, virtual machine 671 is a software layer that includes a complete operating system 611 and kernel. Virtual machines 671 are built on top of a hypervisor emulation layer designed to abstract a host computer's hardware from the operating software environment. Public clouds 670 generally offer hosted databases 672 abstracting high-level database management activities. It should be further understood that one or more of the elements described or depicted in FIG. 6 can perform one or more of the actions, functionalities, or features described or depicted herein.

Although an exemplary embodiment of at least one of a system, method, and non-transitory computer-readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver, or pair of both. For example, all or part of the functionality performed by the individual module, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" may be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules to more particularly emphasize their implementation independence. For example, a module may be implemented as a hardware circuit comprising custom very-large-scale integration (VLSI) circuits or gate arrays, off-the-shelf semiconductors such as logic chips, transistors, or other discrete components. A module may also be implemented in programmable hardware devices such as field-programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations that, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations, including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order and/or with hardware elements in configurations that are different from those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method performed by a vehicle, the method comprising:
   identifying a state of an individual associated with the vehicle based on data of the individual stored in a profile;
   determining a current time;
   identifying a setting of the vehicle to change based on an execution of an artificial intelligence (AI) model on the state and the current time; and
   changing the setting while the individual is in the vehicle.

2. The method of claim 1, comprising:
   receiving sleep data of the individual from a sensor worn by the individual while outside of the vehicle; and
   storing the sleep data in the profile,
   wherein the identifying of the state comprises:
      identifying a circadian rhythm of the individual based on the sleep data.

3. The method of claim 1, comprising:
   receiving data from a mobile device of the individual, wherein the data comprises sleep preferences of the individual; and storing the sleep preferences in the profile,
   wherein the identifying of the state of the individual comprises:
      identifying a circadian rhythm of the individual based on the sleep preferences.

4. The method of claim 1, wherein the determining of the current time comprises:
   determining the current time based on one or more of a clock of the vehicle or an ambient light sensor of the vehicle.

5. The method of claim 1, wherein the changing of the setting comprises:
   receiving a value for the setting from the AI model; and
   applying the value to the vehicle.

6. The method of claim 1, wherein the setting-controls a lighting system in the vehicle and audio content output from an infotainment system of the vehicle.

7. The method of claim 1, wherein the setting controls one or more of:
   a steering wheel position, an armrest position, a mirror position, or a sunshade position.

8. A vehicle comprising:
   a processor that executes instructions stored in a memory to configure the processor to:
      identify a state of an individual associated with the vehicle based on data of the individual stored in a profile;
      determine a current time;
      identify a setting of the vehicle to change based on an execution of an artificial intelligence (AI) model on the state and the current time; and
      change the setting while the individual is in the vehicle.

9. The apparatus of claim 8, wherein the processor is configured to:
   receive sleep data of the individual from a sensor worn by the individual while outside of the vehicle; and
   store the sleep data in the profile,
   wherein, when the processor identifies the state, the processor is configured to:
      identify a circadian rhythm of the individual based on the sleep data.

10. The apparatus of claim 8, wherein the processor is configured to:
   receive data from a mobile device of the individual, wherein the data comprises sleep preferences of the individual; and
   store the sleep preferences in the profile,
   wherein, when the processor identifies the state, the processor is configured to:
      identify a circadian rhythm of the individual based on the sleep preferences.

11. The apparatus of claim 8, wherein the processor is configured to:
   determine the current time based on one or more of a clock of the vehicle or an ambient light sensor of the vehicle.

12. The apparatus of claim 8, wherein the processor is configured to:
   receive a value for the setting from the AI model; and
   apply the value to the vehicle.

13. The apparatus of claim 8, wherein the setting controls a lighting system in the vehicle and audio content output from an infotainment system of the vehicle.

14. The apparatus of claim 8, wherein the setting controls one or more of:
   a steering wheel position, an armrest position, a mirror position, or a sunshade position.

15. A computer-readable medium comprising instructions that, when executed by a processor of a vehicle, cause the processor to perform:

identifying a state of an individual associated with the vehicle based on data of the individual stored in a profile;

determining a current time;

identifying a setting of the vehicle to change based on an execution of an artificial intelligence (AI) model on the state and the current time; and changing the setting while the individual is in the vehicle.

16. The computer-readable medium of claim 15, wherein the instructions cause processor to perform:

receiving sleep data of the individual from a sensor worn by the individual while outside of the vehicle; and storing the sleep data in the profile, wherein the identifying of the state comprises:

identifying a circadian rhythm of the individual based on the sleep data.

17. The computer-readable medium of claim 15, wherein the instructions cause processor to perform:

receiving data from a mobile device of the individual, wherein the data comprises sleep preferences of the individual; and storing the sleep preferences in the profile, wherein the identifying of the state comprises:

identifying a circadian rhythm of the individual based on the sleep preferences.

18. The computer-readable medium of claim 15, wherein the determining of the current time comprises:

determining the current time based on one or more of a clock of the vehicle or an ambient light sensor of the vehicle.

19. The computer-readable medium of claim 15, wherein the changing of the setting comprises:

receiving a value for the setting from the AI model; and applying the value to the vehicle.

20. The computer-readable medium of claim 15, wherein the setting controls one or more of:

a steering wheel position, an armrest position, a mirror position, or a sunshade position.

* * * * *